(12) United States Patent
Yeung et al.

(10) Patent No.: US 11,918,311 B2
(45) Date of Patent: *Mar. 5, 2024

(54) ROBOTIC DEVICES AND SYSTEMS FOR PERFORMING SINGLE INCISION PROCEDURES AND NATURAL ORIFICE TRANSLUMENAL ENDOSCOPIC SURGICAL PROCEDURES, AND METHODS OF CONFIGURING ROBOTIC DEVICES AND SYSTEMS

(71) Applicant: Bio-Medical Engineering (HK) Limited, Hong Kong (CN)

(72) Inventors: Chung Kwong Yeung, Hong Kong (CN); Wing Fai Lam, Hong Kong (CN); Wai Leung William Cheng, Hong Kong (CN)

(73) Assignee: IEMIS (HK) Limited, Hong Kong (HK)

( * ) Notice: Subject to any disclaimer, the term of this patent is extended or adjusted under 35 U.S.C. 154(b) by 250 days.

This patent is subject to a terminal disclaimer.

(21) Appl. No.: 17/392,213

(22) Filed: Aug. 2, 2021

(65) Prior Publication Data
US 2021/0361367 A1 Nov. 25, 2021

Related U.S. Application Data

(63) Continuation of application No. 16/172,408, filed on Oct. 26, 2018, now Pat. No. 11,103,323, which is a (Continued)

(51) Int. Cl.
*A61B 34/30* (2016.01)
*A61B 17/34* (2006.01)
(Continued)

(52) U.S. Cl.
CPC .......... *A61B 34/37* (2016.02); *A61B 17/3421* (2013.01); *A61B 17/3423* (2013.01);
(Continued)

(58) Field of Classification Search
CPC ..... A61B 1/00147; A61B 1/05; A61B 1/3132; A61B 17/3421; A61B 17/3423;
(Continued)

(56) References Cited

U.S. PATENT DOCUMENTS 9,010,214 B2 * 4/2015 Markvicka ............ A61B 34/30
74/490.03
2008/0065099 A1 * 3/2008 Cooper .............. A61B 1/00193
901/14
(Continued)

*Primary Examiner* — Michael F Peffley
(74) *Attorney, Agent, or Firm* — Baker & Mckenzie LLP

(57) ABSTRACT

Example embodiments relate to surgical systems. The system includes an end-effector assembly having an instrument. The system includes a first arm assembly. A distal end of first arm assembly is securable to the end-effector assembly. The system includes an elbow joint assembly. A distal end of elbow joint assembly is secured to a proximal end of first arm assembly. A proximal end of elbow joint assembly is secured to a distal end of second arm assembly. The second arm assembly includes a first elbow drive assembly. The first elbow drive assembly includes an integrated motor for driving the elbow joint assembly to pivotally move the first arm assembly relative to an axis. The second arm assembly also includes a second elbow drive assembly. The second elbow drive assembly includes an integrated motor for driving the elbow joint assembly to pivotally move the first arm assembly relative to another axis.

27 Claims, 40 Drawing Sheets

Related U.S. Application Data continuation of application No. 15/864,628, filed on Jan. 8, 2018, now Pat. No. 10,172,680, which is a continuation of application No. 15/605,864, filed on May 25, 2017, now Pat. No. 9,895,200, which is a continuation-in-part of application No. 15/340,678, filed on Nov. 1, 2016, now Pat. No. 9,855,108, and a continuation-in-part of application No. 15/340,660, filed on Nov. 1, 2016, now Pat. No. 9,724,168, said application No. 15/864,628 is a continuation of application No. 15/340,699, filed on Nov. 1, 2016, now Pat. No. 9,827,058, said application No. 15/340,660 is a continuation-in-part of application No. 15/044,889, filed on Feb. 16, 2016, now Pat. No. 9,737,372, said application No. 15/605,864 is a continuation-in-part of application No. 15/044,895, filed on Feb. 16, 2016, now Pat. No. 11,090,123, said application No. 15/340,678 is a continuation-in-part of application No. 15/044,895, filed on Feb. 16, 2016, now Pat. No. 11,090,123, said application No. 15/340,660 is a continuation-in-part of application No. 15/044,895, filed on Feb. 16, 2016, now Pat. No. 11,090,123, said application No. 15/605,864 is a continuation-in-part of application No. 15/044,889, filed on Feb. 16, 2016, now Pat. No. 9,737,372, said application No. 15/340,678 is a continuation-in-part of application No. 15/044,889, filed on Feb. 16, 2016, now Pat. No. 9,737,372, which is a continuation-in-part of application No. 14/693,207, filed on Apr. 22, 2015, now Pat. No. 11,154,183, said application No. 15/605,864 is a continuation-in-part of application No. 14/693,207, filed on Apr. 22, 2015, now Pat. No. 11,154,183, said application No. 15/340,678 is a continuation-in-part of application No. 14/693,207, filed on Apr. 22, 2015, now Pat. No. 11,154,183, said application No. 15/044,895 is a continuation-in-part of application No. 14/693,207, filed on Apr. 22, 2015, now Pat. No. 11,154,183.

(60) Provisional application No. 61/982,717, filed on Apr. 22, 2014.

(51) Int. Cl.
| | | |
|---|---|---|
| *A61B 18/14* | (2006.01) | |
| *A61B 34/00* | (2016.01) | |
| *A61B 34/37* | (2016.01) | |
| *A61B 90/00* | (2016.01) | |
| *A61B 90/30* | (2016.01) | |
| *A61B 1/00* | (2006.01) | |
| *A61B 1/05* | (2006.01) | |
| *A61B 1/313* | (2006.01) | |
| *A61B 17/00* | (2006.01) | |
| *A61B 17/29* | (2006.01) | |
| *A61B 18/00* | (2006.01) | |
| *A61B 90/57* | (2016.01) | |

(52) U.S. Cl.
CPC .......... *A61B 18/1445* (2013.01); *A61B 34/30* (2016.02); *A61B 34/76* (2016.02); *A61B 90/30* (2016.02); *A61B 90/361* (2016.02); *A61B 90/37* (2016.02); *A61B 1/00147* (2013.01); *A61B 1/05* (2013.01); *A61B 1/3132* (2013.01); *A61B 2017/00283* (2013.01); *A61B 2017/2906* (2013.01); *A61B 2017/3445* (2013.01); *A61B 2017/345* (2013.01); *A61B 2017/3452* (2013.01); *A61B 2017/346* (2013.01); *A61B 2018/00589* (2013.01); *A61B 2018/00601* (2013.01); *A61B 18/1442* (2013.01); *A61B 2034/301* (2016.02); *A61B 2034/302* (2016.02); *A61B 2034/305* (2016.02); *A61B 2034/306* (2016.02); *A61B 2090/309* (2016.02); *A61B 2090/3612* (2016.02); *A61B 2090/571* (2016.02); *Y10S 901/02* (2013.01); *Y10S 901/27* (2013.01)

(58) Field of Classification Search
CPC ............ A61B 18/1442; A61B 18/1445; A61B 2017/00283; A61B 2017/00362; A61B 2017/2906; A61B 2017/3445; A61B 2017/345; A61B 2017/3452; A61B 2017/346; A61B 2034/301; A61B 2034/302; A61B 2034/305; A61B 2034/306; A61B 2090/3612; A61B 2090/571; A61B 34/30; A61B 34/37; A61B 34/76; A61B 90/30; A61B 90/361; A61B 90/37; Y10S 901/02; Y10S 901/27
See application file for complete search history.

(56) References Cited

U.S. PATENT DOCUMENTS

| | | | |
|---|---|---|---|
| 2013/0131695 A1* | 5/2013 | Scarfogliero | A61B 34/30 606/130 |
| 2017/0035526 A1* | 2/2017 | Farritor | A61B 34/76 |

\* cited by examiner

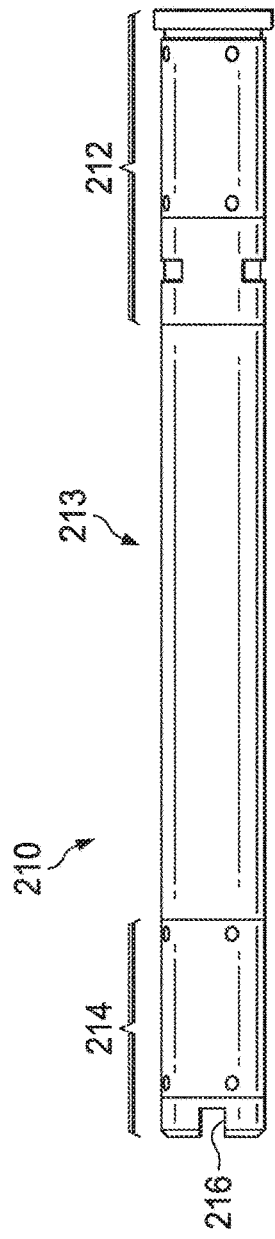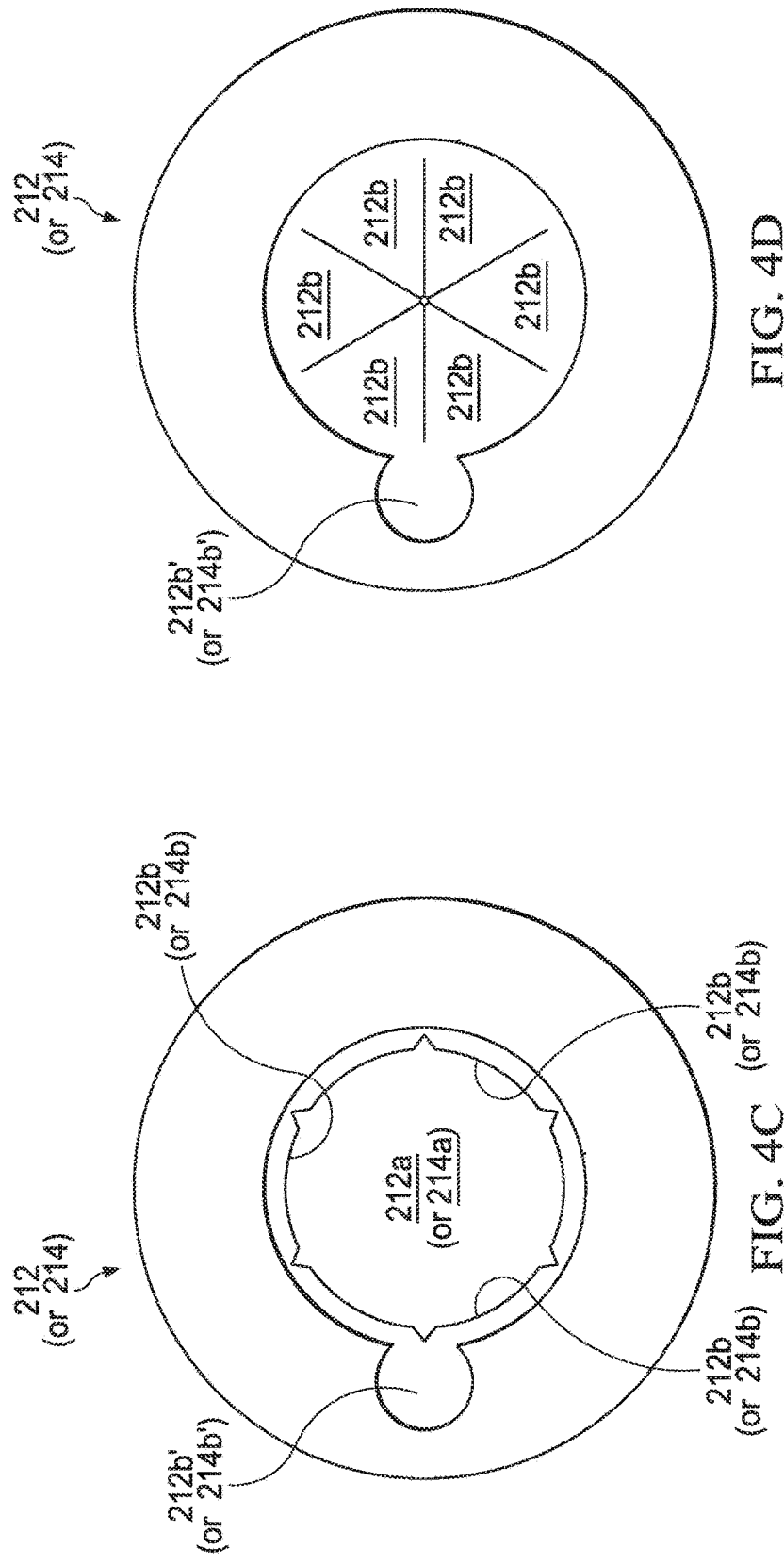

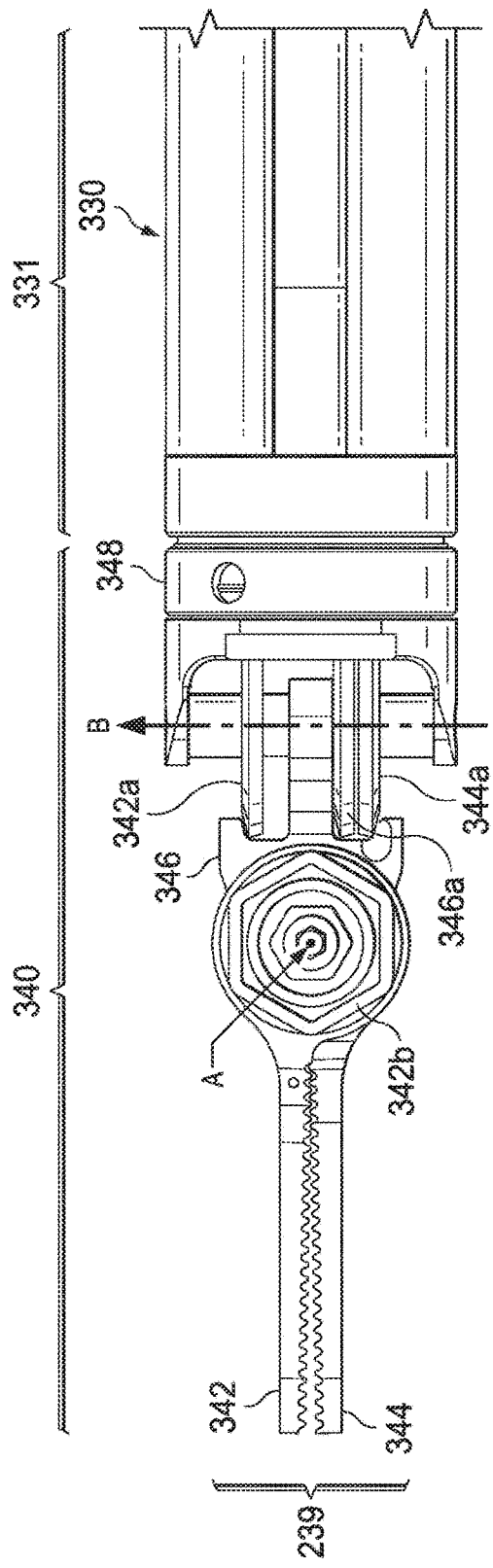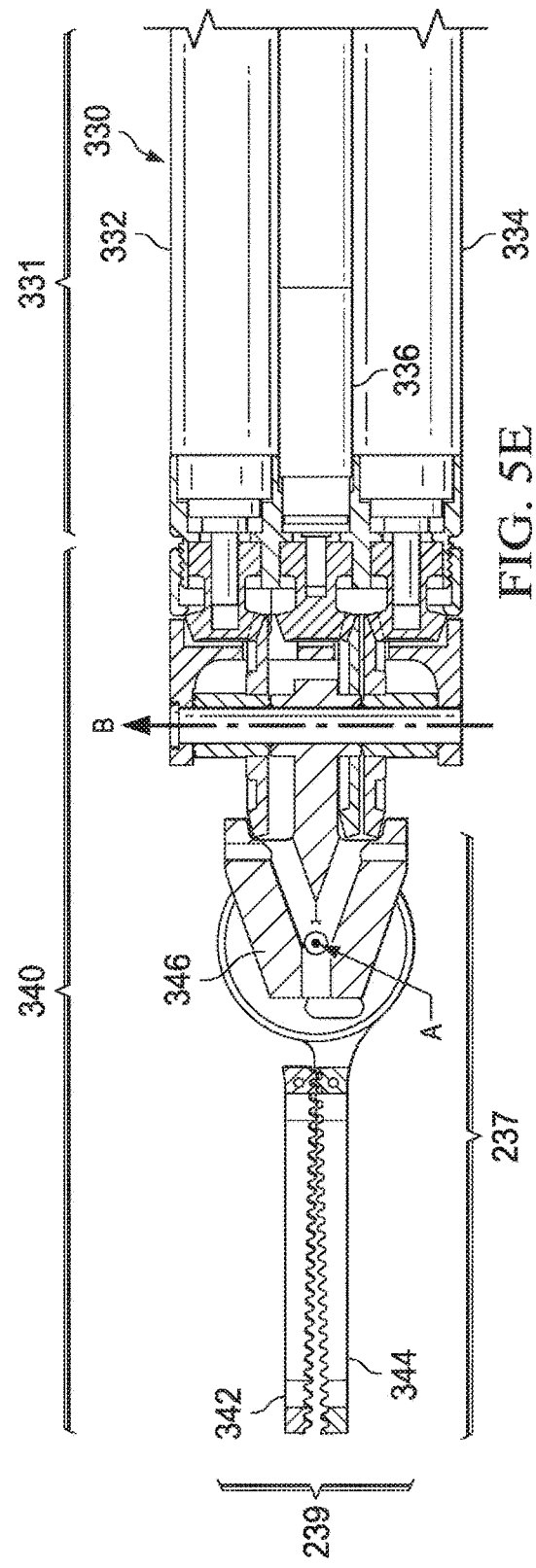

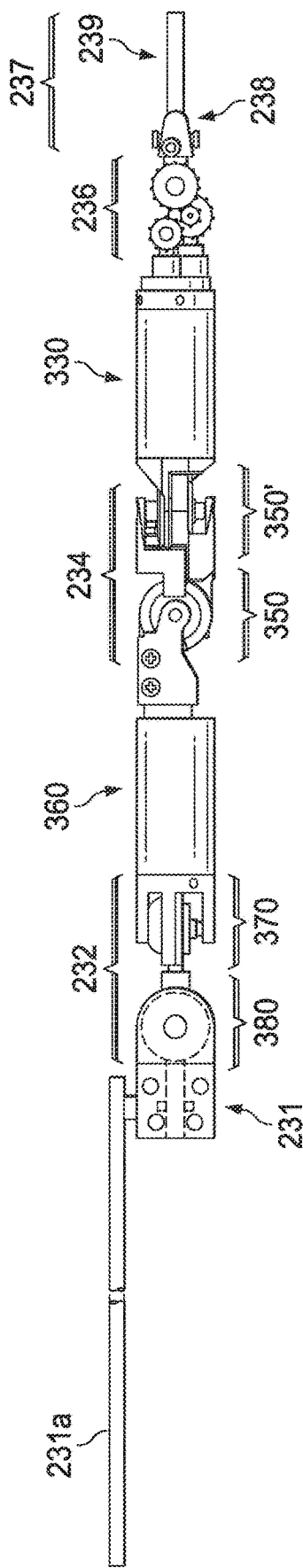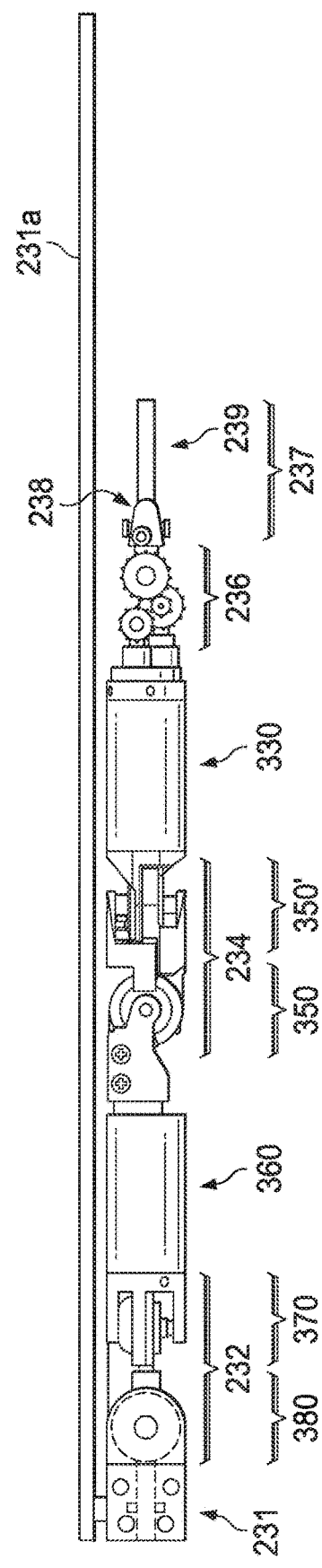

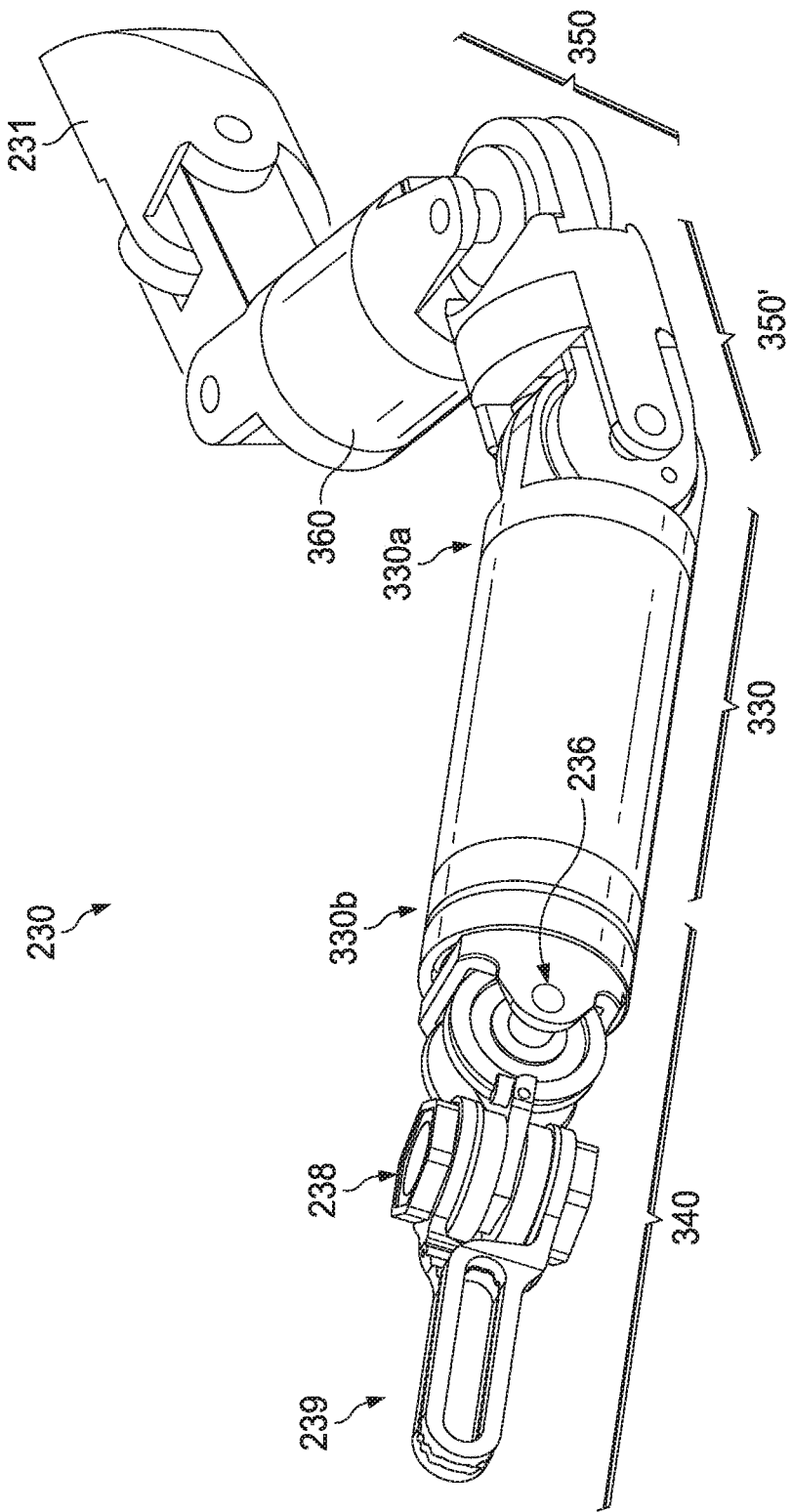

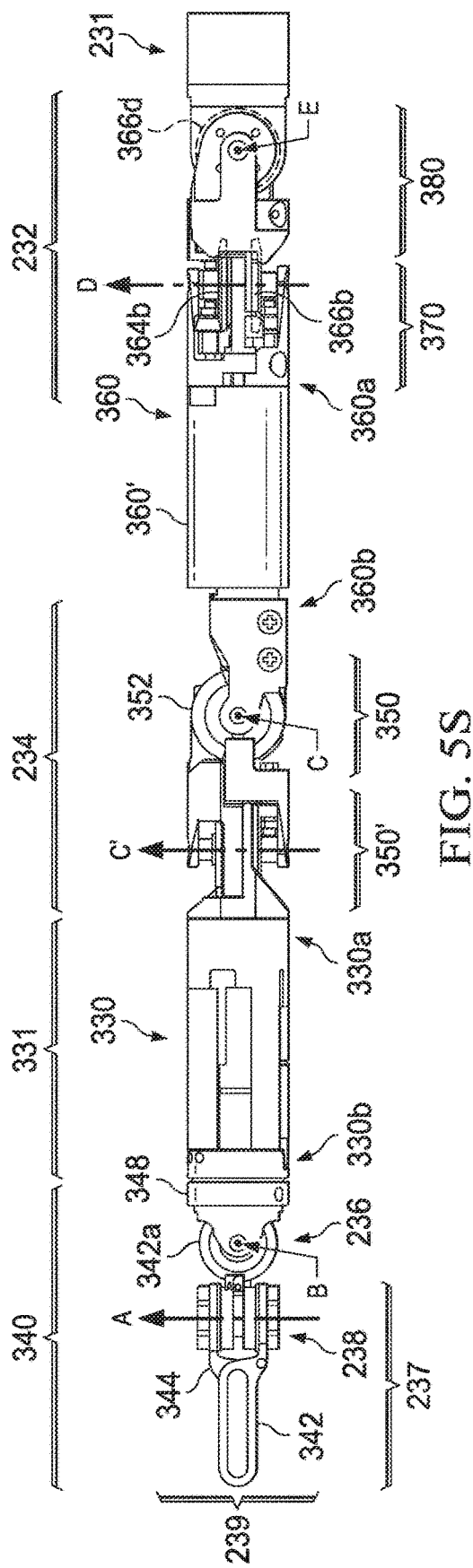
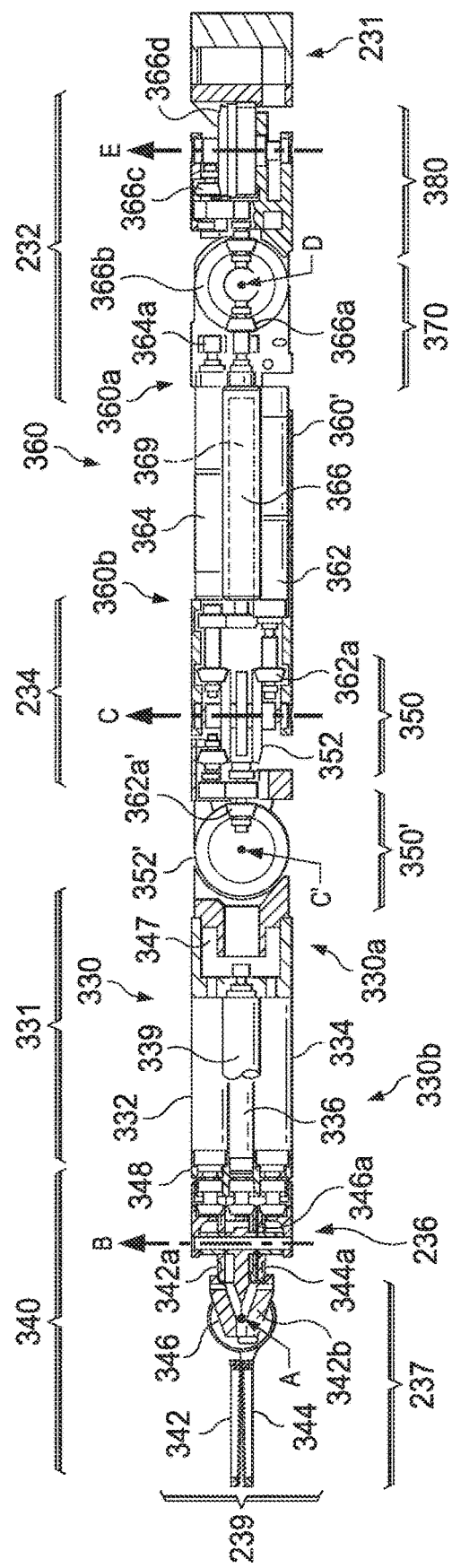
FIG. 5S
FIG. 5T

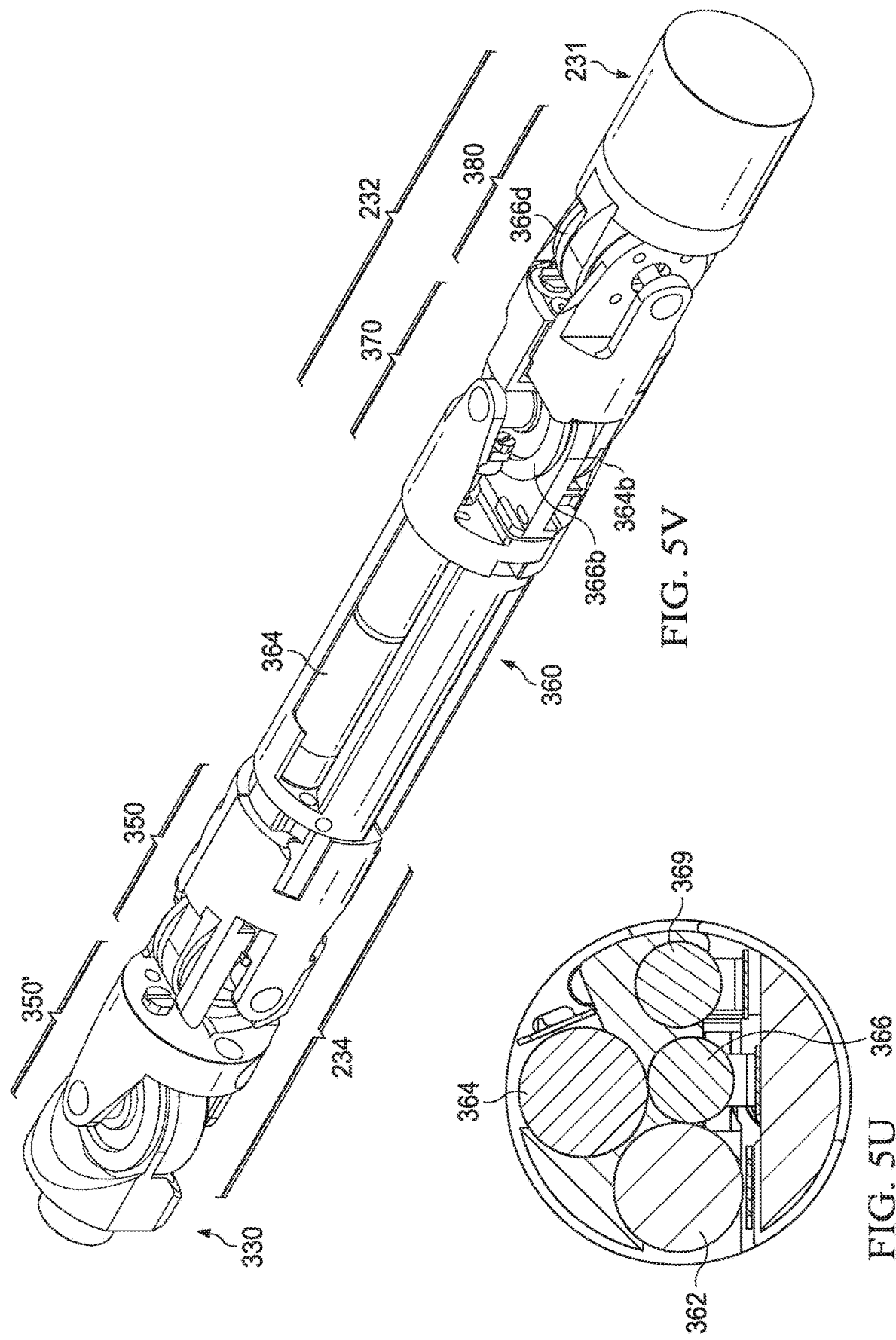

ROBOTIC DEVICES AND SYSTEMS FOR PERFORMING SINGLE INCISION PROCEDURES AND NATURAL ORIFICE TRANSLUMENAL ENDOSCOPIC SURGICAL PROCEDURES, AND METHODS OF CONFIGURING ROBOTIC DEVICES AND SYSTEMS

CROSS-REFERENCE TO RELATED APPLICATIONS

This application is a continuation of U.S. application Ser. No. 16/172,408 (filed on Oct. 26, 2018 and granted as U.S. Pat. No. 11,103,323), which is a continuation of U.S. application Ser. No. 15/864,628 (filed on Jan. 8, 2018 and granted as U.S. Pat. No. 10,172,680), which is a continuation of U.S. application Ser. No. 15/605,864 (filed on May 25, 2017 and granted as U.S. Pat. No. 9,895,200), which is a:

(A) continuation-in-part of U.S. application Ser. No. 15/340,660 (filed on Nov. 1, 2016 and granted as U.S. Pat. No. 9,724,138, which is a continuation-in-part of U.S. application Ser. No. 15/044,889 (granted as U.S. Pat. No. 9,737,372), a continuation-in-part of U.S. application Ser. No. 15/044,895 (filed on Feb. 16, 2016 and granted as U.S. Pat. No. 11,090,123), and a continuation-in-part of U.S. application Ser. No. 14/693,207 (filed on Apr. 22, 2015 and granted as U.S. Pat. No. 11,154,183), which claims priority to U.S. Provisional Application No. 61/982,717);

(B) continuation-in-part of U.S. application Ser. No. 15/340,678 (filed on Nov. 1, 2016 and granted as U.S. Pat. No. 9,855,108, which is a continuation-in-part of U.S. application Ser. No. 15/044,889 (granted as U.S. Pat. No. 9,737,372), a continuation-in-part of U.S. application Ser. No. 15/044,895 (filed on Feb. 16, 2016 and granted as U.S. Pat. No. 11,090,123), and a continuation-in-part of U.S. application Ser. No. 14/693,207 (filed on Apr. 22, 2015 and granted as U.S. Pat. No. 11,154,183), which claims priority to U.S. Provisional Application No. 61/982,717);

(C) continuation-in-part of U.S. application Ser. No. 15/340,699 (filed on Nov. 1, 2016 and granted as U.S. Pat. No. 9,827,058);

(D) continuation-in-part of U.S. application Ser. No. 14/693,207 (filed on Apr. 22, 2015 and granted as U.S. Pat. No. 11,154,183, which claims priority to U.S. Provisional Application No. 61/982,717, filed on Apr. 22, 2014);

(E) continuation-in-part of U.S. application Ser. No. 15/044,895 (filed on Feb. 16, 2016 and granted as U.S. Pat. No. 11,090,123, which is a continuation-in-part of U.S. application Ser. No. 14/693,207 (filed on Apr. 22, 2015 and granted as U.S. Pat. No. 11,154,183), which claims priority to U.S. Provisional Application No. 61/982,717); and (F) continuation-in-part of U.S. application Ser. No. 15/044,889 (filed on Feb. 16, 2016 and granted as U.S. Pat. No. 9,737,372, which is a continuation-in-part of U.S. application Ser. No. 14/693,207 (filed on Apr. 22, 2015 and granted as U.S. Pat. No. 11,154,183), which claims priority to U.S. Provisional Application No. 61/982,717).

The contents of all of the aforementioned related applications are hereby expressly incorporated by reference in their entirety, including the contents and teachings of any references contained therein.

BACKGROUND

The present disclosure relates generally to systems, devices, and methods, and more specifically, relates to systems, devices, and methods for use in performing procedures via a single incision or a natural orifice.

Conventional surgical procedures will generally require one or more large incisions to a patient in order for the surgical team to perform a surgical action. With the advancement of medical science and technology, most conventional open surgical procedures have been largely replaced with minimally invasive surgery (MIS) procedures. Recent developments in respect to computer-assisted and/or robotic surgical technology have contributed to advancements in MIS, including the ability to translate a surgeon's desired actions into movements of robotic instruments inside the body cavity of a patient.

BRIEF SUMMARY

Despite recent developments in modern medical science and technology, it is recognized in the present disclosure that one or more problems are encountered in modern surgical technology and methodology. For example, a typical MIS procedure requires multiple incisions to a patient in order to allow access via the incisions for the insertion of a camera and various other laparoscopic instruments into the body cavity of the patient.

As another example, surgical robotic devices oftentimes encounter difficulties during surgical procedures due to insufficient anchoring and/or reactive forces to stabilize against forces that are desired and/or necessary to be applied during surgical actions.

It is also recognized in the present disclosure that surgical robotic systems face difficulties in providing an instrument, such as a cutting or gripping instrument attached to the end of a surgical robotic arm, with access to all or even most parts, areas, and/or quadrants of abdominal cavity of a patient. That is, after the surgical robotic arm is inserted in the abdominal cavity of the patient and ready to perform a surgical action, the instrument attached to the end of the surgical robotic arm is typically limited to access only certain parts, areas, and quadrants of the abdominal cavity of the patient.

In yet another example, known surgical robotic systems typically provide only between one to two surgical robotic arms per access or opening (such as an incision or a natural orifice) of the patient. In this regard, one or more additional incisions will be required for the insertion of a camera and various laparoscopic instruments into the abdominal cavity of the patient.

As another example, while known surgical robotic systems have been designed for use in an abdominal cavity of a patient to perform forward-directed surgical procedures, such systems have not been designed for and may encounter problems when applied in situations requiring reverse-directed surgical procedures. For example, such known surgical robotic systems have not been designed for deployment through a natural orifice, such as a rectum or vagina, for performing natural orifice transluminal endoscopic surgery (or NOTES), such as pelvic gynecological and/or urological procedures. Such systems may encounter one or more problems, such as the inability to access certain organs, tissues, or other surgical sites upon insertion into the natural orifice.

Present example embodiments relate generally to systems, devices, and methods for addressing one or more problems in surgical robotic systems, devices, and methods, including those described above and herein.

In an exemplary embodiment, a surgical arm assembly is described. The surgical arm assembly includes an end-effector assembly. The end-effector assembly includes a first instrument for performing a surgical action. The surgical arm assembly also includes a first arm assembly having an elongated first arm assembly body, a proximal end, and distal end. The distal end of the first arm assembly is securable to the end-effector assembly. The surgical arm assembly also includes an elbow joint assembly. The elbow joint assembly includes a distal end and a proximal end. The distal end of the elbow joint assembly is secured to the proximal end of the first arm assembly. The proximal end of the elbow joint assembly is secured to a distal end of a second arm assembly. The surgical arm assembly includes the second arm assembly. The second arm assembly includes an elongated second arm assembly body. The second arm assembly also includes a first elbow drive assembly. The first elbow drive assembly is housed in the second arm assembly body. The first elbow drive assembly includes an integrated motor. The integrated motor of the first elbow drive assembly is configured to drive the elbow joint assembly to pivotally move the first arm assembly relative to a first axis. The second arm assembly also includes a second elbow drive assembly. The second elbow drive assembly is housed in the second arm assembly body. The second elbow drive assembly includes an integrated motor. The integrated motor of the second elbow drive assembly is configured to drive the elbow joint assembly to pivotally move the first arm assembly relative to a second axis.

In another exemplary embodiment, a surgical arm assembly is described. The surgical arm assembly includes an end-effector assembly. The end-effector assembly includes a first instrument for performing a surgical action. The surgical arm assembly also includes a first arm assembly having an elongated first arm assembly body, a proximal end, and distal end. The distal end of the first arm assembly is securable to the end-effector assembly. The surgical arm assembly also includes an elbow joint assembly. The elbow joint assembly includes a distal end and a proximal end. The distal end of the elbow joint assembly is secured to the proximal end of the first arm assembly. The proximal end of the elbow joint assembly is secured to a distal end of a second arm assembly. The surgical arm assembly also includes the second arm assembly. The second arm assembly includes an elongated second arm assembly body. The second arm assembly also includes a first elbow drive assembly. The first elbow drive assembly is housed in the second arm assembly body. The first elbow drive assembly includes an integrated motor. The integrated motor of the first elbow drive assembly is configured to drive the elbow joint assembly to pivotally move the first arm assembly relative to a first axis. The second arm assembly also includes a second elbow drive assembly. The second elbow drive assembly is housed in the second arm assembly body. The second elbow drive assembly includes an integrated motor. The integrated motor of the second elbow drive assembly is configured to drive the elbow joint assembly to pivotally move the first arm assembly relative to a second axis. The second arm assembly also includes a first shoulder drive assembly. The first shoulder drive assembly is housed in the second arm assembly body. The first shoulder drive assembly includes an integrated motor. The integrated motor of the first shoulder drive assembly is configured to drive a shoulder joint assembly to pivotally move the second arm assembly relative to a third axis. The surgical arm assembly also includes the shoulder joint assembly. The shoulder joint assembly includes a distal end and a proximal end. The distal end of the shoulder joint assembly is secured to a proximal end of the second arm assembly. The proximal end of the shoulder joint assembly is secured to a distal end of a shoulder section. The surgical arm assembly also includes the shoulder section.

In another exemplary embodiment, a surgical arm assembly is described. The surgical arm assembly includes an end-effector assembly. The end-effector assembly includes a first instrument for performing a surgical action. The surgical arm assembly also includes a first arm assembly having an elongated first arm assembly body, a proximal end, and distal end. The distal end of the first arm assembly is securable to the end-effector assembly. The surgical arm assembly also includes an elbow joint assembly. The elbow joint assembly includes a distal end and a proximal end. The distal end of the elbow joint assembly is secured to the proximal end of the first arm assembly. The proximal end of the elbow joint assembly is secured to a distal end of a second arm assembly. The surgical arm assembly also includes the second arm assembly. The second arm assembly includes an elongated second arm assembly body. The second arm assembly also includes a first elbow drive assembly. The first elbow drive assembly is housed in the second arm assembly body. The first elbow drive assembly includes an integrated motor. The integrated motor of the first elbow drive assembly is configured to drive the elbow joint assembly to pivotally move the first arm assembly relative to a first axis. The second arm assembly also includes a second elbow drive assembly. The second elbow drive assembly is housed in the second arm assembly body. The second elbow drive assembly includes an integrated motor. The integrated motor of the second elbow drive assembly is configured to drive the elbow joint assembly to pivotally move the first arm assembly relative to a second axis. The second arm assembly also includes a first shoulder drive assembly. The first shoulder drive assembly is housed in the second arm assembly body. The first shoulder drive assembly includes an integrated motor. The integrated motor of the first shoulder drive assembly is configured to drive a shoulder joint assembly to pivotally move the second arm assembly relative to a third axis. The second arm assembly also includes a second shoulder drive assembly. The second shoulder drive assembly is housed in the second arm assembly body. The second shoulder drive assembly includes an integrated motor. The integrated motor of the second shoulder drive assembly is configured to drive the shoulder joint assembly to pivotally move the second arm assembly relative to a fourth axis. The surgical arm assembly also includes the shoulder joint assembly. The shoulder joint assembly includes a distal end and a proximal end. The distal end of the shoulder joint assembly is secured to a proximal end of the second arm assembly. The proximal end of the shoulder joint assembly is secured to a distal end of a shoulder section. The surgical arm assembly also includes the shoulder section.

In another exemplary embodiment, a surgical system is described. The system may include a first arm assembly having a first arm assembly body. The system may also include a distal elbow joint assembly secured to a proximal end of the first arm assembly. The distal elbow joint assembly may be configurable to provide the first arm assembly with a first degree of freedom relative to a first axis. The system may also include a proximal elbow joint assembly secured to the distal elbow joint assembly. The proximal elbow joint assembly may be configurable to provide the first arm assembly with a second degree of freedom relative to a second axis. The second axis may be different from the first axis. The first degree of freedom may be different from the second degree of freedom.

In another exemplary embodiment, a surgical system is described. The system may include a first arm assembly having a first arm assembly body. The first arm assembly body may include an elbow drive assembly. The system may also include an elbow joint assembly secured to a proximal end of the first arm assembly. The elbow joint assembly may be configured to be controllable by the elbow drive assembly of the first arm assembly to provide the first arm assembly with a first degree of freedom relative to a first axis.

In another exemplary embodiment, a surgical system is described. The system may include a first arm assembly having a first arm assembly body. The system may also include a second arm assembly having a second arm assembly body. The system may also include a multi-joint elbow joint assembly securing a proximal end of the first arm assembly to a distal end of the second arm assembly. The multi-joint elbow joint assembly may include a first joint and a second joint. The first joint may be configurable to control a movement of the first arm assembly relative to a first axis. The second joint may be configurable to control a movement of the first arm assembly relative to a second axis. The second axis may be different from the first axis.

In another exemplary embodiment, a surgical system is described. The system may include an end-effector assembly having a first instrument for performing a surgical action. The system may include a first arm assembly having an elongated first arm assembly body, a proximal end, and a distal end. The distal end of the first arm assembly may be securable to the end-effector assembly. The system may include an elbow joint assembly configurable to secure the proximal end of the first arm assembly to a distal end of a second arm assembly. The elbow joint assembly may include a serially connected arrangement of a first elbow joint portion and second elbow joint portion. The first elbow joint portion may include a first end section secured to the proximal end of the first arm assembly. The first elbow joint portion may also include a second end section. The first elbow joint portion may also include a first elongated joint joining the first and second end sections of the first elbow joint portion. The first end section of the first elbow joint portion may be pivotable relative a first axis formed by a center line drawn through the first elongated joint. The second elbow joint portion may include a first end section secured to the second end section of the first elbow joint portion. The second elbow joint portion may also include a second end section secured to the distal end of the second arm assembly. The second elbow joint portion may also include a second elongated joint joining the first and second end sections of the second elbow joint portion. The first end section of the second elbow joint portion may be pivotable relative to a second axis formed by a center line drawn through the second elongated joint.

In another exemplary embodiment, a surgical system for use in performing an in vivo surgical procedure is described. The system may include an end-effector assembly having a first instrument for performing a surgical action. The system may also include a first arm assembly having an elongated first arm assembly body, a proximal end, and distal end. The distal end of the first arm assembly may be securable to the end-effector assembly. The system may also include an elbow joint assembly configured to secure the proximal end of the first arm assembly to a distal end of a second arm assembly. The elbow joint assembly may include a serially connected arrangement of a first elbow joint portion and second elbow joint portion. The first elbow joint portion may be for enabling the first arm assembly to pivot relative to a first axis. The second elbow joint portion may be secured to the first elbow joint portion. The second elbow joint portion may be for enabling the first arm assembly to pivot relative to a second axis. The second axis may be different from the first axis. The second arm assembly may include an elongated second arm assembly body, a first elbow drive assembly, and a second elbow drive assembly. The first elbow drive assembly may be housed in the second arm assembly body. The first elbow drive assembly may include a first integrated motor configurable to drive the first elbow joint portion to pivot the first arm assembly relative to the first axis. The second elbow drive assembly may be housed in the second arm assembly body. The second elbow drive assembly may include a second integrated motor configurable to drive the second elbow joint portion to pivot the first arm assembly relative to the second axis.

In another exemplary embodiment, a surgical system for use in performing an in vivo surgical procedure is described. The system may include an end-effector assembly having a first instrument for performing a surgical action. The system may also include a first arm assembly having an elongated first arm assembly body, a proximal end, and distal end. The distal end of the first arm assembly may be securable to the end-effector assembly. The system may also include an elbow joint assembly configured to secure the proximal end of the first arm assembly to a distal end of a second arm assembly. The elbow joint assembly may include a serially connected arrangement of a first elbow joint portion and second elbow joint portion. The first elbow joint portion may be for enabling the first arm assembly to pivot relative to a first axis. The second elbow joint portion may be for enabling the first arm assembly to pivot relative to a second axis. The second axis may be different from the first axis. The system may also include the second arm assembly. The system may also include a shoulder joint assembly configured to secure a proximal end of the second arm assembly to a shoulder section. The shoulder joint assembly may include a serially connected arrangement of a first shoulder joint portion and a second shoulder joint portion. The system may also include the shoulder section at a proximal end of the system.

In another exemplary embodiment, a surgical system for use in performing an in vivo surgical procedure is described. The system may include an end-effector assembly, a first arm assembly, and a second arm assembly. The end-effector assembly may be provided at a distal end of the surgical system. The end-effector assembly may include a serially connected arrangement of an instrument assembly and a wrist assembly. The instrument assembly may include a first instrument for performing a surgical action. The first arm assembly may be securable at a first end to the wrist assembly. The first arm assembly may include an elongated first arm assembly body. The first arm assembly may also include a first instrument drive assembly housed in the first arm assembly body. The first instrument drive assembly may include a first integrated motor configurable to pivotally move the first instrument relative to a first axis. The first arm assembly may also include a second instrument drive assembly housed in the first arm assembly body. The first arm assembly may also include a wrist drive assembly housed in the first arm assembly body. The wrist drive assembly may include a second integrated motor configurable to pivotally move the instrument assembly relative a second axis. The second axis may be different from the first axis. The first arm assembly may also include a first arm assembly drive assembly housed in the first arm assembly body. The first arm assembly drive assembly may include a third integrated motor configurable to rotate at least the end-effector assembly relative to a third axis. The third axis may be formed by a center line drawn through the first arm assembly body. The elbow joint assembly may be configured to secure a second end of the first arm assembly to a first end of a second arm assembly. The elbow joint assembly may include a serially connected arrangement of an elbow pitch joint portion and elbow sway joint portion. The elbow pitch joint portion may be configurable to be driven to pivotally move the first arm assembly relative to a fourth axis. The elbow sway joint portion may be configurable to be driven to pivotally move the first arm assembly relative to a fifth axis. The fifth axis may be different from the fourth axis. The second arm assembly may include an elongated second arm assembly body. The second arm assembly may also include an elbow pitch drive assembly housed in the second arm assembly body. The elbow pitch drive assembly may include a fourth integrated motor configurable to drive the elbow pitch joint portion to pivotally move the first arm assembly relative to the fourth axis. The second arm assembly may also include an elbow sway drive assembly housed in the second arm assembly body. The elbow sway drive assembly may include a fifth integrated motor configurable to drive the elbow sway joint portion to pivotally move the first arm assembly relative to the fifth axis.

In an exemplary embodiment, a surgical system for use in performing an in vivo surgical procedure is described. The system may include an end-effector assembly, a first arm assembly, an elbow pitch joint portion, an elbow sway joint portion, and a second arm assembly. The end-effector assembly may be provided at a distal end of the surgical system. The end-effector assembly may include a serially connected arrangement of an instrument assembly and a wrist assembly. The instrument assembly may include a first instrument for performing a surgical action. The first arm assembly may be securable at a first end to the wrist assembly. The first arm assembly may include an elongated first arm assembly body. The first arm assembly may also include a first instrument drive assembly housed in the first arm assembly body. The first instrument drive assembly may include a first integrated motor configurable to pivotally move the first instrument relative to a first axis. The first arm assembly may also include a second instrument drive assembly housed in the first arm assembly body. The first arm assembly may also include a wrist drive assembly housed in the first arm assembly body. The wrist drive assembly may include a second integrated motor configurable to pivotally move the instrument assembly relative a second axis. The second axis may be different from the first axis. The first arm assembly may also include a first arm assembly drive assembly housed in the first arm assembly body. The first arm assembly drive assembly may include a third integrated motor configurable to rotate at least the end-effector assembly relative to a third axis. The third axis may be formed by a center line drawn through the first arm assembly body. The elbow pitch joint portion may be configured to secure a second end of the first arm assembly to an elbow sway joint portion. The elbow pitch joint portion may be configurable to be driven to pivotally move the first arm assembly relative to the elbow sway joint portion. The elbow sway joint portion may be configured to secure the elbow pitch joint portion to a first end of a second arm assembly. The elbow sway joint portion may be configurable to be driven to pivotally move the elbow pitch joint portion relative to the second arm assembly.

In an exemplary embodiment, a surgical system for use in performing an in vivo surgical procedure is described. The system may include an end-effector assembly, a first arm assembly, an elbow joint assembly, a second arm assembly, and a shoulder joint assembly. The end-effector assembly may be provided at a distal end of the surgical system. The end-effector assembly may include a serially connected arrangement of an instrument assembly and a wrist assembly. The instrument assembly may include a first instrument for performing a surgical action. The first arm assembly may be securable at a first end to the wrist assembly. The first arm assembly may include an elongated first arm assembly body. The first arm assembly may also include a first instrument drive assembly housed in the first arm assembly body. The first instrument drive assembly may include a first integrated motor configurable to pivotally move the first instrument relative to a first axis. The first arm assembly may also include a second instrument drive assembly housed in the first arm assembly body. The first arm assembly may also include a wrist drive assembly housed in the first arm assembly body. The wrist drive assembly may include a second integrated motor configurable to pivotally move the instrument assembly relative a second axis. The second axis may be different from the first axis. The first arm assembly may also include a first arm assembly drive assembly housed in the first arm assembly body. The first arm assembly drive assembly may include a third integrated motor configurable to rotate at least the end-effector assembly relative to a third axis. The third axis may be formed by a center line drawn through the first arm assembly body. The elbow joint assembly may be configured to secure a second end of the first arm assembly to a first end of a second arm assembly. The elbow joint assembly may include a serially connected arrangement of an elbow pitch joint portion and elbow sway joint portion. The elbow pitch joint portion may be configurable to pivotally move the first arm assembly relative to a fourth axis. The elbow sway joint portion may be configurable to pivotally move the first arm assembly relative to a fifth axis. The fifth axis may be different from the fourth axis. The second arm assembly may include an elongated second arm assembly body. The second arm assembly may also include an elbow pitch drive assembly housed in the second arm assembly body. The elbow pitch drive assembly may include a fourth integrated motor configurable to drive the elbow pitch joint portion to pivotally move the first arm assembly relative to the fourth axis. The second arm assembly may also include an elbow sway drive assembly housed in the second arm assembly body. The elbow sway drive assembly may include a fifth integrated motor configurable to drive the elbow sway joint portion to pivotally move the first arm assembly relative to the fifth axis. The second arm assembly may also include a shoulder pitch drive assembly housed in the second arm assembly body. The shoulder pitch drive assembly may include a sixth integrated motor configurable to drive a shoulder pitch joint portion to pivotally move the second arm assembly relative to a sixth axis. The second arm assembly may also include a shoulder sway drive assembly housed in the second arm assembly body. The shoulder sway drive assembly may include an seventh integrated motor configurable to drive a shoulder sway joint portion to pivotally move the second arm assembly relative to a seventh axis. The seventh axis may be different from the sixth axis. The shoulder joint assembly may be configured to secure a second end of the second arm assembly to a shoulder section. The shoulder joint assembly may include a serially connected arrangement of a shoulder pitch joint portion and shoulder sway joint portion. The shoulder pitch joint portion may be configurable to pivotally move the second arm assembly relative to the sixth axis. The shoulder sway joint portion may be configurable to pivotally move the second arm assembly relative to the seventh axis. The shoulder section may be provided at a proximal end of the surgical system.

In another exemplary embodiment, a surgical system is described. The surgical system may include a first arm assembly. The first arm assembly may include a first arm assembly body. The surgical system may also include a distal elbow joint assembly secured to a proximal end of the first arm assembly. The distal elbow joint assembly may be configured to provide the first arm assembly with a first degree of freedom relative to a first axis. The surgical system may also include a proximal elbow joint assembly secured to the distal elbow joint assembly. The proximal elbow joint assembly may be configured to provide the first arm assembly with a second degree of freedom relative to a second axis. The second axis may be different from the first axis. The first degree of freedom may be different from the second degree of freedom.

In another exemplary embodiment, a surgical system is described. The surgical system may include a first arm assembly. The first arm assembly may include a first arm assembly body. The first arm assembly body may include an elbow drive assembly. The surgical system may also include an elbow joint assembly. The elbow joint assembly may be secured to a proximal end of the first arm assembly. The elbow joint assembly may be configured to be controllable by the elbow drive assembly of the first arm assembly to provide the first arm assembly with a first degree of freedom relative to a first axis.

In another exemplary embodiment, a surgical system is described. The surgical system may include a first arm assembly. The first arm assembly may include a first arm assembly body. The surgical system may also include a second arm assembly. The second arm assembly may include a second arm assembly body. The surgical system may also include a multi-joint elbow joint assembly. The multi-joint elbow joint assembly may be configured to secure a proximal end of the first arm assembly to a distal end of the second arm assembly. The multi-joint elbow joint assembly may include a first joint and a second joint. The first joint may be configurable to control a movement of the first arm assembly relative to a first axis. The second joint may be configurable to control a movement of the first arm assembly relative to a second axis. The second axis may be different from the first axis.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 4B is an illustration of a side view of an example embodiment of a port assembly;

FIG. 4C is an illustration of a cross-sectional view of an example embodiment of a port assembly with a first or second gate assembly in the open position;

FIG. 4D is an illustration of a cross-sectional view of an example embodiment of a port assembly with a first or second gate assembly in the closed position;

FIG. 5D is an illustration of a side view of an example embodiment of an end-effector assembly secured to an arm assembly;

FIG. 5E is an illustration of a side cross-sectional view of an example embodiment of an end-effector assembly secured to an arm assembly;

FIG. 5P is another illustration of a side view of an example embodiment of an instrument arm assembly;

FIG. 5Q is another illustration of a side view of an example embodiment of an instrument arm assembly;

FIG. 5R is another illustration of a perspective view of an example embodiment of an instrument arm assembly;

FIG. 5S is another illustration of a side view of an example embodiment of an instrument arm assembly;

FIG. 5T is another illustration of a side cross-sectional view of an example embodiment of an instrument arm assembly;

FIG. 5U is another illustration of a top cross-sectional view of an example embodiment of a second arm assembly;

FIG. 5V is another illustration of a transparent perspective partial view of an example embodiment of an instrument arm assembly;

Although similar reference numbers may be used to refer to similar elements in the figures for convenience, it can be appreciated that each of the various example embodiments may be considered to be distinct variations.

DETAILED DESCRIPTION

Figure 1A:
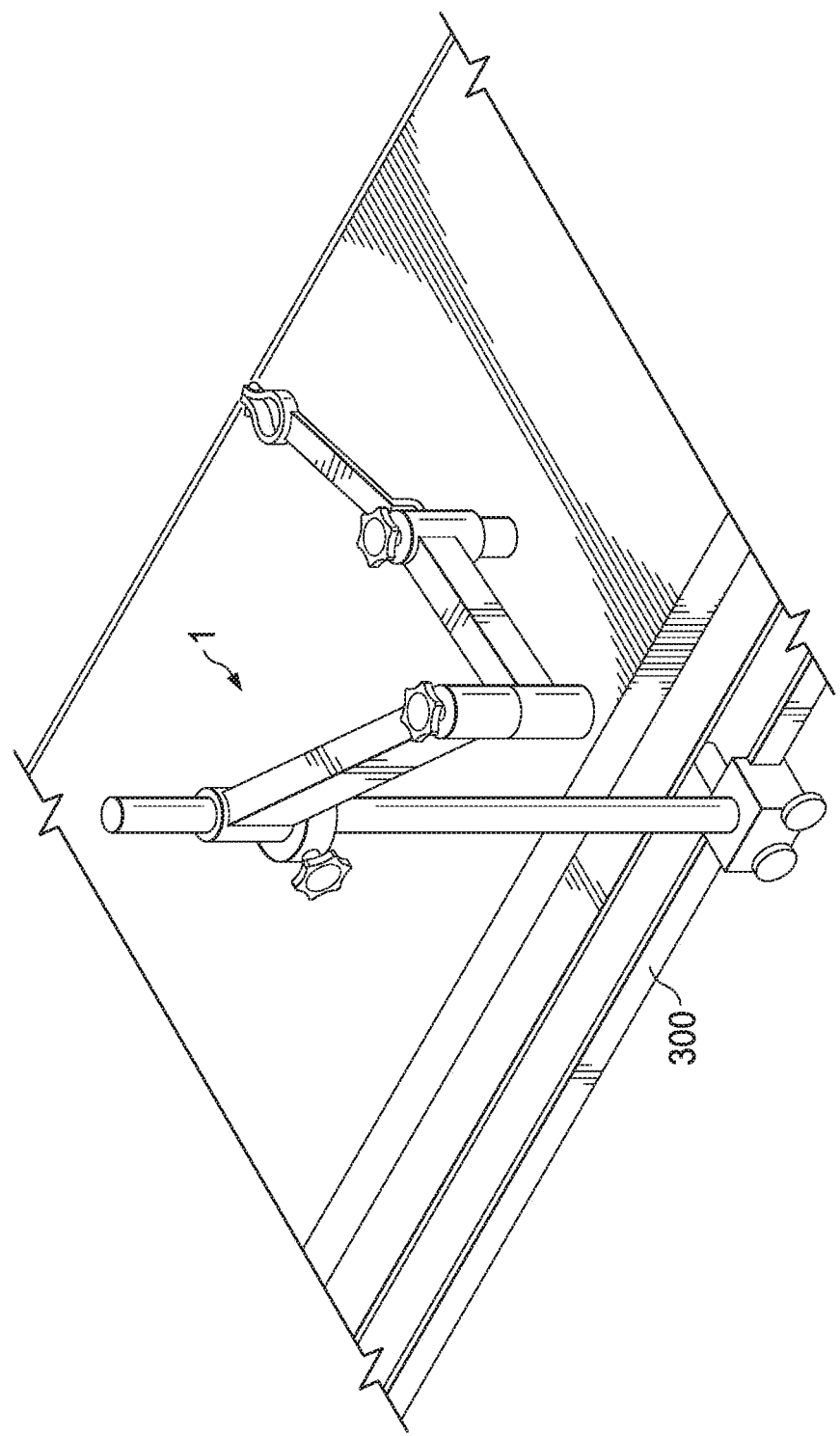
FIG. 1A is illustration of a perspective view of an example embodiment of an external anchor.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

It is recognized in the present disclosure that, despite recent developments in medical science and technology, one or more problems are encountered in modern surgical technology and methodology, including MIS. For example, a typical MIS procedure requires multiple incisions to a patient in order to allow access via the incisions for the insertion of a camera and various other laparoscopic instruments into the body cavity of the patient.

In addition to the aforementioned disadvantages pertaining to the multiple and rather large incisions, it is recognized in the present disclosure that surgical robotic systems, including surgical robotic arms (and those instruments attached to them), developed for performing robotic-assisted MIS surgical procedures also suffer from one or more problems. For example, it is recognized herein that a major technical challenge for a surgical robotic system is the difficulty in providing sufficient anchoring and/or reactive forces to stabilize against forces that are desired and/or necessary to be applied to the patient by the surgical robotic system during a surgical action. In this regard, certain surgical actions for known surgical robotic systems may require tremendous effort and time, and may not be performed properly or at all as a result of the problem of insufficient anchoring and/or reactive forces.

Another example of a problem recognized in the present disclosure as being encountered by surgical robotic systems is the difficulty in providing an instrument, such as a cutting and/or gripping instrument attached to the end of a surgical robotic arm, with access to all or even most parts, areas, and quadrants of an abdominal cavity of a patient after the surgical robotic system has been set up (or installed) and is ready to perform a surgery. That is, after the surgical robotic arm of the system has been inserted, attached, and properly set up in the abdominal cavity of the patient and is ready to perform a surgical action, the instrument attached to the end of the surgical robotic arm is typically limited to access only certain parts, areas, and quadrants of the abdominal cavity of the patient. It is recognized in the present disclosure that such problems result in large from the limited number of possible degrees of freedom that can be provided by known surgical robotic systems and arms, and more specifically, the limited number of in vivo degrees of freedom (i.e. the degrees of freedom provided within an abdominal cavity of a patient) of known surgical robotic systems and arms. In this regard, surgical robotic systems typically provide only between 2 to 4 in vivo degrees of freedom for each surgical robotic arm.

As another example, while known surgical robotic systems have been designed for use in an abdominal cavity of a patient to perform forward-directed surgical procedures, such systems have not been designed for and may encounter problems when applied in situations requiring reverse-directed surgical procedures. For example, such known surgical robotic systems have not been designed for deployment through a natural orifice, such as a rectum or vagina, for performing natural orifice transluminal endoscopic surgery (or NOTES), such as trans-vaginal gynecological procedures in women and trans-rectal urological procedures in men. Such systems may encounter one or more problems, such as the inability to access certain organs, tissues, or other surgical sites upon insertion into the natural orifice.

Surgical systems, devices, and methods, including those for use in MIS and natural orifice transluminal endoscopic surgery (or NOTES), are described in the present disclosure for addressing one or more problems of known surgical systems, devices, and methods, including those described above and in the present disclosure. It is to be understood that the principles described in the present disclosure can be applied outside of the context of MIS and/or NOTES, such as performing scientific experiments and/or procedures in environments that are not readily accessible by humans, including in a vacuum, in outer space, and/or under toxic and/or dangerous conditions, without departing from the teachings of the present disclosure.

The Surgical System (e.g., Surgical Device 200)

An illustration of an example embodiment of a surgical device or system (e.g., surgical device or system 200) operable to be inserted into an abdominal cavity of a patient through a single access or opening (e.g., a single incision (such as an incision in or around the umbilical area) or through a natural orifice (such as a rectum or vagina, for performing natural orifice transluminal endoscopic surgery (or NOTES), hereinafter referred to as an "opening") of the patient is depicted in FIG. 2A, FIG. 2B, FIG. 2C, and FIG. 2D. The surgical device may then be anchored so as to position the surgical device 200 in the opening. The surgical device 200 may comprise a port assembly 210 and an instrument arm assembly 230. The surgical device 200 may also comprise other elements, such as one or more other instrument arm assemblies (e.g., instrument arm assembly 240), one or more image capturing assemblies, one or more assistant arm assemblies, etc.

Figure 1B:
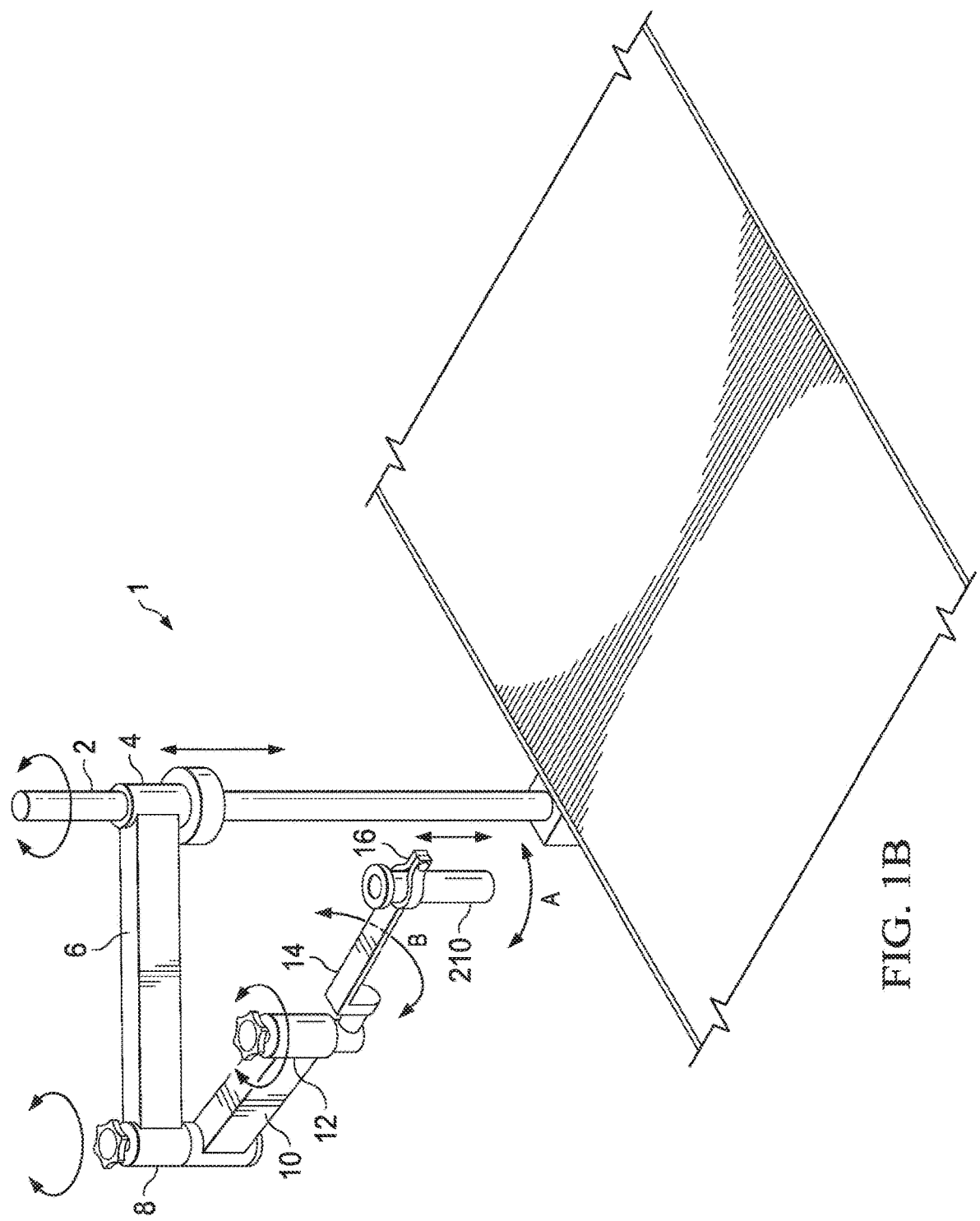
FIG. 1B is another illustration of a perspective view of an example embodiment of an external anchor attached to an example embodiment of a port assembly.
Figure 10A:
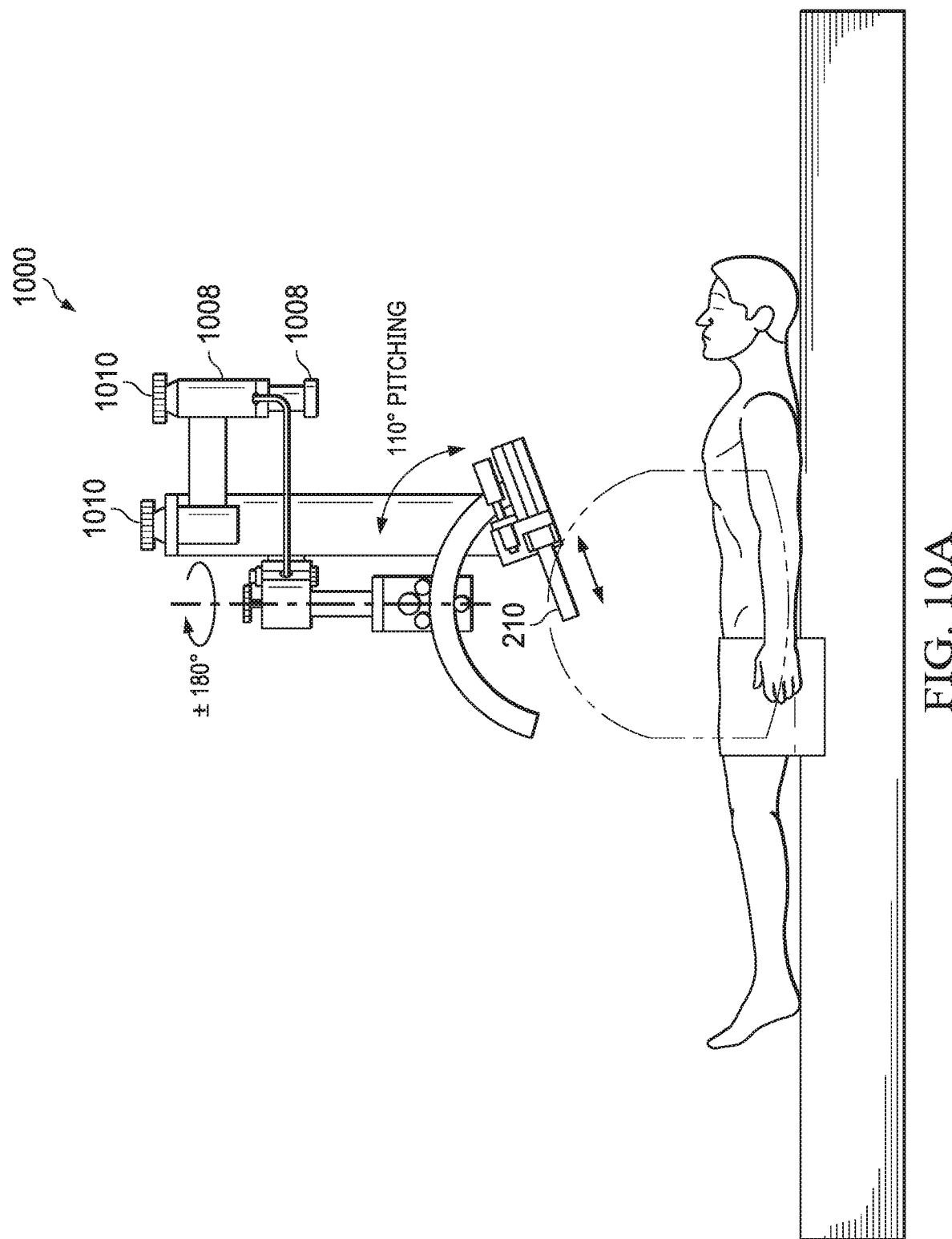
FIG. 10A is an illustration of a perspective view of an example embodiment of an external anchor.
Figure 10B:
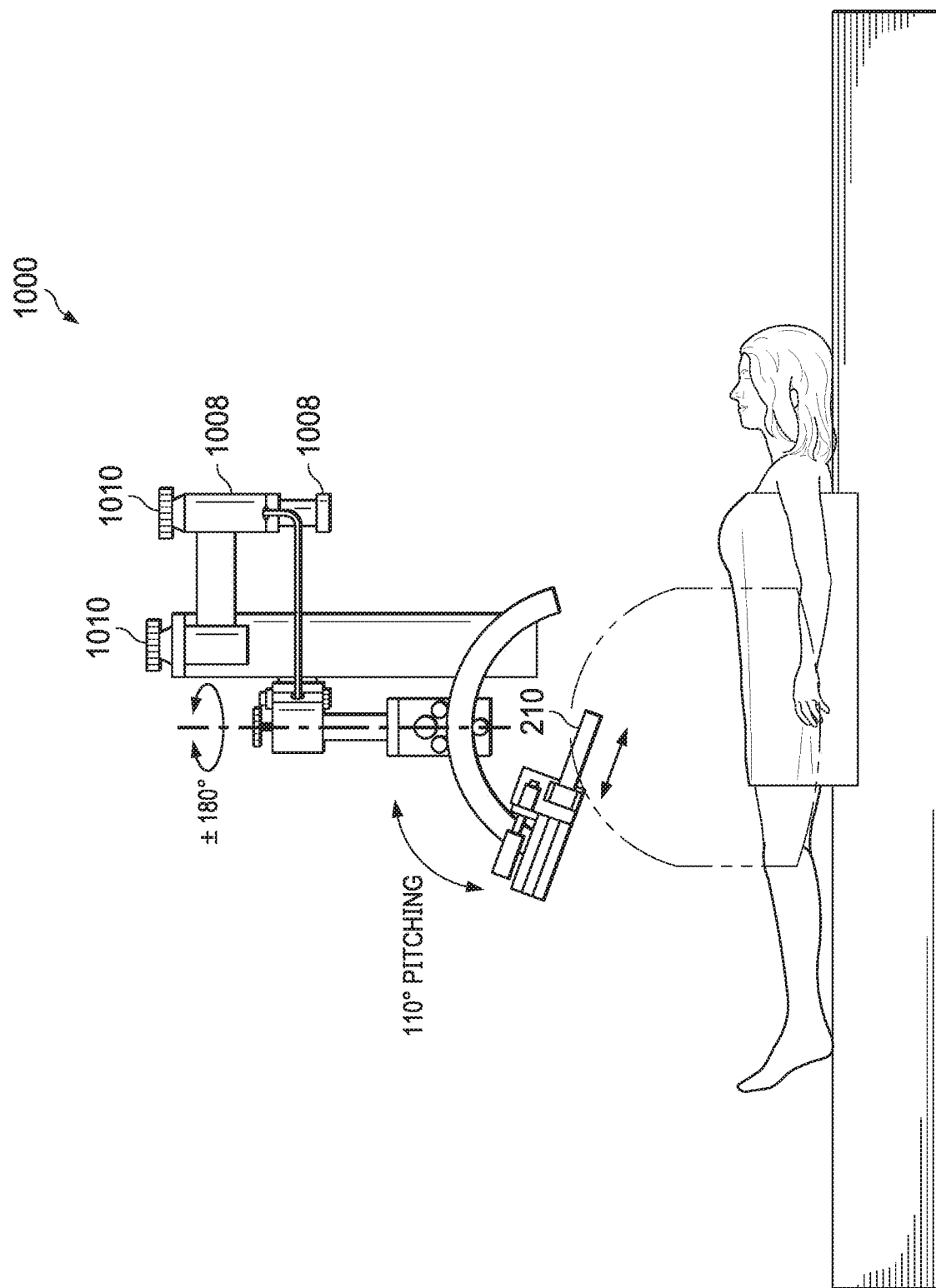
FIG. 10B is an illustration of a perspective view of another example embodiment of an external anchor.

As illustrated in FIG. 1A and FIG. 1B, the surgical device 200 may be provided with an external anchor 1 attachable to the port assembly 210. The external anchor 1 may comprise a configurable assembly of segments 2, 6, 10, and 14 in communication with one another via joints or connecting portions 4, 8, and 12, and external anchor connector 16. The external anchor 1 may be operable to securely fix the position and/or orientation (hereinafter "position") of the port assembly 210 in or about the single opening of the patient, and may also be operable to provide sufficient anchoring and/or reactive forces to stabilize against forces desired and/or necessary to be applied by at least one or more elements of the surgical device 200, including the instrument arm assembly 230, during a surgical action or procedure. The external anchor 1, which may also be in the form of the controllable swivel assembly 1000 illustrated in FIG. 10A and FIG. 10B, may be operable to cooperate with the port assembly 210 to provide one or more in vitro degrees of freedom. For example, the external anchor 1 may be configurable to provide 3 in vitro degrees of freedom. In example embodiments, the one or more in vitro degrees of freedom may include a torsional movement, pivotal movement, telescopic movement, and/or other movements of the port assembly 210 relative to the external anchor 1. For example, a torsional movement of the port assembly 210, as illustrated by arrow A in FIG. 1B, may allow one or more attached instruments, including an instrument arm assembly 230, to re-position during a surgical procedure (i.e. after set up or installation) so as to access other parts, areas, and/or all quadrants of the abdominal cavity of the patient. As another example, a pivotal movement of the port assembly 210, as illustrated by arrow B in FIG. 1B, may allow the port assembly 210 to be positioned in one of a plurality of angles with respect to opening of the patient, and may also allow attached instruments, including the instrument arm assembly 230, to re-position during a surgical procedure (i.e. after set up or installation) so as to access distal areas of the abdominal cavity of the patient. The other joint portions of the external anchor 1 may also be operable to cooperate and/or assist in desired movements of the port assembly 210. The external anchor 1 may be anchored to one or more stationary or fixedly positioned objects, such as a side rail 300 of a surgical table/bed illustrated in FIG. 1A. FIGS. 10A and 10B illustrate other example movements that provide for additional in vitro degrees of freedom via an example embodiment of the external anchor (controllable swivel assembly) 1000. The controllable swivel assembly 1000 will be further described below in at least the section "(1) Providing the external anchor and installing the port assembly."

The surgical device 200 may further comprise one or more additional instrument arm assemblies, such as a second instrument arm assembly 240 illustrated in FIG. 3A, FIG. 3B, FIG. 3C, and FIG. 3D, attachable to the port assembly 210. One or more of the instrument arm assemblies, including the first instrument arm assembly 230, the second instrument arm assembly 240, a third instrument arm assembly (not shown), a fourth instrument arm assembly (not shown), etc., may be attachable or securable to the port assembly 210. Such instrument arm assemblies may be operable to access and perform one or more surgical actions in/on any and all parts, areas, and/or quadrants within a cavity of the patient. For example, surgical device 200 may be configurable to perform surgical actions in a forward direction (or "forward-directed position" or "forward position") (e.g., as illustrated in FIGS. 2B, 2D, 3B, and 3D). As another example, surgical device 200 may be configurable to perform surgical actions in a reverse direction (or "reverse-directed position" or "reverse position") (e.g., as illustrated in FIGS. 2A, 2C, 3A, and 3C).

The surgical device 200 may also comprise one or more image capturing assemblies, such as image capturing assembly 220. The surgical device 200 may further comprise one or more assistant arm assemblies, such as a retractor arm assembly 260, as illustrated in FIGS. 2A, 2B, 3A, and 3B. Furthermore, the surgical device 200 may comprise one or more other instrument arm assemblies, such as suction/irrigation assembly 250, illustrated in FIGS. 2A, 2B, 3A, and 3B, that can be inserted into the opening of the patient via the port assembly 210 before, during, and/or after performing a surgical action or procedure. It is to be understood in the present disclosure that the surgical device 200 may be configurable in a plurality of configurations and arrangements, including having more or less than two instrument arm assemblies (such as third, fourth, fifth, etc. instrument arm assemblies), more than one image capturing assembly (such as second, third, etc. image capturing assemblies), more or less than one assistant arm assembly (such as second, third, etc. assistant arm assemblies), and/or more or less than one other laparoscopic tool in example embodiments without departing from the teachings of the present disclosure.

The Port Assembly (e.g., Port Assembly 210)

An example embodiment of the port assembly (e.g., port assembly 210) is illustrated in FIGS. 2A-D, 3A-D, FIG. 4A, FIG. 4B, FIG. 4C, and FIG. 4D. The port assembly 210 may be configurable to be inserted in or about a single opening of the patient (such as a single incision or a natural orifice) and fixed in position by at least the external anchor (such as the external anchor 1 illustrated in FIGS. 1A and 1B and the controllable swivel assembly 1000 illustrated in FIGS. 10A and 10B).

Figure 2A:
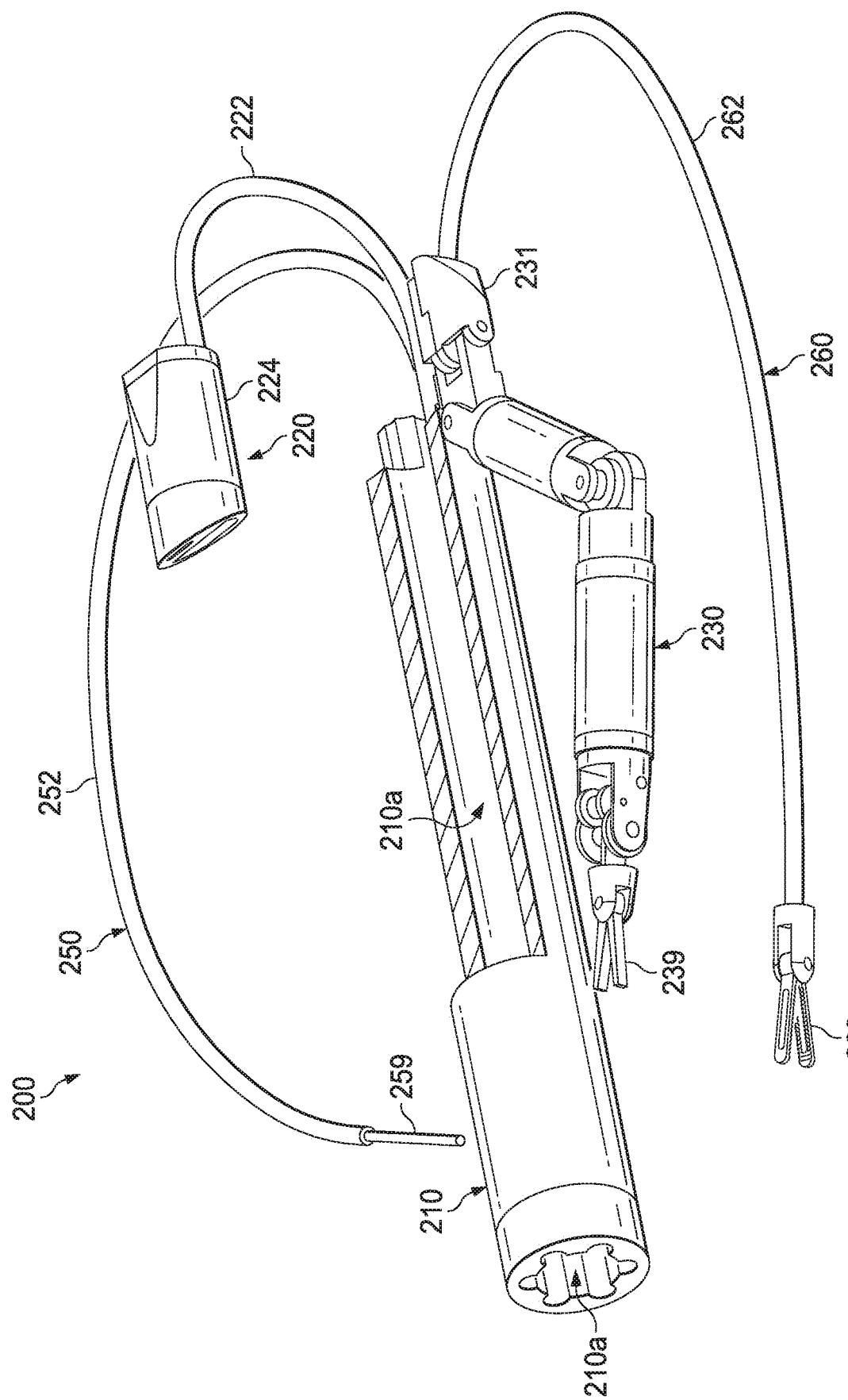
FIG. 2A is an illustration of a perspective view of an example embodiment of a surgical device configured in a reverse-directed position.
Figure 3A:
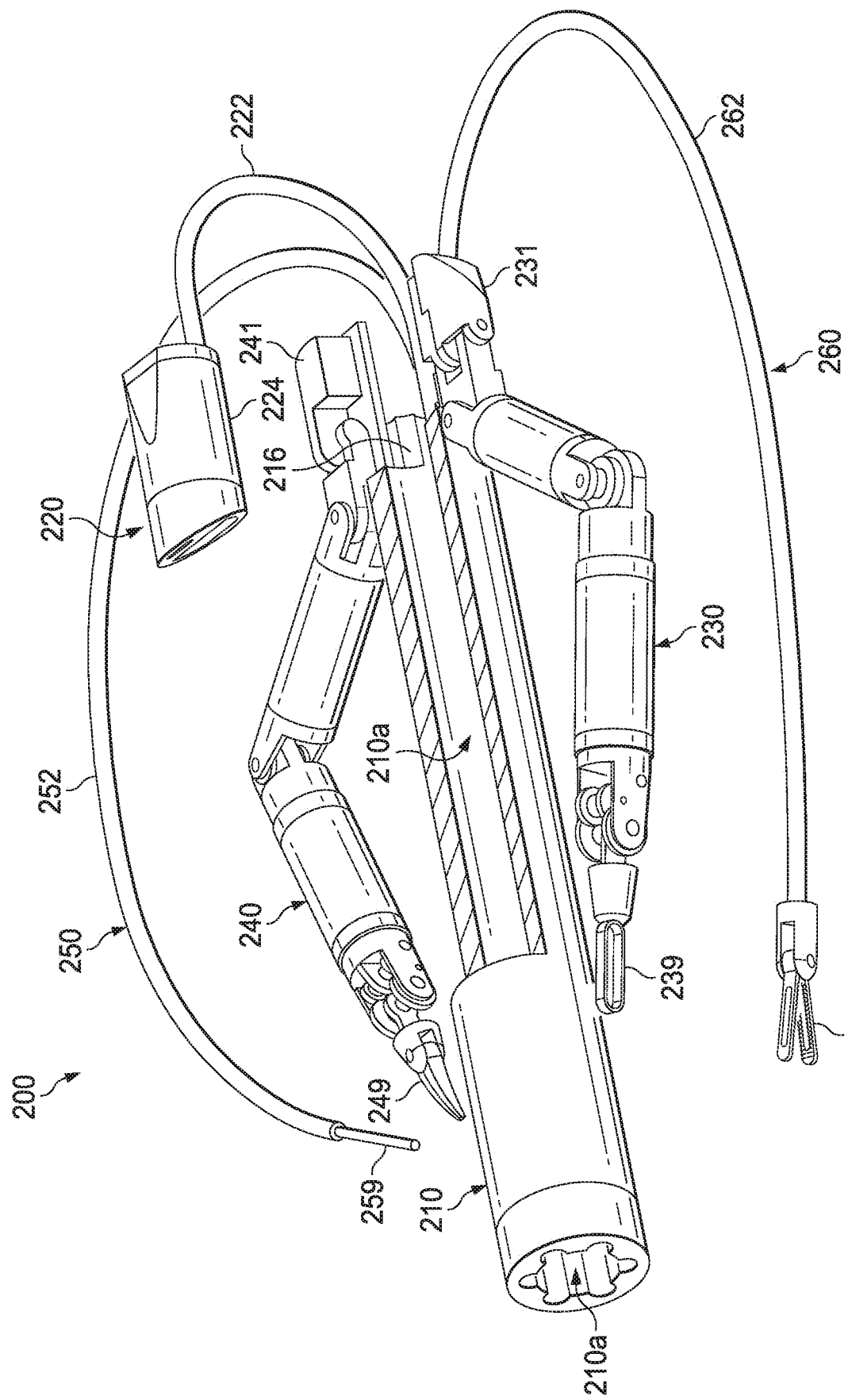
FIG. 3A is another illustration of a perspective view of an example embodiment of a surgical device configured in a reverse-directed position.
Figure 3B:
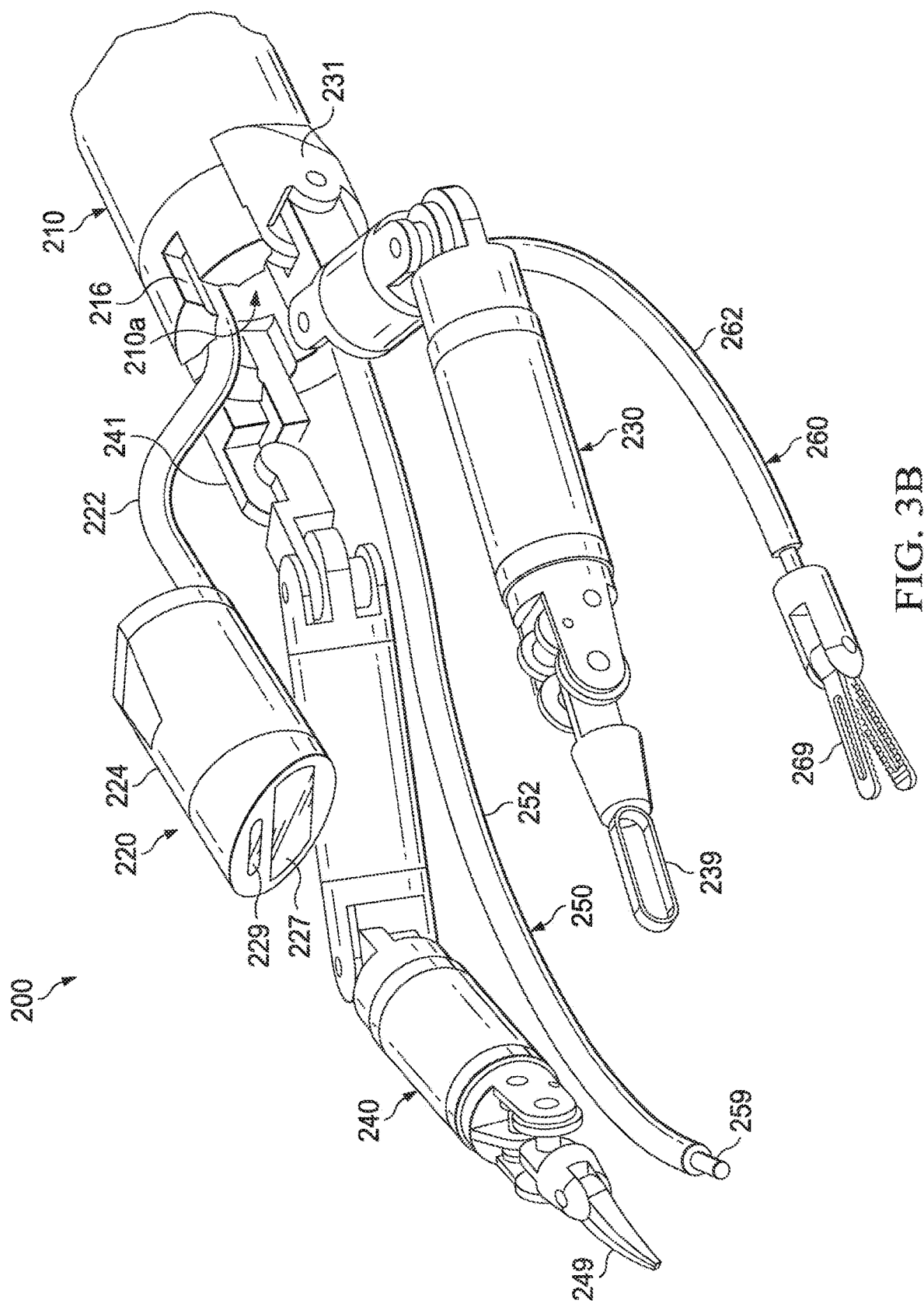
FIG. 3B is another illustration of a perspective view of an example embodiment of a surgical device configured in a forward-directed position.
Figure 3C:
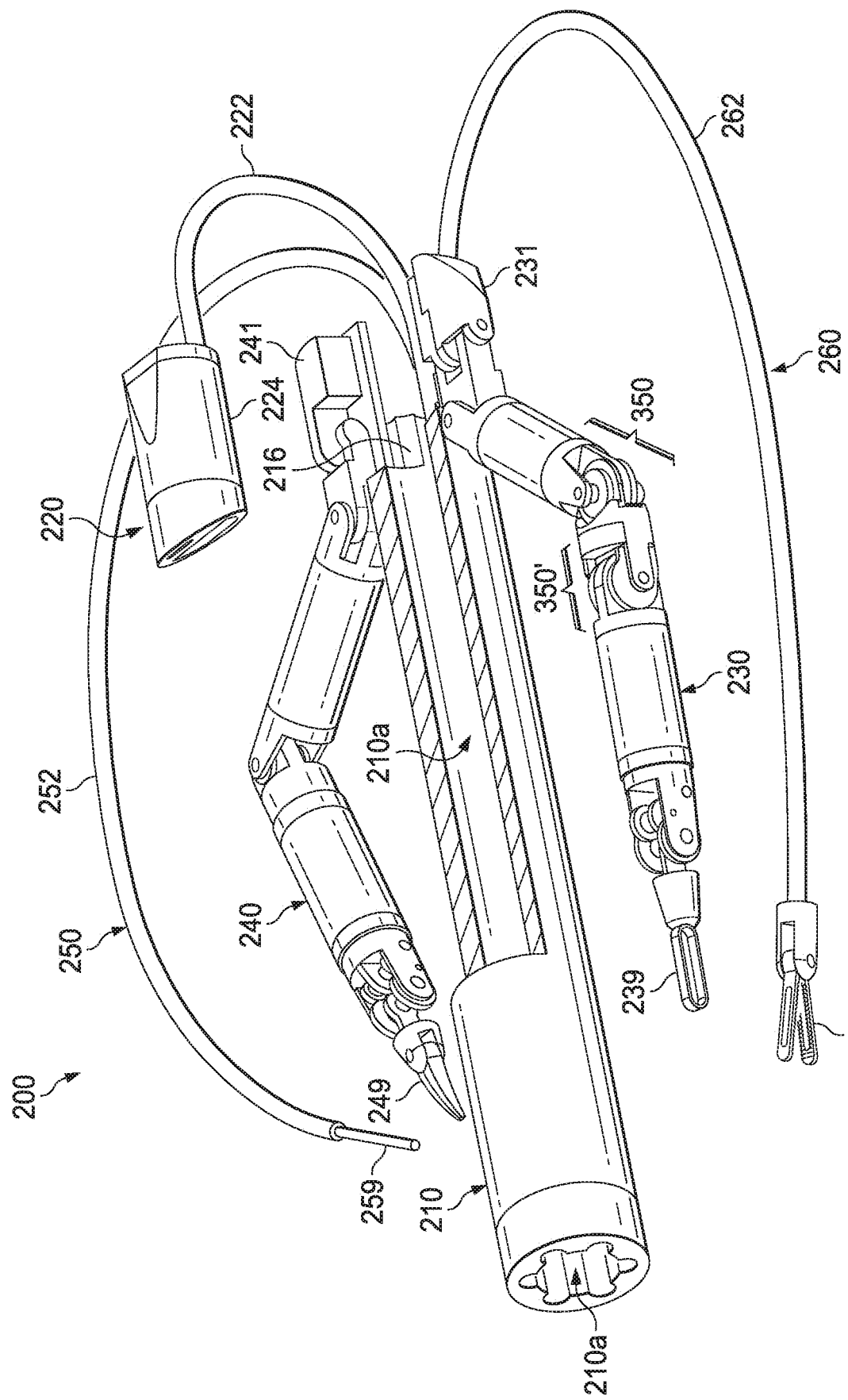
FIG. 3C is another illustration of a perspective view of an example embodiment of a surgical device configured in a reverse-directed position.
Figure 3D:
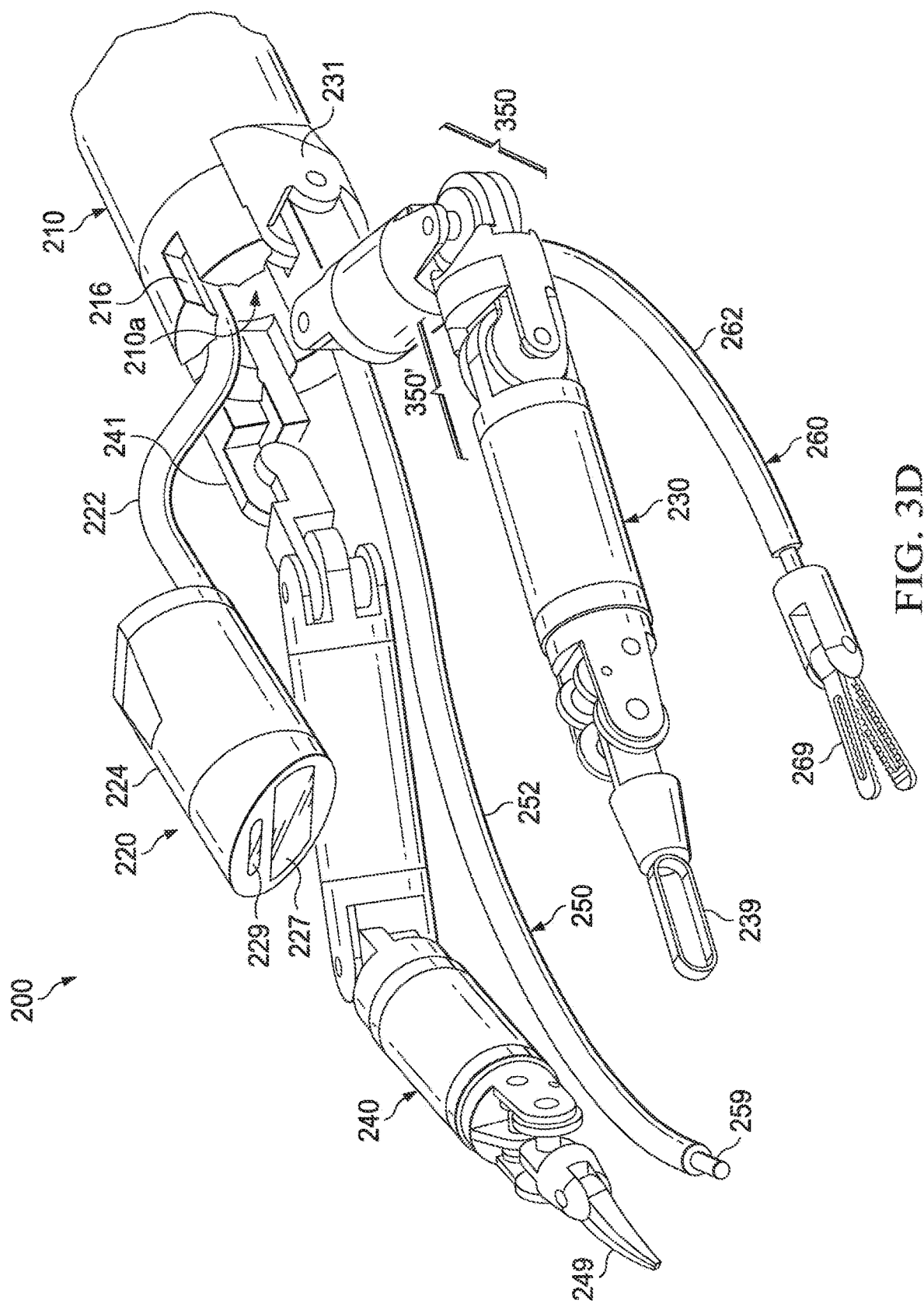
FIG. 3D is another illustration of a perspective view of an example embodiment of a surgical device configured in a forward-directed position.
Figure 4A:
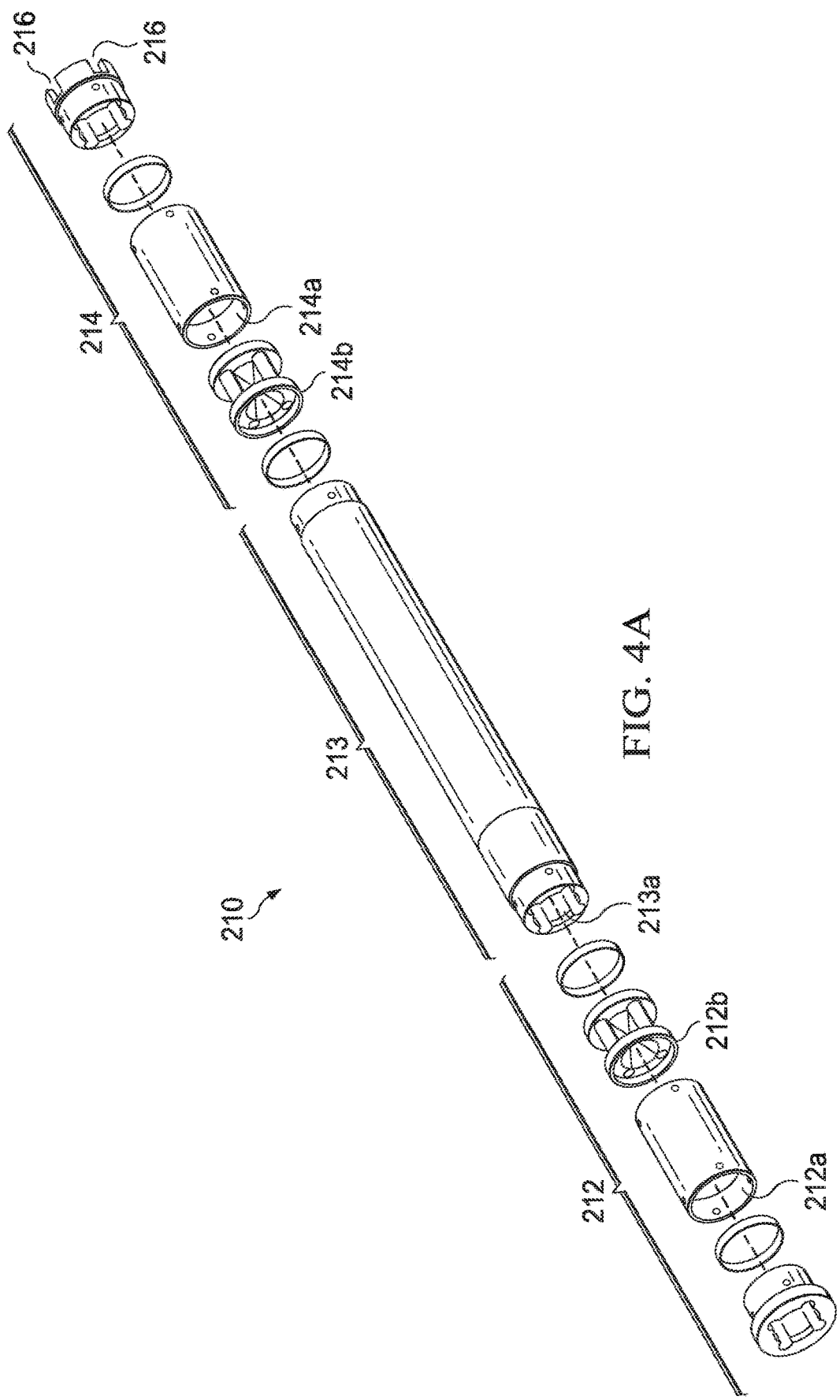
FIG. 4A is an illustration of a perspective exploded view of an example embodiment of a port assembly.

The port assembly 210 may be an elongated structure having a central access channel 210*a* formed through the port assembly 210. The central access channel 210*a* may be for use in inserting and removing instruments, such as one or more instrument arm assemblies 230, 240, one or more image capturing assemblies 220, one or more assistant arm assemblies 250, 260, etc. In an example embodiment, the port assembly 210 may include a first end section 212 and a second end section 214. The first end section 212 and second end section 214 may be fixably attachable to one another or formed as a unitary article. The port assembly 210 may also include a mid section 213 between the first end section 212 and the second end section 214. The first end section 212, second end section 214, and mid section 213 may be fixably attachable to one another, as illustrated in FIGS. 4A and 4B, or two or more of these sections may be formed as a unitary article. In an example embodiment, the first end section 212 may be the portion of the port assembly 210 that is secured to the external anchor 1, and the port assembly 210 may be fixed in position at an angle θ relative to the single opening of the patient of between about 0 to +/−90 degrees. These and other elements of the port assembly 210 will now be described below and with reference to FIGS. 2A-D, 3A-D, and 4A-D.

As illustrated in at least FIGS. 4A and 4B, the port assembly 210 may comprise a first end section 212. The first end section 212 may have a first end channel 212a formed through the first end section 212. The first end channel 212a may be considered as a part of the central access channel 210a. The first end section 212 may also include a portion operable to be secured to the external anchor 1, such as a portion on an exterior portion of the first end section 212.

The first end section 212 may also include a first gate assembly 212b, as illustrated in FIGS. 4A, 4C, and 4D. The first gate assembly 212 may be configurable to control access through the first end channel 212a. For example, the first gate assembly 212b may be configurable to be in an open position, as illustrated in FIG. 4C, so as to allow access through the first end channel 212a. The first gate assembly 212b may also be configurable to be in a closed position, as illustrated in FIG. 4D, so as to prevent or restrict access through the first end channel 212a. The first gate assembly 212b may also be configurable to be in a partially closed (or partially opened) position (not shown). The first gate assembly 212b may also be configurable to transition between the closed position and the open position.

In an example embodiment, the first gate assembly 212b may be provided within the first end section 212 in such a way that, when the first gate assembly 212b is configured to be in the open position, as illustrated in FIG. 4C, the first end channel 212a is substantially or completely unobstructed by the first gate assembly 212b. The first gate assembly 212b may be configured to be in the open position when a surgeon desires to insert (or remove) an instrument into (or out of) the cavity of the patient via the first end channel 212a (and the rest of the central access channel 210a).

Similarly, the first gate assembly 212b may be provided within the first end section 212 in such a way that, when the first gate assembly 212b is configured to be in the closed position, as illustrated in FIG. 4D, the first end channel 212a is substantially or completely obstructed by the first gate assembly 212b. The first gate assembly 212b may be configured to be in the closed position when a surgeon desires to maintain an insufflation of the cavity of the patient and/or when the surgeon does not need to insert (or remove) an instrument into (or out of) the cavity of the patient via the first end channel 212a.

The first gate assembly 212b may include a first expandable portion 212b configurable to expand when the first gate assembly 212b is configured to the closed position, as illustrated in FIG. 4D. When the first gate assembly 212b is configured to the closed position, the first expandable portion 212b may be operable to substantially or completely block, among other things, a gas medium (and/or other medium) from passing through the first end channel 212a. For example, if the cavity of the patient is being insufflated using a gas, such as carbon dioxide ($CO_2$), the first gate assembly 212b (i.e., the first expandable portion 212b) may be configurable to substantially prevent the carbon dioxide gas from leaving the cavity of the patient through the first end channel 212a.

The first expandable portion 212b may include one or more first expandable members. For example, the first expandable portion 212b may include six expandable members, as illustrated in FIGS. 4C and 4D. It is to be understood that the first expandable portion 212b may include more or less than six expandable members without departing from the teachings of the present disclosure. Some or all of the first expandable members may be integrated together and/or in communication with one another, such as in a manner where some or all of the first expandable members are operable to receive pressure (i.e., gas medium) from a common or same first source 212b'. For example, when the first gate assembly 212b is configured to the closed position, the first source 212b' may be configurable to provide a positive pressure (i.e., a supply of gas) so as to cause some or all of the first expandable members to expand and block the first end channel 212a (e.g., hermetically block the first end channel 212a). Similarly, when the first gate assembly 212b is configured to the open position, the first source 212b' may be configurable to provide a negative pressure (i.e., remove gas) so as to cause one or more (or all) of the first expandable members to not expand (and/or contract) and unblock the first end channel 212a. It is to be understood that more than one first sources 212b' may provide the positive pressure and negative pressure to the one or more expandable members without departing from the teachings of the present disclosure.

It is recognized in the present disclosure that the first gate assembly 212b may also include a valve (not shown), or the like, in addition to or in replacement of the first expandable portion 212b. The valve may be configurable to perform substantially the same actions of blocking the first end channel 212a when the first gate assembly 212b is configured to the closed position and unblocking the first end channel 212a when the first gate assembly 212b is configured to the open position. The valve may be any type of valve configurable to perform the actions described above and in the present disclosure. The valve may include, but is not limited to including, a ball valve, gate valve, etc., so long as the valve is configurable to substantially block/unblock the first end channel 212a and prevent a gas medium from passing through the first end channel 212a.

The port assembly 210 may also include the second end section 214, as illustrated in at least FIGS. 4A and 4B. The second end section 214 may have a second end channel 214a formed through the second end section 214. The second end channel 214a may be substantially or completely aligned with the first end channel 212a. The second end channel 214a, as well as the first end channel 212a, may be considered as a part of the central access channel 210a in example embodiments. The second end section 214 may also include an insufflation port (not shown) for use in providing insufflation to the cavity of the patient.

The second end section 214 may also include a second gate assembly 214, as illustrated in FIGS. 4A, 4C, and 4D. The second gate assembly 214 may be configurable to control access through the second end channel 214a. For example, the second gate assembly 214b may be configurable to be in an open position, as illustrated in FIG. 4C, so as to allow access through the second end channel 214a. The second gate assembly 214b may also be configurable to be in a closed position, as illustrated in FIG. 4D, so as to prevent or restrict access through the second end channel 214a. The second gate assembly 214b may also be configurable to be in a partially closed (or partially opened) position (not shown). The second gate assembly 214b may also be configurable to transition between the closed position and the open position.

In an example embodiment, the second gate assembly 214b may be provided within the second end section 212 in such a way that, when the second gate assembly 214b is configured to be in the open position, as illustrated in FIG. 4C, the second end channel 214a is substantially or completely unobstructed by the second gate assembly 214b. The second gate assembly 214b may be configured to be in the open position when a surgeon desires to insert (or remove) an instrument into (or out of) the cavity of the patient via the second end channel 214a (and the rest of the central access channel 210a).

Similarly, the second gate assembly 214b may be provided within the second end section 214 in such a way that, when the second gate assembly 214b is configured to be in the closed position, as illustrated in FIG. 4D, the second end channel 214a is substantially or completely obstructed by the second gate assembly 214b. The second gate assembly 214b may be configured to be in the closed position when a surgeon desires to maintain an insufflation of the cavity of the patient and/or when the surgeon does not need to insert (or remove) an instrument into (or out of) the cavity of the patient via the second end channel 214a.

The second gate assembly 214b may include a second expandable portion 214b configurable to expand when the second gate assembly 214b is configured to the closed position, as illustrated in FIG. 4D. When the second gate assembly 214b is configured to the closed position, the second expandable portion 214b may be operable to substantially or completely block, among other things, a gas medium (and/or other medium) from passing through the second end channel 214a. For example, if the cavity of the patient is being insufflated using a gas, such as carbon dioxide ($CO_2$), the second gate assembly 214b (i.e., the second expandable portion 214b) may be configurable to substantially prevent the carbon dioxide gas from leaving the cavity of the patient through the second end channel 214a.

The second expandable portion 214b may include one or more second expandable members. For example, the second expandable portion may include six expandable members, as illustrated in FIGS. 4C and 4D. It is to be understood that the second expandable portion 214b may include more or less than six expandable members without departing from the teachings of the present disclosure. Some or all of the second expandable members may be integrated together and/or in communication with one another, such as in a manner where some or all of the second expandable members are operable to receive pressure (i.e., gas medium) from a common or same second source 214b'. For example, when the second gate assembly 214b is configured to the closed position, the second source 214b' may be configurable to provide a positive pressure (i.e., a supply of gas) so as to cause some or all of the second expandable members to expand and block the second end channel 214a (e.g., hermetically block the second end channel 214a). Similarly, when the second gate assembly 214b is configured to the open position, the second source 214b' may be configurable to provide a negative pressure (i.e., remove gas) so as to cause some or all of the second expandable members to not expand (and/or contract) and unblock the second end channel 214a. It is to be understood that more than one second sources 214b' may provide the positive pressure and negative pressure to the one or more expandable members without departing from the teachings of the present disclosure. It is also to be understood in the present disclosure that one or more of the first sources 212b' and one or more of the second sources 214b' may be the same or different sources.

It is recognized in the present disclosure that the second gate assembly 214b may also include a valve (not shown), or the like, in addition to or in replacement of the second expandable portion 214b. The valve may be configurable to perform substantially the same actions of blocking the second end channel 214a when the second gate assembly 214b is configured to the closed position and unblocking the second end channel 214a when the second gate assembly 214b is configured to the open position. The valve may be any type of valve configurable to perform the actions described above and in the present disclosure. The valve may include, but is not limited to including, a ball valve, gate valve, etc., so long as the valve is configurable to substantially block/unblock the second end channel 214a and prevent a gas medium from passing through the second end channel 214a.

The second end section 214 may also include one or more anchor ports 216, as illustrated in FIGS. 4A and 4B. Each of the anchor ports 216 may be operable to enable an instrument arm assembly 230 or 240, image capturing assembly 220, and/or assistant arm assemblies 250 or 260 to be secured to and unsecured from the port assembly 210. Each of the anchor ports 216 may be formed in any one or more of a plurality of shapes, holes, slots, indentations, protrusions, hooks, fasteners, magnets, buckles, or the like, including those described above and in the present disclosure. For example, as illustrated in FIGS. 4A and 4B, one or more of the anchor ports 216 may include one or more slots, or the like, operable to allow a shoulder section 231 of an instrument arm assembly 230 or 240 to be inserted into and attached.

In example embodiments, the port assembly 210 may also include the mid section 213, as illustrated in at least FIGS. 4A and 4B. The mid section 213 may have a mid section channel 213a formed through the mid section 213. The mid section channel 213a may be substantially or completely aligned with the first end channel 212a and/or the second end channel 214a. In this regard, the mid section channel 213a, as well as the first end channel 212a and/or the second end channel 214a, may be considered as a part of the central access channel 210a in example embodiments. The mid section 213 may also include an insufflation port (not shown) in addition to or in replacement of the insufflation port (not shown) of the second end section 214. In some example embodiments, the mid section 213 may also include a mid section gate assembly (not shown) similar to that of the first gate assembly 212 and second gate assembly 214 described above and in the present disclosure.

In example embodiments, the mid section channel 213a may be operable to cooperate with the first gate assembly 212b and the second gate assembly 214b to function as or like an isolation chamber for instruments, such as the instrument arm assembly 230 or 240, image capturing assembly 220, assistant arm assembly 250 or 260, etc. For example, when an instrument, such as the instrument arm assembly 230, needs to be inserted into the cavity of the patient via the port assembly 210 (or central access channel 210a) and an insufflation of the cavity of the patient needs to be maintained, the first gate assembly 212*b* may be configured to the open position to allow the instrument to be inserted into the mid section channel 213*a*. After the instrument (or most of it) passes through the first gate assembly 212*b*, the first gate assembly 212*b* may be configured to the closed position. The second gate assembly 214*b* may then be configured to the open position to allow the instrument to be further inserted through the port assembly 210. After the instrument (or most of it) passes through the second gate assembly 214*b*, the second gate assembly 214*b* may be configured to the closed position.

In respect to the central access channel 210*a*, the central access channel 210*a* may include or be formed by the first end channel 212*a*, the second end channel 214*a*, and/or the mid section channel 213*a*. The central access channel 210*a* may be operable to provide an access port (i.e. a passageway or channel) to allow an insertion (or removal) of one or more instruments, such as one or more instrument arm assemblies 230 or 240, one or more image capturing assemblies 220, one or more assistant arm assemblies 250 or 260, etc.

In an example embodiment, the first end section 212, the second end 214, and/or the mid section 213 may be substantially cylindrical in shape. The first end section 212, the second end section 214, and/or the mid section 213 may also be formed in any one of a plurality of other shapes, sizes, and/or dimensions without departing from the teachings of the present disclosure.

In example embodiments, an outer diameter of the first end section 212, the second end 214, and/or the mid section 213 may be between about 28 to 35 mm and an inner diameter (unblocked) of the first end section 212, the second end 214, and/or the mid section 213 may be between about 16 to 21 mm. In an example embodiment, the outer diameter of the first end section 212, the second end 214, and/or the mid section 213 may be about 33 mm and the inner diameter (unblocked) of the first end section 212, the second end 214, and/or the mid section 213 may be about 19 mm. The length of the first end section 212 may be between about 80 to 100 mm, the length of the second end section 214 may be between about 80 to 200 mm, and the length of the mid section 213 may be between about 60 to 80 mm. The overall length of the port assembly 210 may be between about 320 to 380 mm. It is to be understood in the present disclosure that the above dimensions are merely an illustration of example embodiments, and as such the dimensions may be smaller or larger than those recited above without departing from the teachings of the present disclosure.

The port assembly 210, including the first end section 212, the second end section 214, the mid section 213, and/or the anchor ports 216, may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. The first gate assembly 212*b* and the second gate assembly 214*b* may be formed using any one or more of a plurality of materials, such as bio-compatible materials (such as silicone rubber and polyurethane). It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

The Image Capturing Assembly (e.g., Image Capturing Assembly 220)

In an example embodiment, the surgical device 200 may comprise one or more image capturing assemblies (e.g., image capturing assembly 220) configurable to be inserted into and attach to the port assembly 210. One or more of the image capturing assemblies 220 may comprise at an image capturing body 224, a multi-curvable body 222, and an anchoring portion 220*a*.

Figure 6A:
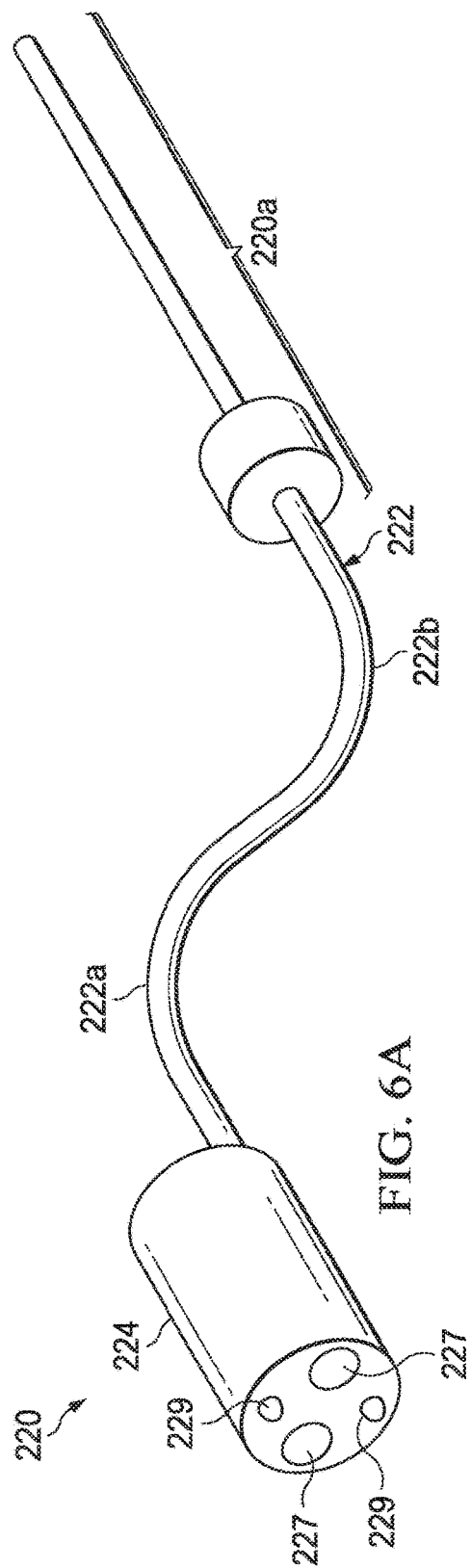
FIG. 6A is an illustration of a perspective view of an example embodiment of an image capturing assembly.
Figure 9A:
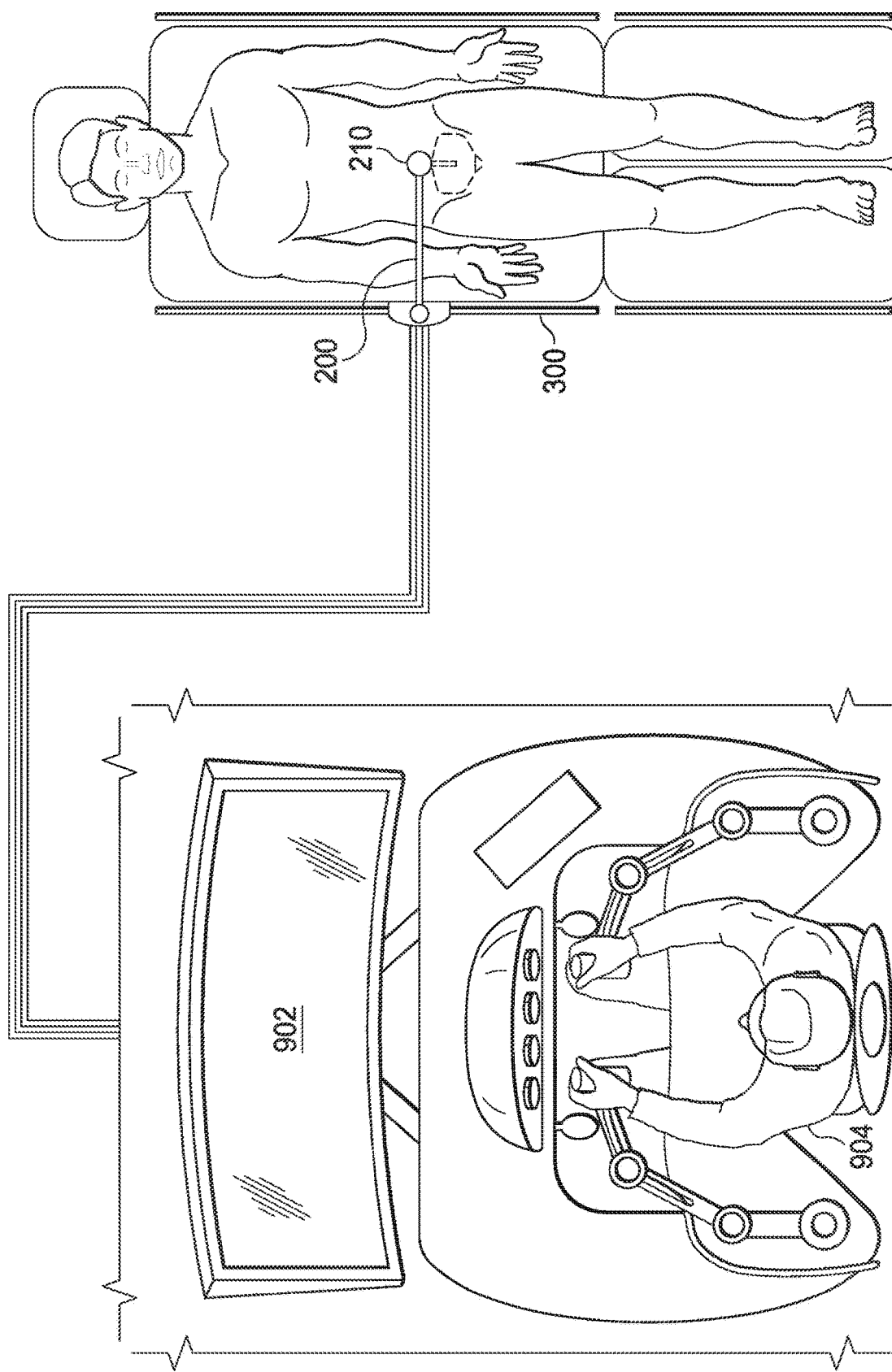
FIG. 9A is an illustration of a perspective view of an example embodiment of a surgical device system.
Figure 9B:
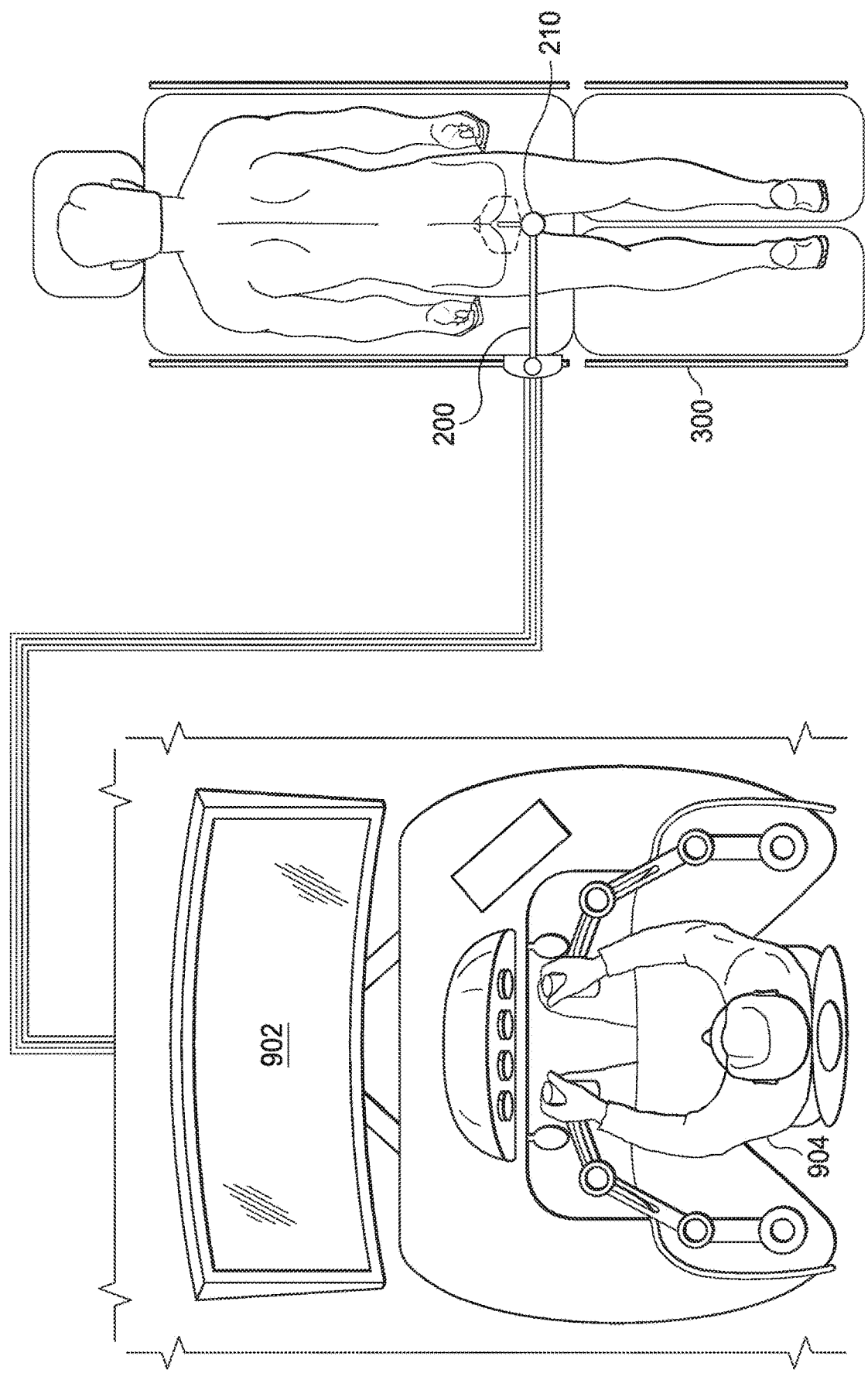
FIG. 9B is an illustration of a perspective view of another example embodiment of a surgical device system.

As illustrated in FIG. 6A, the image capturing body 224 may include one or more cameras 227. Each camera 227 may include a standard and/or high definition 2-dimensional (2D) and/or 3-dimensional (3D) camera operable to capture imaging, such as 2D and/or stereoscopic and/or autostereoscopic 3D imaging, including images, video, and/or audio, and provide in real-time via wired and/or wireless communication the captured imaging, including images, video, and/or audio, to the computing device (or controller or system) of one or more nearby and/or remotely located surgical teams 904, as described above and in the present disclosure. The computing device (or controller or system) may comprise one or more processors, one or more computer-human interfaces, one or more graphical displays (such as computer screens, television screens, portable devices, wearable devices such as glasses, etc.), and/or other devices and/or systems, an example of which is illustrated in FIGS. 9A and 9B. The one or more nearby and/or remotely located surgical teams 904 may be operable to view, hear, sense, analyze, and control (such as pan, zoom, process, adapt, mark, change resolution, etc.) the imaging displayed or represented on one or more standard and/or high definition 2D and/or 3D graphical displays 902, such as shown in the illustration of FIGS. 9A and 9B, and/or portable and/or wearable devices adapted to receive 2D and/or 3D imaging (not shown). The image capturing body 224 may also comprise one or more illumination sources 229, such as an LED, or the like, operable to illuminate or sense at least one or more parts, sections, and/or quadrants of the cavity of the patient, including instruments provided in the cavity of the patient. The image capturing body 224 may further comprise one or more internal temperature control assemblies operable to control (such as reduce) the temperature of one or more components of the image capturing body 224.

As illustrated in the example embodiment of FIG. 6A, one or more of the image capturing assemblies 220 may comprise a multi-curvable body 222 attached to the image capturing body 224. The multi-curvable body 222 may be any elongated multi-curvable, multi-bendable, multi-articulable, and/or snake-like (hereinafter "multi-curvable") body that can be controlled/configured by the surgical team (such as via the computing device/controller) to, among other things, straighten and/or curve (and hold such a straightness and/or curvature) at one or more of a plurality of locations along the multi-curvable body 222, curve (and hold such a curvature) in one or more of a plurality of curvatures, and/or straighten and/or curve (and hold such a straightness and/or curvature) in one or more of a plurality of directions. For example, as illustrated in FIG. 8H, the multi-curvable body 222 may be controllable/configurable by the surgical team (such as via the computing device/controller) to curve at two different locations 222*a* and 222*b* along the multi-curvable body 222, and each of the curves may include any curvature and in any direction. It is to be understood that the multi-curvable body 222 may be configurable to curve in more or less than two locations along the multi-curvable body 222 without departing from the teachings of the present disclosure. It is also to be understood that, when the multi-curvable body 222 is configured to curve at any location along the multi-curvable body 222, the curve may be held and/or released (or configured to uncurve, curve less, or straighten) by the surgical team (such as via the computing device/controller).

The multi-curvable body 222 may be formed in any one or more ways known in the art including. For example, the multi-curvable body 222 may include a plurality of segments, each segment linked to an adjacent segment in such a way that the segment may be controlled/configured to be pivotally positioned in a plurality of positions relative to the adjacent segment. As another example, the multi-curvable body 222 may include a plurality of wires, cables, or the like, distributed throughout the multi-curvable body 222 in such a way that a pulling/releasing, shortening/lengthening, tightening/loosening, etc. of one or a combination of cables enables the above-mentioned curving of one or more locations of the multi-curvable body 222 in one or more curvatures and in one or more directions. As another example, the multi-curvable body 222 may include a plurality of springs, gears, motors, etc. for achieving the above-mentioned curving. It is to be understood in the present disclosure that the multi-curvable body 222 may also include a combination of one or more of the above-mentioned approaches.

One or more internal temperature control assemblies (not shown) may be provided for each image capturing assembly 220. Each internal temperature control assembly may be operable to control (such as reduce) the temperature and/or heat emission of the aforementioned camera(s) 227, illumination source(s) 229, and/or multi-curvable body 222. In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well as any solids (if used), may be provided through an interior of the image capturing assembly 220 without increasing dimensions (such as diameter) of the image capturing assembly 220 and/or affecting the controllability/configurability of the multi-curvable body 222.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the cavity of the patient during a surgical procedure. When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the image capturing assembly 220. In example embodiments, the internal temperature control assembly may utilize a combination of gases, liquids, solids, and/or the like without departing from the teachings of the present disclosure.

The image capturing assembly 220 may be secured to the port assembly 210 in one or more of a plurality of ways, including those described above and in the present disclosure for the instrument arm assemblies 230 or 240 and/or the assistant arm assemblies 250 or 260. For example, the image capturing assembly 220 may also comprise an anchoring portion 220a (e.g., similar to the securing portion 231a of the instrument arm assembly 220) operable to attach (or secure) the image capturing assembly 220 to one or more anchor ports 216 of the port assembly 210.

In an example embodiment, the image capturing body 224 and the multi-curvable body 222 may each be substantially cylindrical in shape. The image capturing body 224 and the multi-curvable body 222 may also be formed in any one of a plurality of other shapes, sizes, and/or dimensions without departing from the teachings of the present disclosure.

In an example embodiment, the length of the multi-curvable body 222 may be between about 50 to 150 mm. In example embodiments, a length of multi-curvable body 222 may also be adjustable by the surgical team 904 before, during, and/or after insertion of the camera arm assembly into the cavity of the patient. The outer diameter of the multi-curvable body 222 may be between about 5 to 7 mm. It is to be understood in the present disclosure that the above dimensions are merely an illustration of example embodiments, and as such the dimensions may be smaller or larger than those recited above without departing from the teachings of the present disclosure.

The multi-curvable body 222 may be formed using any one or more of a plurality of materials, such as stainless steel, etc. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

Figure 6B:
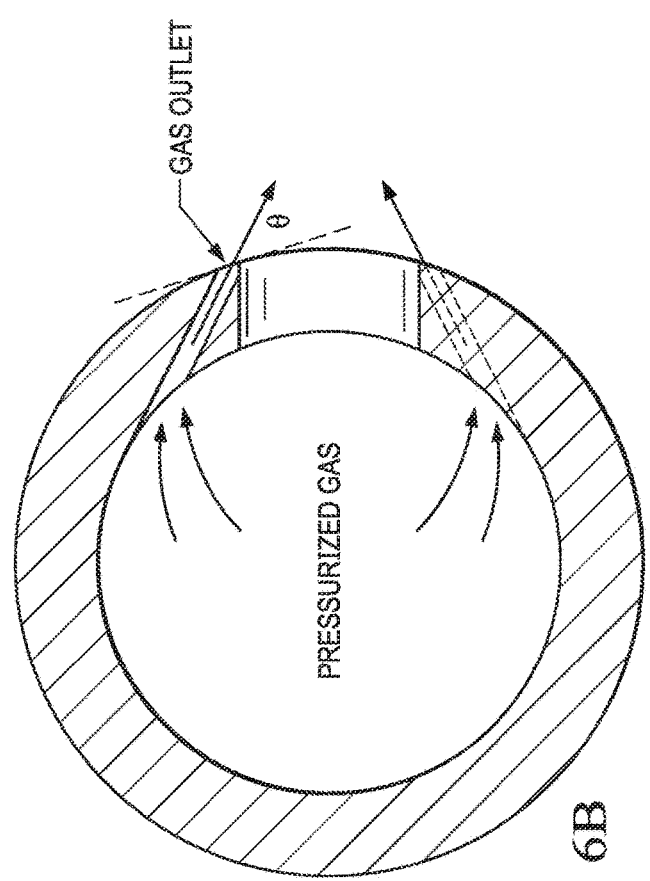
FIG. 6B is an illustration of a cross sectional view of another example embodiment of an image capturing assembly having an internal temperature control assembly.
Figure 6C:
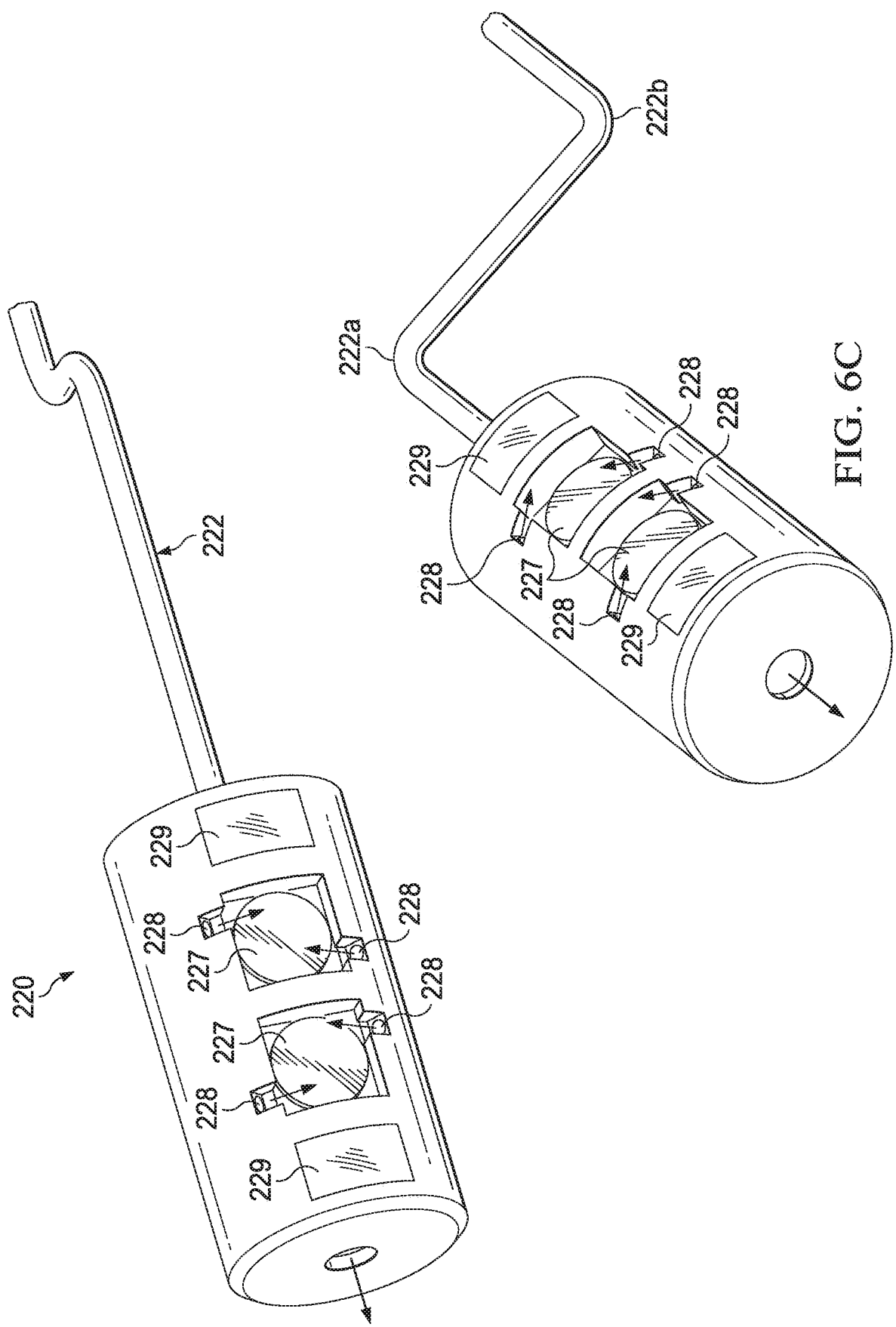
FIG. 6C is an illustration of perspective views of another example embodiment of an image capturing assembly having internal temperature control assemblies.

As illustrated in FIG. 6B and FIG. 6C, the image capturing assembly 220 may further comprise a gas shield 228 located nearby one or more lenses of the camera 227. The image capturing assembly 220 may further comprise a gas shield 228 located nearby one or more of the illumination sources 229 and/or any other sensors (such as temperature sensors, pressure sensors, humidity sensors, etc.) provided by the image capturing assembly 220. The gas shield 228 may comprise one or more openings or the like, one or more external gas sources 228, and one or more tubes, channels, or the like, between the one or more external gas sources and the one or more openings of the gas shield 228. In operation, the gas shield 228 may be operable to provide pressurized gases (and/or liquids), such as carbon dioxide, oxygen, other gases or liquids, or combinations thereof, via the one or more openings of the gas shield 228 to an area in front of the camera 227 (as well as in front of the illumination sources 229 and/or other sensors).

Figure 6D:
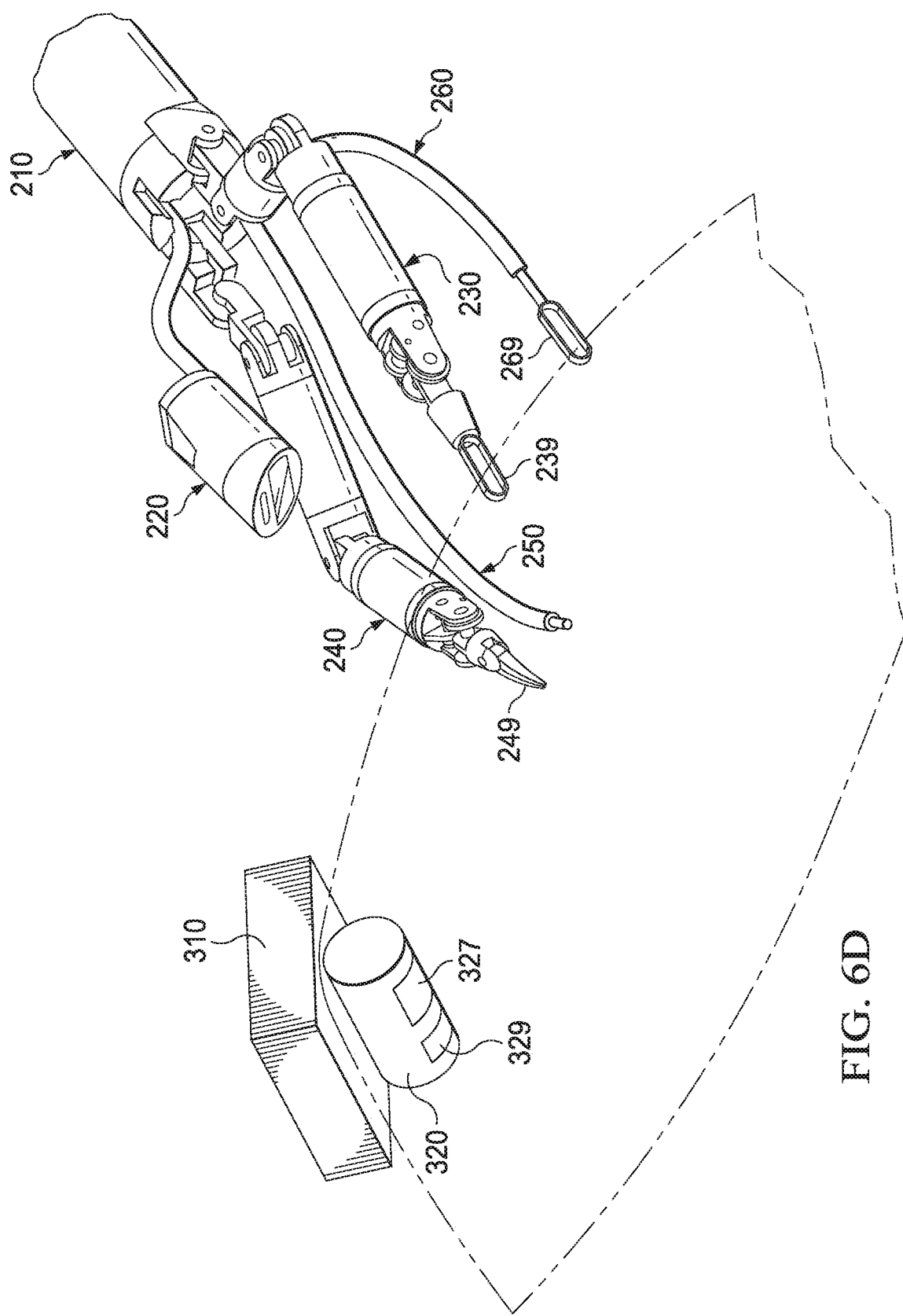
FIG. 6D is an illustration of a perspective view of the system in operation in a cavity of a patient, including a second image capturing assembly.
Figure 7:
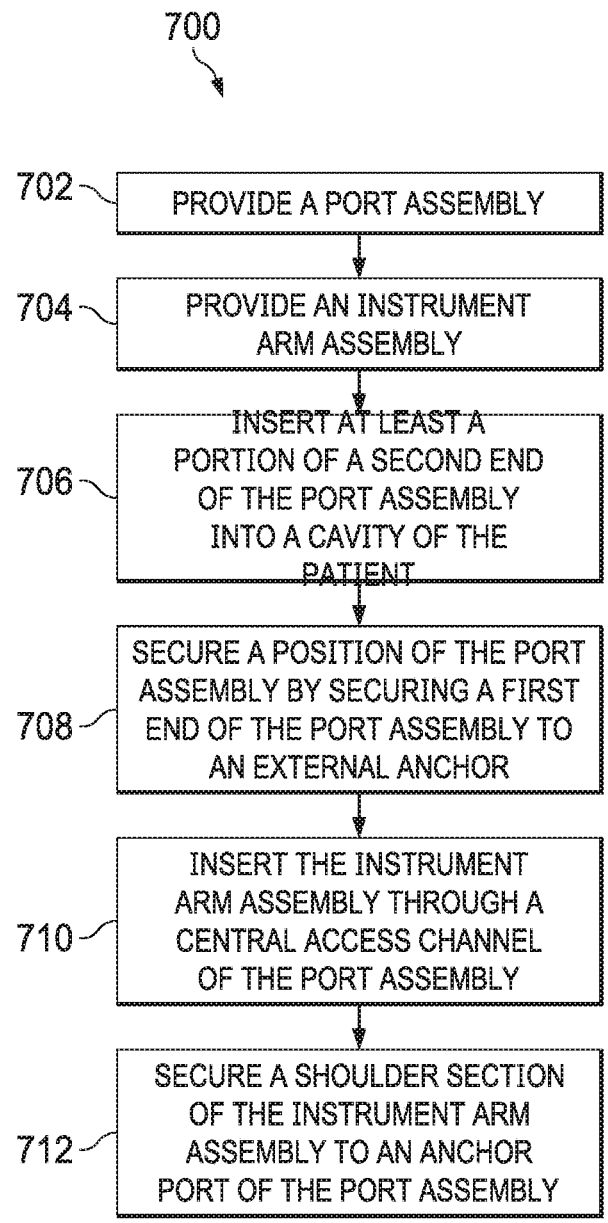
FIG. 7 is a flow diagram of an exemplary method for configuring a surgical device.

The overall system may also include one or more separate image capturing assemblies, such as the separate image capturing assembly 320 illustrated in FIG. 6D. The separate image capturing assembly 320 may be magnetically anchored by a magnetic anchor 310 to an internal wall of the cavity of the patient, such as via a permanent magnet, electromagnet, or the like. In some example embodiments, the magnetic anchor 310 may also be secured/held in position via an external anchor (not shown). The separate image capturing assembly 320 may include one or more cameras 327, and may also include one or more illumination sources 329.

The separate image capturing assembly 320 may be operable to provide one or more of a variety of views, including, but not limited to, a normal view, zoomed view, wide-angled view, and/or panoramic view of the cavity of the patient. The separate image capturing assembly 320 may be positioned in such a way as to provide the surgical team 904 with an unobstructed view of areas of interest within the cavity of the patient. In respect to positioning and securing the separate image capturing assembly 320 in place, as illustrated in FIG. 6D, the separate image capturing assembly 320 may be inserted through the central access channel 210a of the port assembly 210 and to the desired location of the interior wall of the cavity of the patient in one or more of a plurality of ways, including using a surgical tool (not shown), attaching the separate image capturing assembly 320 to a multi-curvable body (not shown) similar to that of the image capturing assembly 220 (as illustrated in FIGS. 2A, 2B, 3A, 3B, and 6D), etc.

The Instrument Arm Assembly (e.g., Instrument Arm Assembly 230, 240)

In an example embodiment, the surgical device 200 may comprise one or more instrument arm assemblies (e.g., first instrument arm assembly 230, second instrument arm assembly 240, third instrument arm assembly (not shown), fourth instrument arm assembly (not shown), etc.), each configurable to attach to the port assembly 210. Although certain figures and/or descriptions provided in the present disclosure may be directed to the first instrument arm assembly 230 and its elements, it is to be understood in the present disclosure that such figures and/or descriptions may also apply to other instrument arm assemblies, including second instrument arm assembly 240, third instrument arm assembly (not shown), fourth instrument arm assembly (not shown), etc.

Figure 5A:
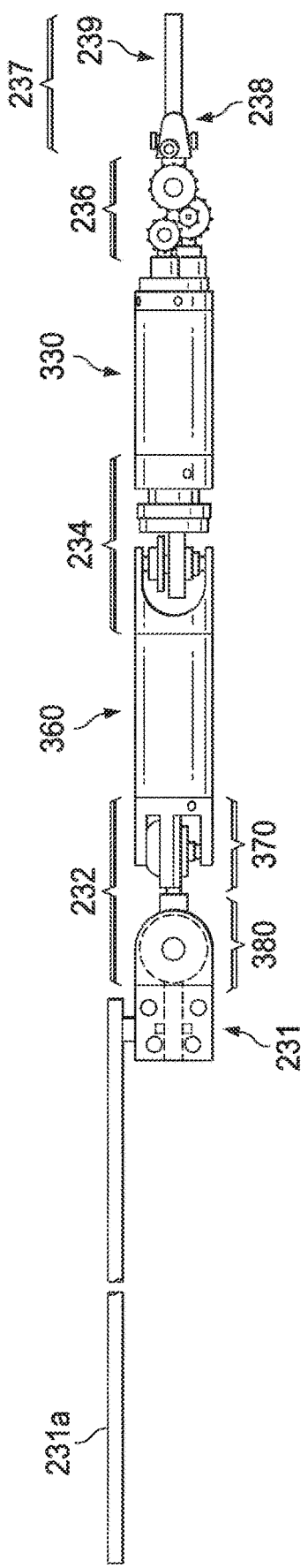
FIG. 5A is an illustration of a side view of an example embodiment of an instrument arm assembly.
Figure 5B:
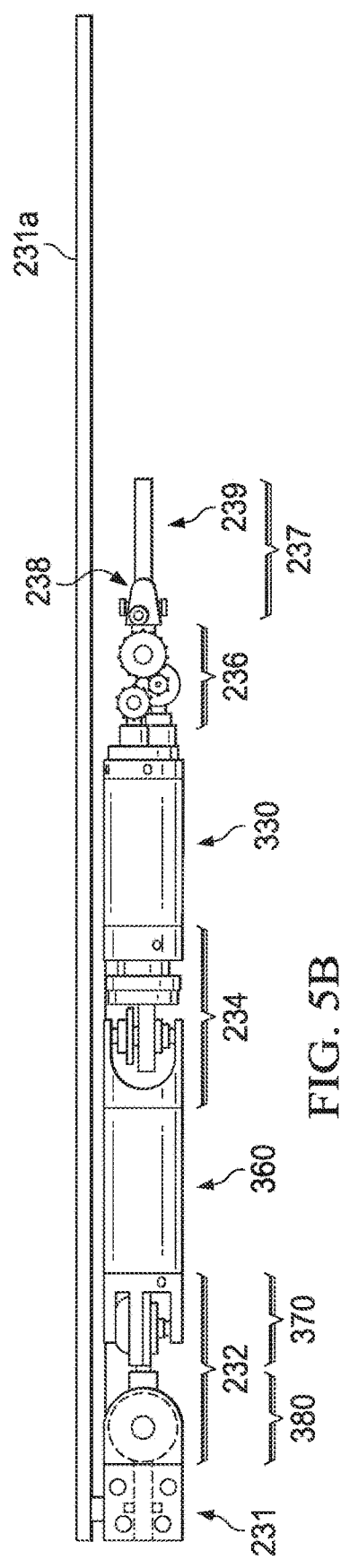
FIG. 5B is another illustration of a side view of an example embodiment of an instrument arm assembly.
Figure 5C:
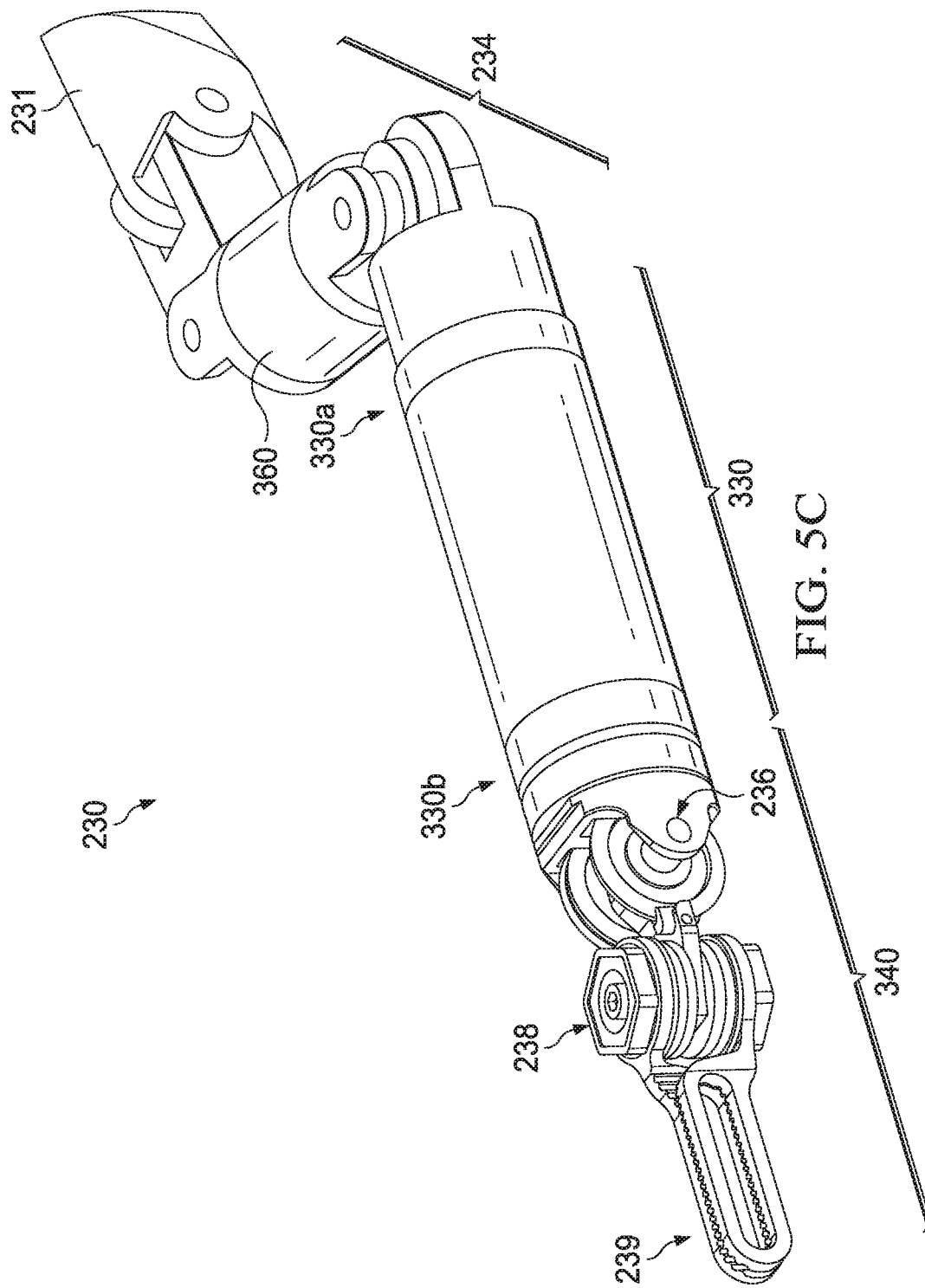
FIG. 5C is an illustration of a perspective view of an example embodiment of an instrument arm assembly.
Figure 5F:
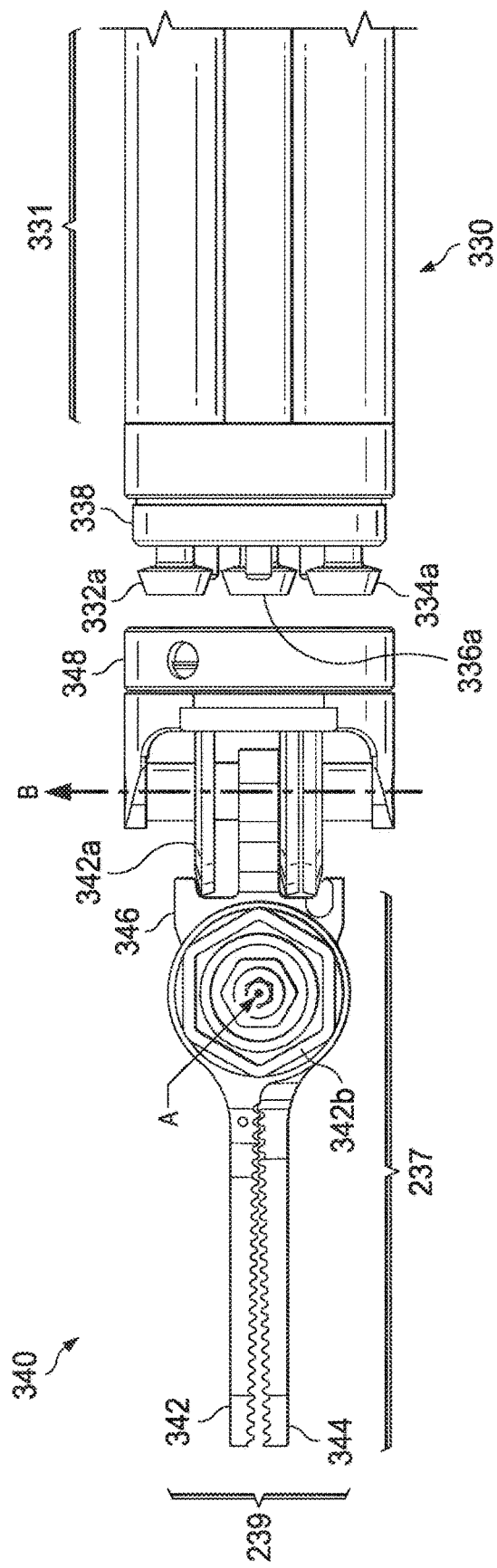
FIG. 5F is an illustration of a side view of an example embodiment of an end-effector assembly unsecured from an arm assembly.
Figure 5G:
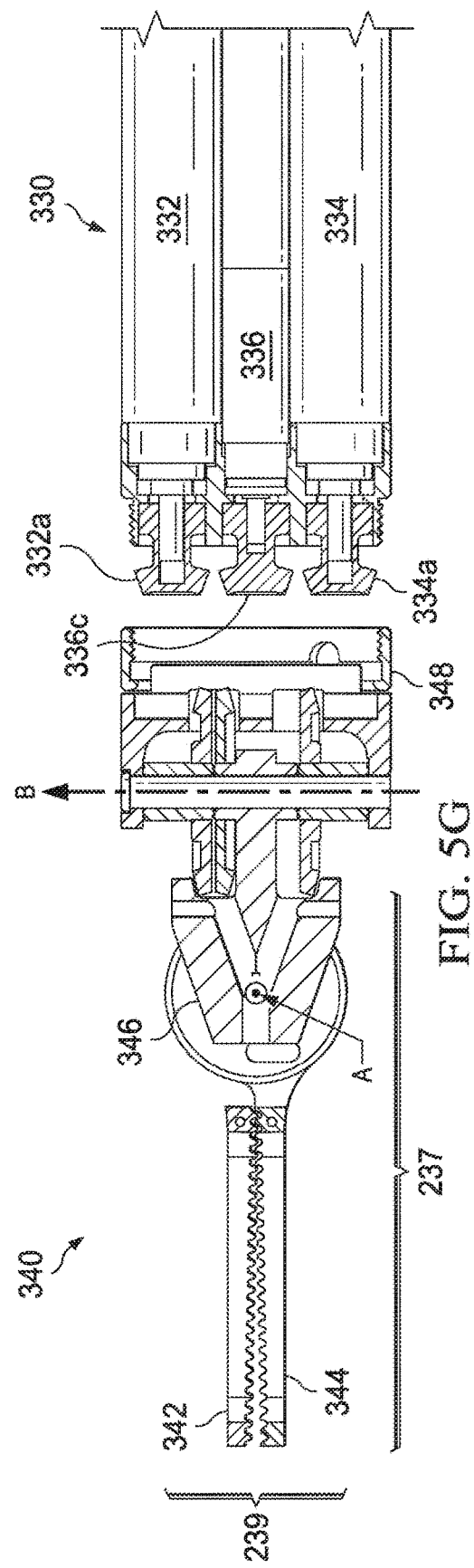
FIG. 5G is an illustration of a side cross-sectional view of an example embodiment of an end-effector assembly unsecured from an arm assembly.
Figures 5H, 5I:
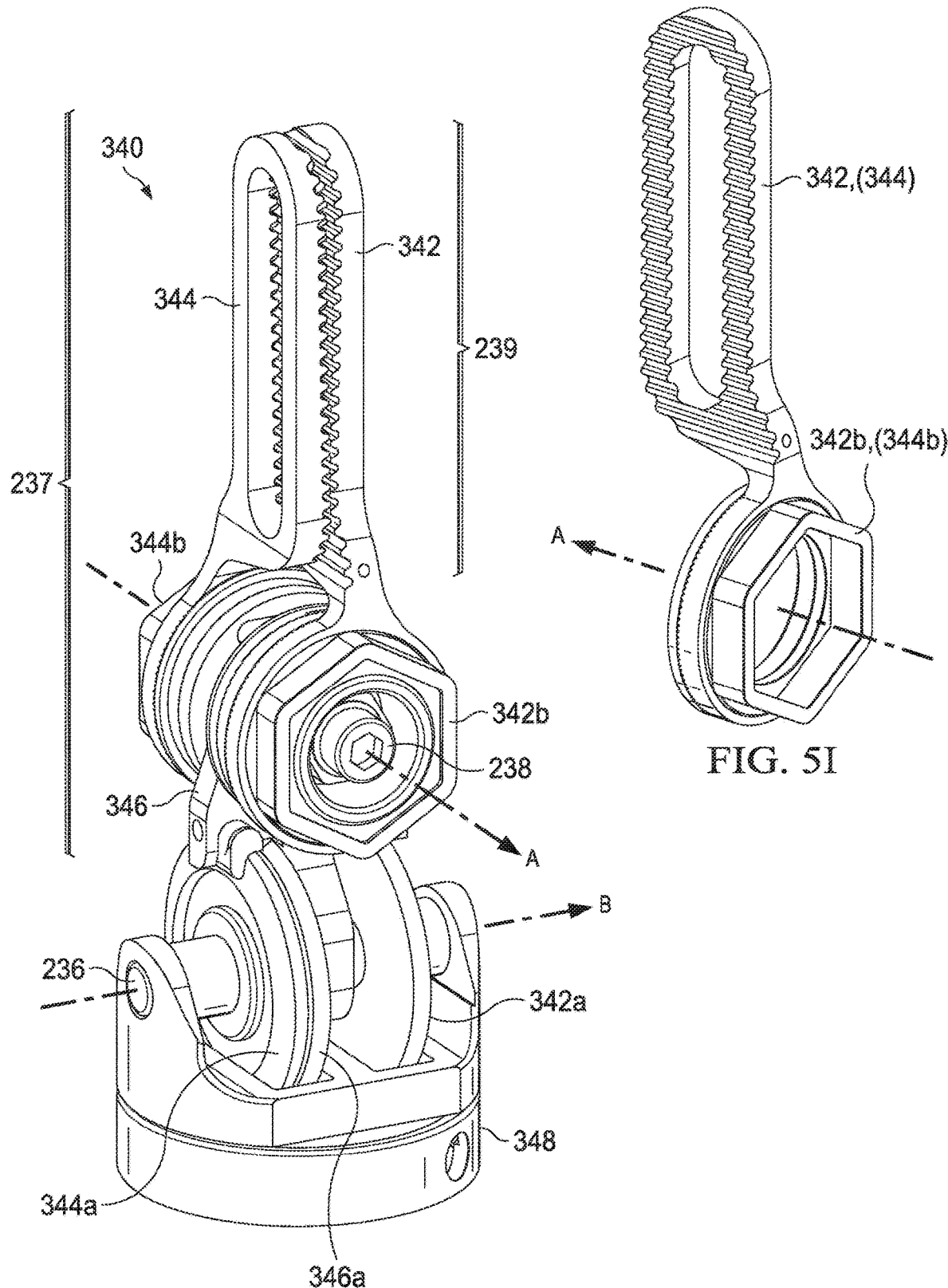
FIG. 5H is an illustration of a perspective view of an example embodiment of an end-effector assembly.
FIG. 5I is an illustration of a perspective view of an example embodiment of an instrument with an insulative portion.

One or more of the instrument arm assemblies (such as 230, 240) may comprise a configurable or configured serially (or linearly) connected arrangement of a plurality of instrument arm segments (or arm assemblies, such as a first arm assembly 330, second arm assembly 360, and shoulder section (e.g., shoulder assembly 231) illustrated in at least FIG. 5C and FIG. 5R) and a plurality of joint portions (such as an elbow joint assembly 234, and shoulder joint assembly 232 illustrated in at least FIG. 5L, FIG. 5M, FIG. 5S, and FIG. 5T), and an end effector assembly 340 (having at least a wrist assembly and an instrument assembly 237, which includes instrument(s) 239 having instrument 342 and/or instrument 344) integrated into and/or connected to one or more of the instrument arm segments and/or joint portions. Although certain figures and description in the present disclosure may be directed to an instrument arm assembly 230, 240 having a serially connected arrangement of an end effector assembly 340 at a distal end, followed by a first arm assembly 330, followed by an elbow joint assembly 234 (having an elbow pitch joint portion 350' followed by an elbow sway joint portion 350), followed by a second arm assembly 360, followed by a shoulder joint assembly 232 (having a shoulder pitch joint portion 370 followed by a shoulder sway joint portion 380), and followed by a shoulder section 231 at a proximal end, it is to be understood in the present disclosure that the serially connected arrangement for the instrument arm assembly 230, 240 may also be in other sequences and include (or not include) other elements. For example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder pitch joint portion 370, followed by a shoulder sway joint portion 380, and followed by a shoulder section 231 at a proximal end. As another example, the serially connected arrangement may include an end-effector assembly 340 at a distal end, followed by a first arm assembly 330, followed by an elbow sway joint portion 350, followed by an elbow pitch joint portion 350', followed by a second arm assembly 360, followed by a shoulder sway joint portion 380, followed by a shoulder pitch joint portion 370, and followed by a shoulder section 231 at a proximal end. In yet another example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder sway joint portion 380, followed by a shoulder pitch joint portion 370, and followed by a shoulder section 231 at a proximal end. As another example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder pitch joint portion 370, and followed by a shoulder section 231 at a proximal end. As another example, the serially connected arrangement may include an end-effector assembly 340 at a distal end, followed by a first arm assembly 330, followed by an elbow pitch joint portion 350', followed by an elbow sway joint portion 350, followed by a second arm assembly 360, followed by a shoulder sway joint portion 380, and followed by a shoulder section 231 at a proximal end. As another example, the serially connected arrangement may include an end-effector assembly 340 at a distal end, followed by a first arm assembly 330, followed by an elbow sway joint portion 350, followed by an elbow pitch joint portion 350', followed by a second arm assembly 360, followed by a shoulder pitch joint portion 370, and followed by a shoulder section 231 at a proximal end. As another example, the serially connected arrangement may include an end-effector assembly 340 at a distal end, followed by a first arm assembly 330, followed by an elbow sway joint portion 350, followed by an elbow pitch joint portion 350', followed by a second arm assembly 360, followed by a shoulder sway joint portion 380, and followed by a shoulder section 231 at a proximal end. In yet another example, the serially connected arrangement may include an end-effector assembly 340 at a distal end, followed by a first arm assembly 330, followed by an elbow sway joint portion 350, followed by a second arm assembly 360, followed by a shoulder pitch joint portion 370, followed by a shoulder sway joint portion 380, and followed by a shoulder section 231 at a proximal end. As another example, the serially connected arrangement may include an end-effector assembly 340 at a distal end, followed by a first arm assembly 330, followed by an elbow sway joint portion 350, followed by a second arm assembly 360, followed by a shoulder sway joint portion 380, followed by a shoulder pitch joint portion 370, and followed by a shoulder section 231 at a proximal end. Other serially connected arrangements with more or less elements are also contemplated without departing from the teachings of the present disclosure.

The end effector or instrument 239, 342, 344 may be any instrument suitable for use in surgical procedures, such as a cutting and/or gripping instrument. One or more of the instrument arm assemblies (such as 230, 240) may also comprise one or more illumination sources (not shown), such as an LED, or the like, operable to illuminate one or more parts of the end effector or instrument 239, 342, 344, instrument arm assemblies, and/or parts, sections, and/or quadrants of the abdominal cavity of the patient.

One or more of the instrument arm assemblies (such as 230, 240) may also comprise one or more integrated motors (e.g., integrated motors 332, 334, 336, and/or 339 illustrated in at least FIG. 5E, FIG. 5G, FIG. 5J, and FIG. 5K and integrated motors 362, 364, 366, and/or 369 illustrated in at least Figure M, FIG. 5N, FIG. 5O, FIG. 5T, FIG. 5U, and FIG. 5V), each integrated motor operable to provide at least one degree of freedom for the instrument arm assembly. Each integrated motor (e.g., integrated motors 332, 334, 336, 339, 362, 364, 366, and/or 369) may be fully and independently functioning motors that are housed entirely (with the exception of, for example, power and/or control cables, which may be fed via the port assembly) in an instrument arm segment (or arm assembly, such as the first arm assembly 330, second arm assembly 360, and/or shoulder assembly 231), such as in housing 331 and/or 360'. One or more of the instrument arm assemblies may also include an integrated haptic and/or force feedback subsystem (not shown) in communication with one or more of the integrated motors and/or other sensors and/or instruments operable to provide to the surgical team (such as via computing device/controller) with one or more of a plurality of feedback responses and/or measurements, including those pertaining to position (including orientation), applied force, proximity, temperature, pressure, humidity, etc., of, by, and/or nearby to the instrument arm assembly. For example, the surgical team 904 may be provided with a master input device having manipulators, or the like, having haptic and/or force feedback and designed to map and sense the surgical team's 904 delicate finger-twisting, wrist-bending, and/or other arm/shoulder movements into movements of the instrument arm (such as 230, 240) with high precision, high dexterity, and minimum burden, while also providing feedback of contact resistance (such as tissue resistance).

When an instrument arm assembly (such as 230, 240) comprises one or more illumination sources, cameras, haptic and/or force feedback instruments, and/or other sensors and/or instruments, as described above and in the present disclosure, the instrument arm assembly may also comprise a gas shield, such as the gas shield described above for the image capturing assembly 220. One or more of the instrument arm assemblies (such as 230, 240) may further comprise one or more internal temperature control assemblies operable to control (such as reduce or increase) the temperature of one or more components of the instrument arm assembly.

As illustrated in the example embodiment of FIGS. 2A-D, 3A-D, FIG. 5A, FIG. 5B, FIG. 5P, and FIG. 5Q, each of the instrument arm assemblies, including the first instrument arm assembly 230, may comprise shoulder section 231, second arm assembly 360, 360, first arm assembly 330, and end-effector assembly 340. The instrument arm assembly 230 may also comprise a shoulder joint assembly 232 having a shoulder sway joint section 380 and/or shoulder pitch joint section 370; an elbow joint assembly 234 having an elbow sway joint section 350 and/or elbow pitch joint section 350'; a third joint portion (or wrist section) 236 pivotally moveable relative to an axis B (as illustrated in at least FIGS. 5D-H); and an end effector joint portion 238 pivotally moveable relative to an axis A (as illustrated in at least FIGS. 5D-H). Each of the aforementioned joint portions may be configurable, either manually and/or via the computing device (or system), to provide an attached instrument arm segment (and the end effector 239, 342, 344) with one or more in vivo degrees of freedom when the instrument arm assembly is provided in the abdominal cavity of the patient. For example, the shoulder joint assembly 232 may be operable to provide the second arm assembly 360 with one or more degrees of freedom (e.g., resembling the one or more degrees of freedom of the human shoulder). Specifically, the shoulder joint assembly 232 may include a shoulder sway joint section 380 operable to provide the second arm assembly 360 with a movement (e.g., rotation or pivotal movement) relative to an axis E (as illustrated in at least FIGS. 5L, 5M, 5S, and 5T). The shoulder joint assembly 232 may include a shoulder pitch joint section 370 operable to provide the second arm assembly 360 with a movement (e.g., rotation or pivotal movement) relative to an axis D (as illustrated in at least FIGS. 5L, 5M, 5S, and 5T). Axis E may be different from axis D (e.g., axis E may be substantially orthogonal to axis D). As another example, the elbow joint assembly 234 may be operable to provide the first arm assembly 330 with one or more degrees of freedom. Specifically, the elbow joint assembly 234 may include an elbow sway joint assembly 350 operable to provide the first arm assembly 330 with a movement (e.g., rotation or pivotal movement) relative to an axis C (as illustrated in at least FIGS. 5L, 5M, 5S, and 5T). The elbow joint assembly 234 may include an elbow pitch joint section 350' operable to provide the first arm assembly 330 with a movement (e.g., rotation or pivotal movement) relative to an axis C' (as illustrated in at least FIGS. 5S and 5T). Axis C may be different from axis C' (e.g., axis C may be substantially orthogonal to axis C'). As another example, the third joint portion (or wrist section) 236 may be operable to provide the instrument assembly 237 with one or more degrees of freedom resembling the one or more degrees of freedom of the human wrist. Specifically, the third joint portion (or wrist section) 236 may be operable to provide the instrument assembly 237 with a movement (e.g., rotation or pivotal movement) relative to an axis B (as illustrated in at least FIGS. 5L, 5M, 5S, and 5T). As another example, the end effector joint portion 238 (as illustrated in at least FIGS. 5A-B, 5P-Q, 5H) may be operable to provide the end effector or instrument 239, 342, 344 with one or more degrees of freedom. Specifically, the end effector joint portion 238 may be operable to provide the end effector or instrument 239, 342, 344 with a movement (e.g., rotation or pivotal movement) relative to an axis A (as illustrated in at least FIGS. 5D-I, 5L-M, 5S-T). Axis B may be different form axis A (e.g., axis B may be substantially orthogonal to axis A). Accordingly, one or more of the instrument arm assemblies may be configurable, either manually and/or via the computing device/controller, to provide seven or more in vivo degrees of freedom and, together with the at least one to three or more in vitro degree of freedom provided by the port assembly 210 and the controllable swivel assembly 1000 (see FIGS. 10A and 10B), the one or more of the instrument arm assemblies may be configurable, either manually and/or via the computing device/controller, to provide a total of eight to ten or more degrees of freedom. It is recognized herein that the aforementioned at least seven in vivo degrees of freedom for the instrument arm assembly enables at least the full range of natural movements by a surgeon's arm (via a controller/computer-human interface/manipulator/master input device, such as the example illustrated in FIGS. 9A and 9B) to be substantially directly mapped and/or translated to the instrument arm assembly.

Each joint portion, including joint portions 232, 370, 380, 234, 350, 350', 236, and/or 238 may comprise any one or more configurations of gears and/or gear assemblies, including straight gear configurations, planetary gear configurations, beveled gear configurations, spiral beveled gear configurations, hypoid gear configurations, helical gear configurations, worm gear configurations, and/or any other gear configuration without departing from the teachings of the present disclosure. In example embodiments, each instrument arm assembly may also comprise one or more internal integrated motors 332, 334, 336, 339, 362, 364, 366, 369, or the like, operable to actuate (e.g., via first instrument drive portion 332a, second instrument drive portion 334a, wrist drive portion 336a, first arm assembly drive assembly 339a (which is configurable to drive the first arm assembly 330 relative to an axis F, as illustrated in at least FIG. 5K), elbow sway drive portion 362a, elbow pitch drive portion 362a', shoulder pitch drive portion 364a, shoulder sway drive portion 366a) the gears of each joint portion (e.g., first instrument driven portion 342a, second instrument driven portion 344a, wrist driven portion 346a, first arm assembly driven assembly 347 (which is configurable to be driven by the first arm assembly drive assembly 339a to drive the first arm assembly 330 relative to an axis F, as illustrated in at least FIG. 5K), elbow sway driven portion 352, elbow pitch driven portion 352', shoulder pitch driven portion 364b, shoulder sway driven portion 366b, 366c (if needed), 366d (if needed)) and joint portions 232, 370, 380, 234, 350, 350', 236, and 238 and/or the segments 231, 360, 330, and 340. In this regard, each of the integrated motors, joint portions, and/or segments described above and in the present disclosure may be operable to communicate, such as receive control commands and/or transmit information, from and/or to the computing device/controller of one or more nearby and/or remotely located surgical teams 904 via wired and/or wireless communication in example embodiments. Furthermore, each of the integrated motors, joint portions, and/or instrument arm segments described above and in the present disclosure may be operable to receive power and/or control signals from an external power source and/or the computing device/controller via wired and/or wireless transmissions in example embodiments.

End-Effector Assembly (e.g., End-Effector Assembly 340).

An example embodiment of the end-effector assembly (e.g., end-effector assembly 340) may comprise an instrument assembly 237. The end-effector assembly 340 may also include a wrist assembly. The instrument assembly 237 may include a first instrument assembly and a second instrument assembly. Although the figures illustrate an end-effector assembly having a first instrument and a second instrument, it is to be understood in the present disclosure that the end-effector assembly may have more other instruments or may only have a first instrument or a second instrument without departing from the teachings of the present disclosure. The wrist assembly may include wrist joint portion 236, and may also include wrist connector 348.

(i) First Instrument Assembly.

An example embodiment of the first instrument assembly may comprise a first instrument (e.g., first instrument 342) for use in performing a surgical action. The first instrument 342 may be any surgical instrument without departing from the teachings of the present disclosure.

In an example embodiment, the first instrument 342 may be configurable to receive an electric current (e.g., first electric current) applied from a first energy source (not shown) so as to perform actions of an electrosurgical instrument. Although the first instrument may be described above and in the present disclosure to receive an electric current, it is to be understood that the first instrument may also be configurable to receive a voltage potential, thermal energy, heat, cold temperature application, radiation, etc. to perform the said surgical action without departing from the teachings of the present disclosure.

The first instrument assembly may also comprise a first instrument driven portion (e.g., first instrument driven portion 342a). The first instrument driven portion 342a may be configurable to be driven by the first instrument drive portion 332a of the integrated motor 332. The first instrument driven portion 342a may be driven by the first instrument drive portion 332a in such a way as to move the first instrument 342. For example, the first instrument driven portion 342a may be driven to move the first instrument 342 relative to a first axis (e.g., axis A). In this regard, such movement of the first instrument 342 may be a rotation of a distal end of the first instrument 342 relative to a proximal end of the first instrument 342, and such proximal end may serve as a pivot for such movement.

The first instrument driven portion 342a may be any mechanism, device, or the like, configurable to be driven by the first instrument drive portion 332a. For example, the first instrument driven portion 342a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one first instrument driven portion, it is to be understood in the present disclosure that the end-effector assembly may have more than one first instrument driven portions without departing from the teachings of the present disclosure.

In example embodiments wherein the end-effector assembly 340 is detachable (i.e., unsecurable) from the arm assembly 330, it is to be understood that the first instrument drive portion 332a of the integrated motor 332 may be operable to drive the first instrument driven portion 342a when the end-effector assembly 340 is secured (i.e., attached) to the arm assembly 330. Specifically, the first instrument drive portion 332a of the integrated motor 332 may be operable to drive the first instrument driven portion 342a when the wrist connector portion 338 is secured (i.e., attached) to the wrist assembly (as further described below and in the present disclosure) of the end-effector assembly (and more specifically, the connector 348 of the end-effector assembly 340).

In example embodiments wherein the end-effector assembly 340 is detachable (i.e., unsecurable) from the arm assembly 330, it is to be understood that one or more connectable and unconnectable electric wires, cables, or the like, may be provided to enable the first instrument 342 to receive the electric current from the energy source to perform the actions of an electrosurgical instrument.

The first instrument assembly may also comprise a first instrument insulative portion (e.g., first instrument insulative portion 342b). The first instrument insulative portion 342b may be providable between the first instrument 342 and one or more portions of the end-effector assembly 340 so as to electrically isolate (or electrically insulate, thermally isolate, thermally insulate, and the like) the first instrument 342 from the one or more portions of the end-effector assembly 340.

In an example embodiment, the first instrument insulative portion 342b may be providable between the first instrument 342 and the first instrument driven portion 342a so as to electrically isolate (or electrically insulate, thermally isolate, thermally insulate, and the like) the first instrument 342 from the first instrument driven portion 342a. Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the second instrument 344 via the first instrument driven portion 342a and/or other component/portion of the surgical arm assembly.

The first instrument insulative portion 342b may be formed using any one or more of a plurality of materials, such as electrically insulative materials, thermally insulative materials, plastics, elastomers, ceramics, glasses, and minerals. It is to be understood in the present disclosure that other materials may also be used without departing from the teachings of the present disclosure.

The first instrument 342 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the first instrument 342 may include an opening, or the like, for use in receiving and housing at least a portion of the first instrument insulative portion 342b. The first axis (e.g., axis A) may be formed through a center of the opening of the first instrument 342 in example embodiments. Although the opening may be depicted in the figures to be circular in shape and the corresponding exterior portion of the first instrument insulative portion 342b being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

(ii) Second Instrument Assembly.

An example embodiment of the second instrument assembly may comprise a second instrument (e.g., second instrument 344) for use in performing a surgical action. The second instrument 344 may be any surgical instrument without departing from the teachings of the present disclosure.

In an example embodiment, the second instrument 344 may be configurable to receive an electric current (e.g., second electric current) applied from a second energy source (not shown) so as to perform actions of an electrosurgical instrument. Although the second instrument may be described above and in the present disclosure to receive an electric current, it is to be understood that the second instrument may also be configurable to receive a voltage potential, thermal energy, heat, cold temperature application, radiation, etc. to perform the said surgical action without departing from the teachings of the present disclosure.

The second instrument assembly may also comprise a second instrument driven portion (e.g., second instrument driven portion 344a). The second instrument driven portion 344a may be configurable to be driven by the second instrument drive portion 334a of the integrated motor 334. The second instrument driven portion 344a may be driven by the second instrument drive portion 334a in such a way as to move the second instrument 344. For example, the second instrument driven portion 344a may be driven to move the second instrument 344 relative to the first axis (e.g., axis A). In this regard, such movement of the second instrument 344 may be a rotation of a distal end of the second instrument 344 relative to a proximal end of the second instrument 344, and such proximal end may serve as a pivot for such movement.

The second instrument driven portion 344a may be any mechanism, device, or the like, configurable to be driven by the second instrument drive portion 334a. For example, the second instrument driven portion 344a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one second instrument driven portion, it is to be understood in the present disclosure that the end-effector assembly may have more than one second instrument driven portions without departing from the teachings of the present disclosure.

In example embodiments wherein the end-effector assembly 340 is detachable (i.e., unsecurable) from the arm assembly 330, it is to be understood that the second instrument drive portion 334a of the integrated motor 334 may be operable to drive the second instrument driven portion 344a when the end-effector assembly 340 is secured (i.e., attached) to the arm assembly 330. Specifically, the second instrument drive portion 334a of the integrated motor 334 may be operable to drive the second instrument driven portion 344a when the wrist connector portion 338 is secured (i.e., attached) to the wrist assembly (as further described below and in the present disclosure) of the end-effector assembly (and more specifically, the connector 348 of the end-effector assembly 340).

In example embodiments wherein the end-effector assembly 340 is detachable (i.e., unsecurable) from the arm assembly 330, it is to be understood that one or more connectable and unconnectable electric wires, cables, or the like, may be provided to enable the second instrument 344 to receive the electric current from the energy source to perform the actions of an electrosurgical instrument.

The second instrument assembly may also comprise a second instrument insulative portion (e.g., second instrument insulative portion 344b). The second instrument insulative portion 344b may be providable between the second instrument 344 and one or more portions of the end-effector assembly 340 so as to electrically isolate (or electrically insulate, thermally isolate, thermally insulate, and the like) the second instrument 344 from the one or more portions of the end-effector assembly 340. In an example embodiment, the second instrument insulative portion 344b may be providable between the second instrument 344 and the second instrument driven portion 344a so as to electrically isolate (or electrically insulate, thermally isolate, thermally insulate, and the like) the second instrument 344 from the second instrument driven portion 344a. Such electric isolation (or electric insulation, thermal isolation, thermal insulation, and the like) may be desirable to protect electrically (or thermally) sensitive components/portions of the surgical arm assembly and/or also prevent such electric current (or voltage potential, thermal energy, heat, cold temperature application, radiation, etc.) from undesirably passing through to the first instrument 342 via the second instrument driven portion 344a and/or other component/portion of the surgical arm assembly.

The second instrument insulative portion 344b may be formed using any one or more of a plurality of materials, such as electrically insulative materials, thermally insulative materials, plastics, elastomers, ceramics, glasses, and minerals. It is to be understood in the present disclosure that other materials may also be used without departing from the teachings of the present disclosure.

The second instrument 344 may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), cobalt-chromium alloys, and magnesium alloys. It is to be understood in the present disclosure that other materials may also be used without departing from the teachings of the present disclosure. Furthermore, the second instrument 344 may include an opening, or the like, for use in receiving and housing at least a portion of the second instrument insulative portion 344b. The first axis (e.g., axis A) may be formed through a center of the opening of the second instrument 344 in example embodiments. Although the opening may be depicted in the figures to be circular in shape and the corresponding exterior portion of the second instrument insulative portion 344b being housed in the opening may be depicted in the figures to be circular in shape, it is to be understood in the present disclosure that the opening and such corresponding exterior portion may be formed in one or more other shapes, including, but not limited to, a square, rectangle, oval, pentagon, hexagon, etc., without departing from the teachings of the present disclosure.

(iii) Cooperation of the First Instrument Assembly and Second Instrument Assembly.

In example embodiments, the first instrument (e.g., first instrument 342) and second instrument (e.g., second instrument 344) may be selectively moveable/drivable independently from one another. In example embodiments, the first instrument 342 and the second instrument 344 may be selectively moveable/drivable in a similar or same manner, such as being moveable/driveable at the same time, for the same duration, for the same distance, and/or with the same output energy. Although the figures illustrate end-effector assembly having a first instrument and a second instrument, it is to be understood in the present disclosure that the end-effector assembly may have more other instruments or may only have a first instrument or a second instrument without departing from the teachings of the present disclosure. For example, the first instrument 342 and the second instrument 344 may cooperate to form a grasper. As another example, the first instrument 342 and the second instrument 344 may cooperate to form scissors. As another example, the first instrument 342 and the second instrument 344 may cooperate to form a Maryland grasper. Other forms and types of first instruments and/or second instruments are contemplated in the present disclosure in addition to or in replacement of the first instrument and/or second instrument described above and herein without departing from the teachings of the present disclosure.

For example, as described above, the first instrument 342 may be configurable to receive an electric current (e.g., first electric current) applied from a first energy source (not shown) so as to perform actions of an electrosurgical instrument. In addition to or in replacement, the second instrument 344 may be configurable to receive an electric current (e.g., second electric current) applied from a second energy source (not shown). The first current may be the same in magnitude as but opposite in direction to the second current in example embodiments, and the first energy source may be the same as or different from the second energy source in example embodiments. In such embodiments where the first instrument and second instrument collectively cooperate to form a monopolar electrosurgical instrument, or the like, when a mass (e.g., a tissue mass) is provided between the first instrument 342 and second instrument 344 and an electric current is applied to the first instrument 342 or the second instrument 344, the mass will serve to enable the applied electric current to pass through and aid in cutting, coagulating, desiccating, and/or fulgurating the mass. Similarly, in embodiments where the first instrument and second instrument collectively cooperate to form a bipolar electrosurgical instrument, or the like, when a mass (e.g., a tissue mass) is provided between the first instrument 342 and second instrument 344 and an electric current is applied to the first instrument 342 and the second instrument 344, the mass will serve to enable the applied electric current to pass through and aid in performing a surgical action, including cutting, coagulating, desiccating, cauterizing, and/or fulgurating the mass. Although the first instrument and/or second instrument may be described above and in the present disclosure to receive an electric current, it is to be understood that the first instrument and/or second instrument may also be configurable to receive a voltage potential, thermal energy, heat, cold temperature application, radiation, etc. to perform the said surgical action without departing from the teachings of the present disclosure.

(iv) Wrist Assembly.

The wrist assembly may be securable or secured to the instrument assembly 237 in example embodiments. The wrist assembly may comprise a wrist driven portion (e.g., wrist driven portion 346a). The wrist assembly may further comprise a connector (e.g., connector 348).

The wrist driven portion 346a may be configurable to be driven by the wrist drive portion 336a via the integrated motor 336. The wrist driven portion 346a may be driven by the wrist drive portion 336a in such a way as to move the instrument assembly 237, including the first instrument 342 and/or second instrument 344. For example, the wrist driven portion 346a may be driven to pivotally move the first instrument 342 relative to a second axis (e.g., axis B). In this regard, such movement of the first instrument 342 may be a rotation (or pivotal movement) of a distal end of the first instrument 342 relative to a point on the second axis (e.g., axis B), and such point may serve as a pivot for such movement. In addition to or in replacement, the wrist driven portion 346a may be driven by the wrist drive portion 336a in such a way as to move the second instrument 344. For example, the wrist driven portion 346a may be driven to pivotally move the second instrument 344 relative to the second axis (e.g., axis B). In this regard, such movement of the second instrument 344 may be a rotation (or pivotal movement) of a distal end of the second instrument 344 relative to a point on the second axis (e.g., axis B), and such point may serve as a pivot for such movement. In example embodiments, the wrist driven portion 346a may be driven by the wrist drive portion 336a in such a way as to collectively move the first instrument 342 and the second instrument 344. For example, the wrist driven portion 346a may be driven to collectively move the first instrument 342 and the second instrument 344 relative to the second axis (e.g., axis B). In this regard, such movement of the first instrument 342 and the second instrument 344 may be a collective rotation (or pivotal movement) of a distal end of the first instrument 342 and distal end of the second instrument 344 relative to a point on the second axis (e.g., axis B), and such point may serve as a pivot for such movement. Axis B may be different from axis A (e.g., axis B may be substantially orthogonal to axis A).

The wrist driven portion 346a may be any mechanism, device, or the like, configurable to be driven by the wrist drive portion 336a. For example, the wrist driven portion 346a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an end-effector assembly having one wrist driven portion, it is to be understood in the present disclosure that the end-effector assembly may have more than one wrist driven portions without departing from the teachings of the present disclosure.

Arm Assemblies (e.g., First Arm Assembly 330, Second Arm Assembly 360).

(i) First Arm Assembly (e.g., First Arm Assembly 330).

Figure 5J:
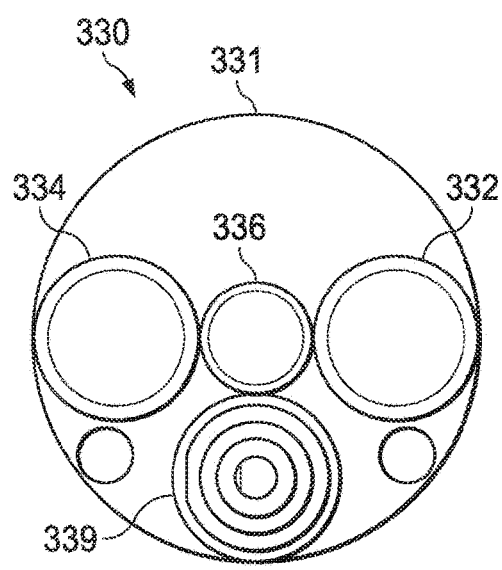
FIG. 5J is an illustration of a top cross-sectional view of an example embodiment of an arm assembly.
Figure 5K:
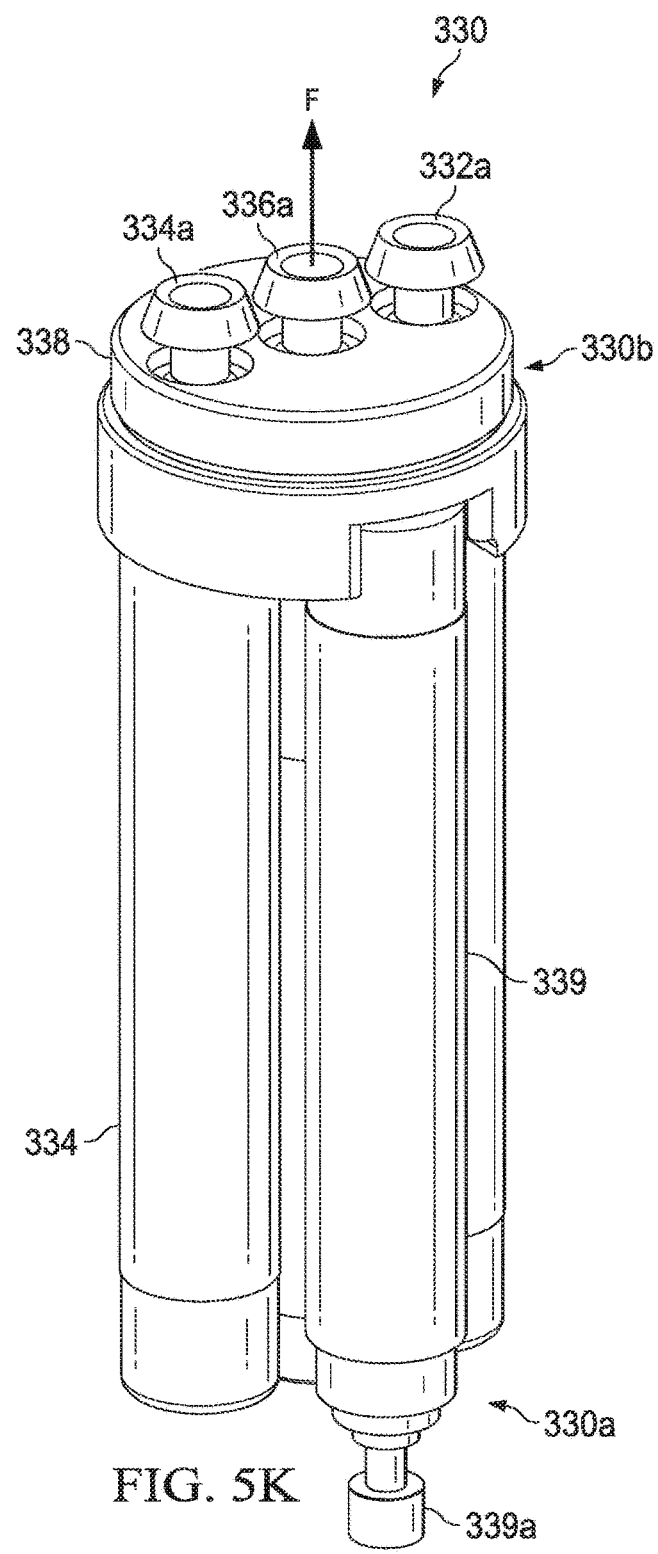
FIG. 5K is an illustration of a perspective view of an example embodiment of an arm assembly.
Figure 5L:
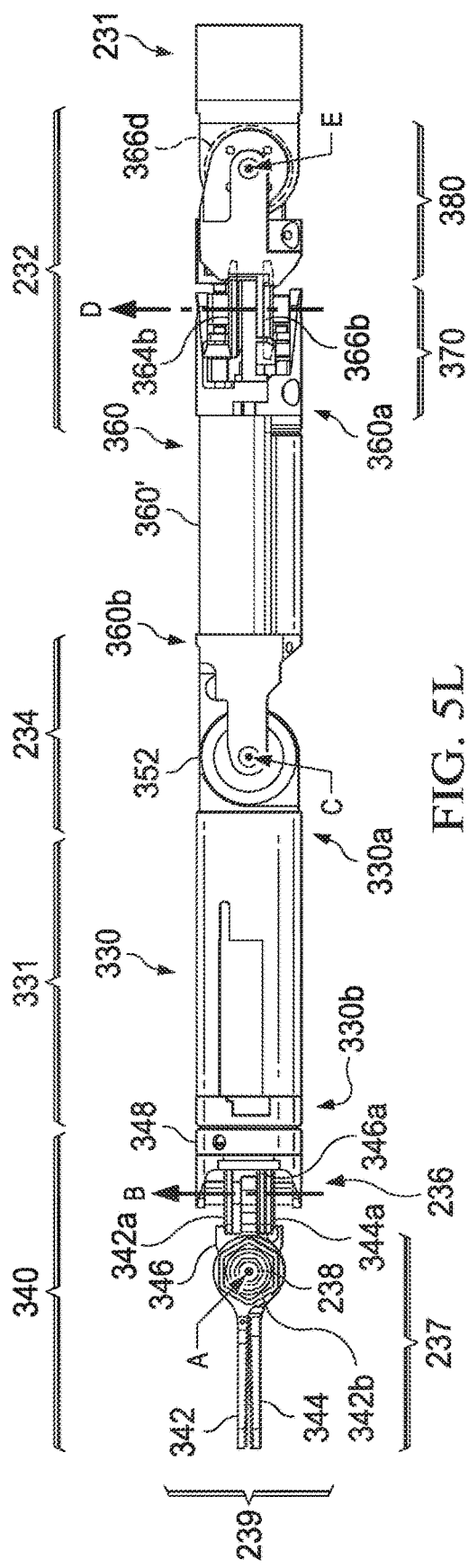
FIG. 5L is an illustration of a side view of an example embodiment of an instrument arm assembly.
Figure 5M:
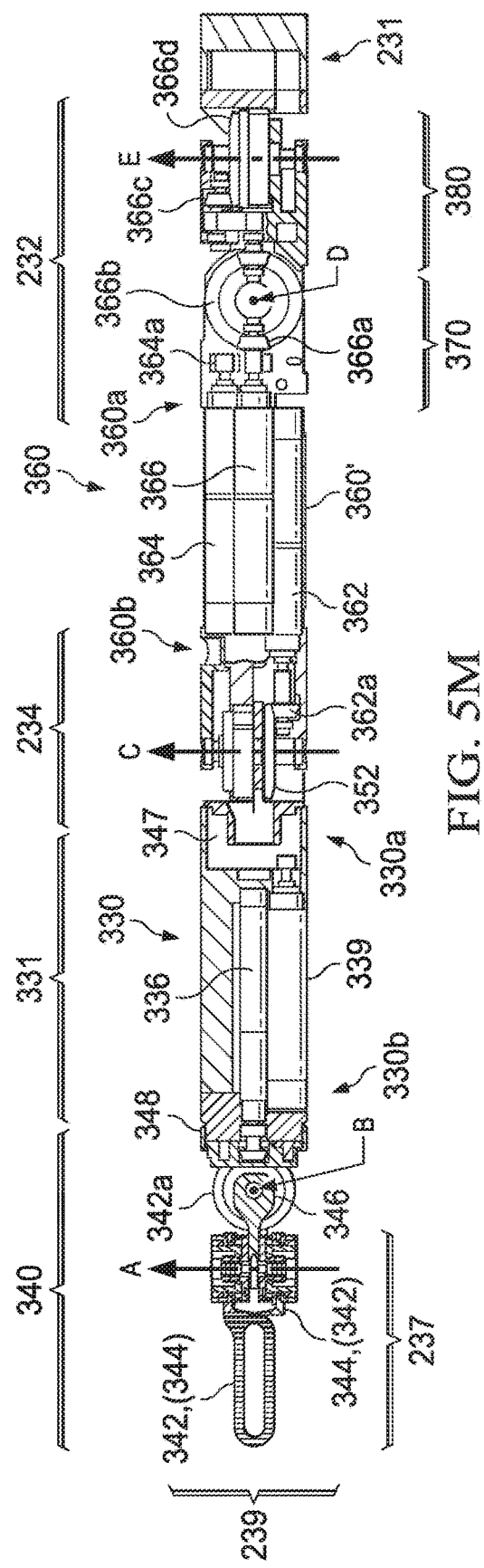
FIG. 5M is an illustration of a side cross-sectional view of an example embodiment of an instrument arm assembly.
Figure 5O:
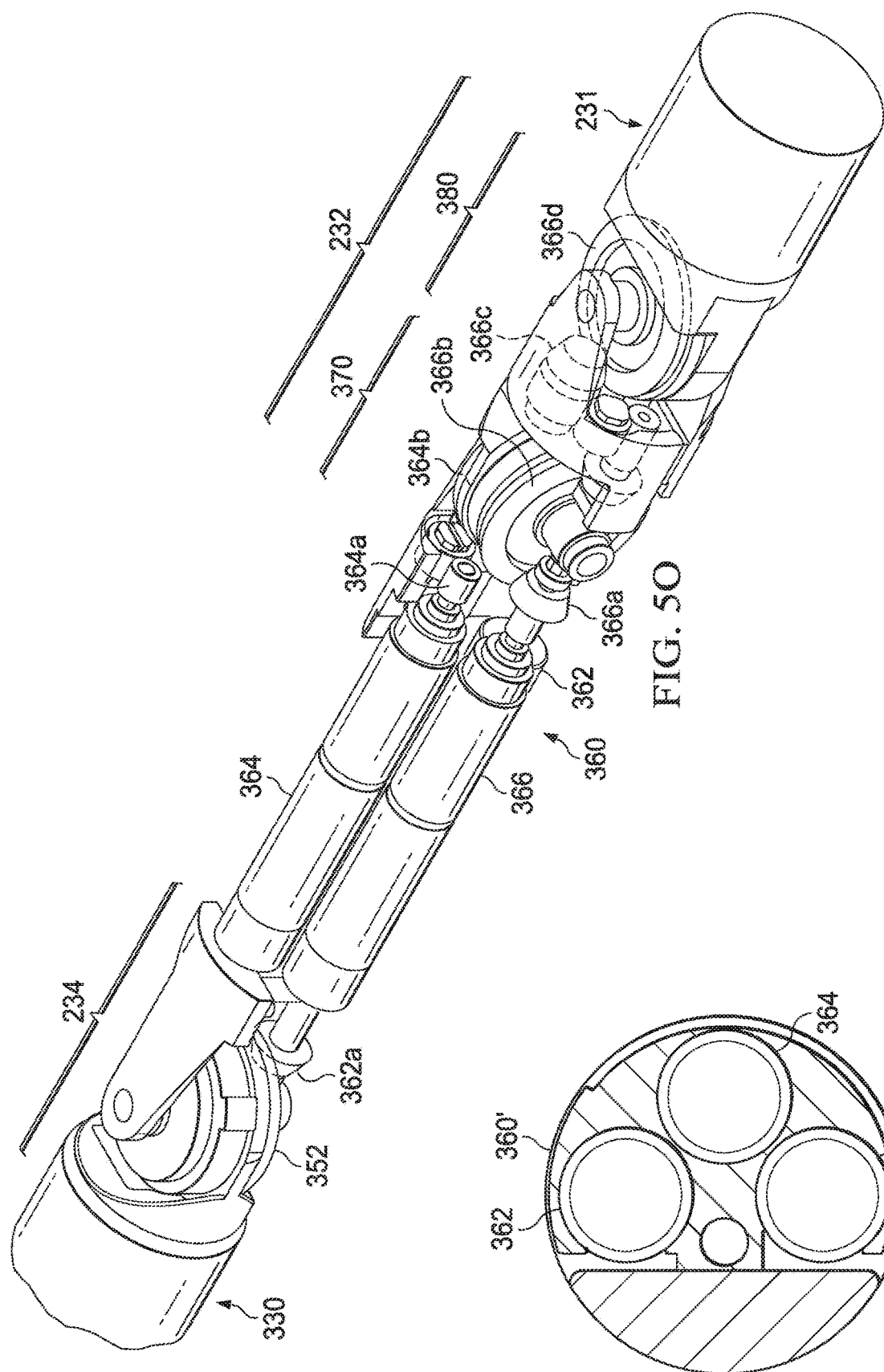
FIG. 5O is an illustration of a transparent perspective partial view of an example embodiment of an instrument arm assembly.
Figure 5N:
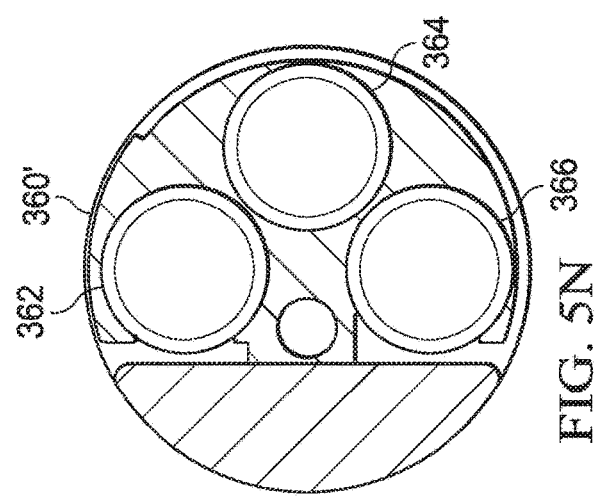
FIG. 5N is an illustration of a top cross-sectional view of an example embodiment of a second arm assembly.

An example embodiment of the first arm assembly 330 is illustrated in at least FIGS. 5A-C, 5L-M, and 5S-T. The arm assembly 330 may be securable to the end-effector assembly 340. In an example embodiment, the arm assembly 330 may be securable to and unsecurable from (e.g., detached) the end-effector assembly 340. As illustrated in FIGS. 5C and 5J, the arm assembly 330 may include an arm assembly body (e.g., arm assembly body 331), a first end 330a (or proximal end), and a second end 330b (or distal end) opposite to the first end 330a. The elbow pitch joint portion 350' may be secured to the first end 330a and the end-effector assembly 340 may be secured to the second end 330b. The wrist connector portion 338 may be provided at the second end 330b. The arm assembly body 331 may securely house one or more of a plurality of drive assemblies.

In an example embodiment, the arm assembly body 331 may securely house a first instrument drive assembly. The first instrument drive assembly may include a first integrated motor (e.g., first integrated motor 332), and may also include a first instrument drive portion (e.g., first instrument drive portion 332a). The first instrument drive portion 332a may be provided at the second end 330b of the arm assembly body 331. The first instrument drive portion 332a may be controllable by the first integrated motor 332 to drive the first instrument driven portion 342a when the wrist connector portion 338 is secured to the wrist assembly. The first instrument drive portion 332a may be any mechanism, device, or the like, configurable to drive the first instrument driven portion 342a. For example, the first instrument drive portion 332a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one first instrument drive portion 332a, it is to be understood in the present disclosure that the arm assembly may have more than one first instrument drive portions 332a without departing from the teachings of the present disclosure.

The arm assembly body 331 may also securely house a second instrument drive assembly in example embodiments. The second instrument drive assembly may include a second integrated motor (e.g., second integrated motor 334), and may also include a second instrument drive portion (e.g., second instrument drive portion 334a). The second instrument drive portion 334a may be provided at the second end 330b of the arm assembly body 331. The second instrument drive portion 334a may be controllable by the second integrated motor 334 to drive the second instrument driven portion 344a when the wrist connector portion 338 is secured to the wrist assembly. The second instrument drive portion 334a may be any mechanism, device, or the like, configurable to drive the second instrument driven portion 344a. For example, the second instrument drive portion 334a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one second instrument drive portion 334a, it is to be understood in the present disclosure that the arm assembly may have more than one second instrument drive portions 334a without departing from the teachings of the present disclosure.

The arm assembly body 331 may also securely house a wrist drive assembly in example embodiments. The wrist drive assembly may include a third integrated motor (e.g., third integrated motor 336), and may also include a wrist drive portion (e.g., wrist drive portion 336a). The wrist drive portion 336a may be provided at the second end 330b of the arm assembly body 331. The wrist drive portion 336a may be controllable by the third integrated motor 336 to drive the wrist driven portion 346a when the wrist connector portion 338 is secured to the wrist assembly. The wrist drive portion 336a may be any mechanism, device, or the like, configurable to drive the wrist driven portion 346a. For example, the wrist drive portion 336a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one wrist drive portion 336a, it is to be understood in the present disclosure that the arm assembly may have more than one wrist drive portions 336a without departing from the teachings of the present disclosure.

The arm assembly body 331 may also securely house a first arm assembly drive assembly in example embodiments. The first arm assembly drive assembly may include a fourth integrated motor (e.g., fourth integrated motor 339), and may also include a first arm assembly drive portion (e.g., first arm assembly drive portion 339a). The first arm assembly drive portion 339a may be provided at the first end 330a of the arm assembly body 331. The first arm assembly drive portion 339a may be controllable by the fourth integrated motor 339 to drive the first arm assembly driven portion 347 to drive the first arm assembly body 331 to move relative to an axis (e.g., axis F illustrated in FIG. 5K). Axis F may be formed by the first arm assembly 330 (e.g., axis F may be formed by a center line drawn through the first arm assembly body 331). The first arm assembly drive portion 339a may be any mechanism, device, or the like, configurable to drive the first arm assembly body 331 to move relative to the first arm assembly joint portion 350. For example, the first arm assembly drive portion 339a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate an arm assembly having one first arm assembly drive portion 339a, it is to be understood in the present disclosure that the arm assembly may have more than first arm assembly drive portions 339a without departing from the teachings of the present disclosure.

Although the figures illustrate the first arm assembly 330 having the first integrated motor 332, second integrated motor 334, third integrated motor 336, fourth integrated motor 339, first instrument drive portion 332a, second instrument drive portion 334a, wrist drive portion 336a, and first arm assembly drive portion 339a, it is to be understood that the first arm assembly 330 may (or may not) include the first integrated motor 332, second integrated motor 334, third integrated motor 336, fourth integrated 339, first instrument drive portion 332a, second instrument drive portion 334a, wrist drive portion 336a, and/or first arm assembly drive portion 339a, and/or may also include other integrated motor(s) and/or other drive portions, without departing from the teachings of the present disclosure. It is also to be understood that the first integrated motor 332, second integrated motor 334, third integrated motor 336, fourth integrated motor 339, first instrument drive portion 332a, second instrument drive portion 334a, wrist drive portion 336a, and/or first arm assembly drive portion 339a may be located, in part or in whole, in the first arm assembly 330, second arm assembly 360, and/or any other location or element of the arm assembly 230 without departing from the teachings of the present disclosure.

(ii) Second Arm Assembly (e.g., Second Arm Assembly 360)

An example embodiment of the second arm assembly 360 is illustrated in at least FIGS. 5A-C, 5L-M, and 5S-T. The second arm assembly 360 may be securable to the first arm assembly 330 on one end (via the elbow sway joint portion 350 and/or elbow pitch joint portion 350') and securable to the shoulder section 231 on another end (via the shoulder sway joint portion 380 and/or shoulder pitch joint portion 370). When secured to the shoulder section 231, the second arm assembly 360 may be configurable to move in one or more of a plurality of ways relative to the shoulder section 231, including, but not limited to, pitch, yaw, and/or roll relative to the shoulder section 231. In an example embodiment, the second arm assembly 360 may be securable to and unsecurable from (e.g., detached) the first arm assembly 330. As illustrated in at least FIGS. 5L-N and 5S-U, the second arm assembly 360 may include a second arm assembly body or housing (e.g., second arm assembly body 360'), a first end 360a (or proximal end), and a second end 360b (or distal end) opposite to the first end 360a. The elbow sway joint portion 350 or elbow pitch joint portion 350' may be secured to the second end 360b. The shoulder pitch joint portion 370 or shoulder sway joint portion 380 may be secured to the first end 360a. As illustrated in at least FIGS. 5S and 5T, in an example embodiment, an end of the elbow sway joint portion 350 (e.g., proximal end) may be secured to the second arm assembly 360 (e.g., distal end, such as second end 360b), another end of the elbow sway joint portion 350 (e.g., distal end) may be secured to the elbow pitch joint portion 350' (e.g., proximal end), an end of the elbow pitch joint portion 350' (e.g., distal end) may be secured to the first arm assembly 330 (e.g., proximal end, such as first end 330a), an end of the shoulder pitch joint portion 370 (e.g., distal end) may be secured to the second arm assembly 360 (e.g., proximal end, such as first end 360a), another end of the shoulder pitch joint portion 370 (e.g., proximal end) may be secured to the shoulder sway joint portion 380 (e.g., distal end), and an end of the shoulder sway joint portion 380 (e.g., proximal end) may be secured to the shoulder section 231 (e.g., distal end). The second arm assembly body 360' may securely house one or more of a plurality of drive assemblies.

In an example embodiment, the second arm assembly body 360' may securely house an elbow pitch drive assembly. The elbow pitch drive assembly may include a fifth integrated motor (e.g., fifth integrated motor 362), and may also include an elbow pitch drive portion (e.g., elbow pitch drive portion 362a'). The elbow pitch drive portion 362a' may be provided at the second end 360b (e.g., distal end) of the second arm assembly 360. The elbow pitch drive portion 362a' may be controllable by the fifth integrated motor 362 to drive the elbow pitch driven portion 352'. The elbow pitch drive portion 362a' may be any mechanism, device, or the like, configurable to drive the elbow pitch driven portion 352'. In an example embodiment, the elbow pitch drive portion 362a' may be configurable to drive the elbow pitch driven portion 352' so as to cause the first arm assembly 330 to pivotally move or rotate relative to an axis (e.g., axis C'). Put differently, the fifth integrated motor 362 may be configurable to pivotally move or rotate the first arm assembly 330 relative to the second arm assembly 360 and/or elbow sway joint portion 350 (and with respect to axis C'). For example, the elbow pitch drive portion 362a' may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one elbow pitch drive portion 362a', it is to be understood in the present disclosure that the second arm assembly may have more than one elbow drive portions 362a without departing from the teachings of the present disclosure.

The second arm assembly body 360' may also securely house an elbow sway drive assembly. The elbow sway drive assembly may include a sixth integrated motor (e.g., sixth integrated motor 369), and may also include an elbow sway drive portion (e.g., elbow sway drive portion 362a). The elbow sway drive portion 362a may be provided at the second end 360b (e.g., distal end) of the second arm assembly 360. The elbow sway drive portion 362a may be controllable by the sixth integrated motor 369 to drive the elbow sway driven portion 352. The elbow sway drive portion 362a may be any mechanism, device, or the like, configurable to drive the elbow sway driven portion 352. In an example embodiment, the elbow sway drive portion 362a may be configurable to drive the elbow sway driven portion 352 so as to cause the first arm assembly 330 to pivotally move or rotate relative to an axis (e.g., axis C). Put differently, the sixth integrated motor 369 may be configurable to pivotally move or rotate the elbow pitch joint portion 350' (and consequently the first arm assembly 330) relative to the second arm assembly 360 (and with respect to axis C). The axis C may be different from axis C'. In an example embodiment, axis C may be substantially orthogonal to axis C'. The elbow sway drive portion 362a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one elbow sway drive portion 362a, it is to be understood in the present disclosure that the second arm assembly may have more than one elbow sway drive portions 362a without departing from the teachings of the present disclosure.

The second arm assembly body 360' may also securely house a shoulder pitch drive assembly in example embodiments. The shoulder pitch drive assembly may include a seventh integrated motor (e.g., seventh integrated motor 364) and a shoulder pitch drive portion (e.g., shoulder pitch drive portion 364a). The shoulder pitch drive portion 364a may be provided at the first end 360a (e.g., proximal end) of the second arm assembly 360. The shoulder pitch drive portion 364a may be controllable by the seventh integrated motor 364 to drive the shoulder pitch driven portion 364b. The shoulder pitch drive portion 364a may be any mechanism, device, or the like, configurable to drive the shoulder pitch driven portion 364b. In an example embodiment, the shoulder pitch drive portion 364a may be configurable to drive the shoulder pitch driven portion 364b so as to cause the second arm assembly 360 to pivotally move or rotate relative to an axis (e.g., axis D). Put differently, the seventh integrated motor 364 may be configurable to pivotally move or rotate the second arm assembly 360 relative to the shoulder sway joint portion 380 (and/or shoulder section 231) (and with respect to axis D). For example, the shoulder pitch drive portion 364a may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one shoulder pitch drive portion 364a, it is to be understood in the present disclosure that the second arm assembly may have more than one shoulder pitch drive portions 364a without departing from the teachings of the present disclosure.

The second arm assembly body 360' may also securely house a shoulder sway drive assembly in example embodiments. The shoulder sway drive assembly may include an eighth integrated motor (e.g., eighth integrated motor 366) and a shoulder sway drive portion (e.g., shoulder sway drive portion 366a). The shoulder sway drive portion 366a may be provided at the first end 360a (e.g. proximal end) of the second arm assembly 360. The shoulder sway drive portion 366a may be controllable by the eighth integrated motor 366 to drive the shoulder sway driven portion 366b, 366c, and/or 366d. The shoulder sway drive portion 366a may be any mechanism, device, or the like, configurable to drive the first shoulder sway driven portion 366b. In an example embodiment, the shoulder sway drive portion 366a may be configurable to drive the shoulder sway driven portion 366b, 366c, and/or 366d so as to cause the second arm assembly 360 to pivotally move or rotate relative to an axis (e.g., axis E). Put differently, the eighth integrated motor 366 may be configurable to pivotally move or rotate the shoulder pitch joint portion 370 (and/or the second arm assembly 360) relative to the shoulder section 231 (and with respect to axis E). The axis E may be different from axis D. In an example embodiment, axis E may be substantially orthogonal to axis D. One or more of the shoulder sway drive portion 366a, first shoulder sway driven portion 366b, second shoulder sway driven portion 366c, and third shoulder sway driven portion 366d may comprise any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate a second arm assembly having one shoulder sway drive portion 366a, one first shoulder sway driven portion 366b, one second shoulder sway driven portion 366c, one third shoulder sway driven portion 366d, it is to be understood in the present disclosure that the second arm assembly may have more than one shoulder sway drive portions 366a, more than one first shoulder sway driven portion 366b, more than one second shoulder sway driven portions 366c, and/or more than one third shoulder sway driven portions 366d without departing from the teachings of the present disclosure. Furthermore, it is to be understood in the present disclosure that the second arm assembly may or may not have second shoulder sway driven portion 366c, and/or may or may not have one or more additional or other intermediate shoulder sway driven portions between the shoulder sway drive portion 366a and the third shoulder sway driven portion 366d without departing from the teachings of the present disclosure.

Although the figures illustrate the second arm assembly 360 having the fifth integrated motor 362, sixth integrated motor 369, seventh integrated motor 364, eighth integrated motor 366, elbow pitch drive portion 362a', elbow sway drive portion 362a, shoulder pitch drive portion 364a, and shoulder sway drive portion 366a, it is to be understood that the second arm assembly 360 may or may not include the fifth integrated motor 362, sixth integrated motor 369, seventh integrated motor 364, eighth integrated motor 366, elbow pitch drive portion 362a', elbow sway drive portion 362a, shoulder pitch drive portion 364a, and/or shoulder sway drive portion 366a, and/or may also include other integrated motor(s) and/or other drive portions, without departing from the teachings of the present disclosure. It is also to be understood that the fifth integrated motor 362, sixth integrated motor 369, seventh integrated motor 364, eighth integrated motor 366, elbow pitch drive portion 362a', elbow sway drive portion 362a, shoulder pitch drive portion 364a, and/or shoulder sway drive portion 366a may be located, in part or in whole, in the first arm assembly 330, second arm assembly 360, and/or any other location or element of the arm assembly 230 without departing from the teachings of the present disclosure.

Each of the instrument arm assemblies may be securable to (and unsecured from) the anchor ports 216 of the port assembly 210 via a securing portion 231a of the shoulder section 231. It is recognized in the present disclosure that the instrument arm assembly 230, 240 may be secured to the anchor port 216 of the port assembly 210 in the forward-directed position (e.g., as illustrated in FIGS. 2B, 2D, 3B, and 3D) and/or the reverse-directed position (e.g., as illustrated in FIGS. 2A, 2C, 3A, and 3C). Furthermore, in example embodiments, the instrument arm assembly 230, 240 may or may not be transitionable between the forward-directed position and the reverse-directed position. In example embodiments where the instrument arm assembly 230, 240 is transitionable between the forward-directed position and the reverse-directed position, such transition may be performable before, during, and/or after the securing of the shoulder section 231 to the anchor port 216 of the port assembly 210. For example, in such embodiments, the securing portion 231a may be adjustably changed in position relative to the shoulder section 231, such as from the forward-directed position illustrated in FIGS. 5A and 5P to the reverse-directed position illustrated in FIGS. 5B and 5Q, and vice versa.

One or more internal temperature control assemblies (not shown) may be provided for each of the one or more instrument arm assemblies 230, 240. Each internal temperature control assembly may be operable to control (such as reduce) the temperature and/or heat emission of the aforementioned gears and/or gear assemblies, motors, instrument joint portions (such as 232, 370, 380, 234, 236, and/or 238), and/or instrument arm segments (such as 231, 360, 330, and/or 340). The one or more internal temperature control assemblies may also be operable to control (such as increase or decrease) the temperature of the end effector 239, 342, 344 (which may be desirable when the end effector 239, 342, 344 is a cutting tool, or the like). In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well any solids (if used), may be provided through an interior of the instrument arm assembly without increasing dimensions (such as diameter) of the instrument arm assembly.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the body cavity, such as via an opening (not shown). When the internal temperature control assembly utilizes liquids, or the like, example embodiments may be operable to discharge or recycle such liquids outside of the body cavity. When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the instrument arm assembly 230, 240.

In example embodiments, the internal temperature control assembly may utilize a combination of gases, liquids, solids, and/or the like without departing from the teachings of the present disclosure.

After the instrument arm assembly 230, 240 has been inserted and attached (or secured) to the port assembly 210, the end effector or instrument 239, 342, 344 may be configurable, either manually and/or via the computing device (or system), to apply between about 0 to 20 N of force via the integrated motors 332, 334 when performing surgical actions and procedures, such as clipping and/or grasping actions. Furthermore, the end effector or instrument 239, 342, 344 may be configurable, either manually and/or via the computing device/controller, to apply between about 0 to 10 N of force via the integrated motors 332, 334, 336, 339 when performing other surgical actions and procedures, such as translational, twisting, pulling, and/or pushing actions. It is to be understood in the present disclosure that the above range of applicable force are merely an illustration of example embodiments, and as such the range of applicable force may be smaller or larger than those recited above without departing from the teachings of the present disclosure.

In an example embodiment, the instrument arm segments, including the shoulder section 231, the second arm assembly 360, the first arm assembly 330, and/or the end-effector assembly 340, may be substantially cylindrical in shape. The instrument arm segments, including the shoulder section 231, the second arm assembly 360, the first arm assembly 330, and/or the end-effector assembly 340, may also be formed in any one of a plurality of other shapes, sizes, and/or dimensions without departing from the teachings of the present disclosure.

As described above, the instrument arm assembly 230, 240 may also include one or more securing portions 231a. The securing portion 231a may be attachable or attached to the first instrument arm segment 231, a part of the first instrument arm segment 231, and/or formed as a unitary article with the first instrument arm segment 231. Such securing portions 231a may be for use in securing the instrument arm assembly 230, 240 to the anchor ports 216. Such securing portions 231a may also be for use in performing or assisting in performing the process of inserting the instrument arm assembly 230, 240 into and securing onto the port assembly 210 in example embodiments.

After the instrument arm assembly 230 is inserted through the port assembly 210 and into the cavity of a patient (such as a vagina or rectum), the securing portion 231a of the first instrument arm segment (or shoulder section) 231 may be securely received by the anchor port 216 of the port assembly 210.

In an example embodiment, the length of the securing portion 231a may be between about 350 to 450 mm, the length of the shoulder section 231 may be between about 15 to 40 mm, the length of the second arm assembly 360 may be between about 80 to 105 mm, the length of the first arm assembly 330 may be between about 65 to 90 mm, the length of the end-effector assembly 340 may be between about 5 to 30 mm, and the overall length of the collective instrument arm may be between about 165 to 265 mm. In example embodiments, the length of the securing portion 231a may be between about 340 to 400 mm, the length of the shoulder section 231 may be between about 15 to 25 mm, the length of the second arm assembly 360 may be between about 90 to 100 mm, the length of the first arm assembly 330 may be between about 75 to 85 mm, the length of the end-effector assembly 340 may be between about 15 to 25 mm, and the overall length of the collective instrument arm may be between about 195 to 235 mm. In example embodiments, a length of one or more of the instrument arm segments, the securing portion 231a, and/or the end effector or instrument 239, 342, 344 may also be adjustable by the computing device (or system) of one or more nearby and/or remotely located surgical teams 904 before, during, and/or after insertion of the instrument arm assembly into the cavity of the patient. The outer diameter of one or more of the instrument arm segments may be about 10 to 16 mm. In an example embodiment, the outer diameter of one or more of the instrument arm segments may be about 16 mm.

Each of the instrument arm assemblies, including the securing portion 231a, the shoulder section 231, the second arm assembly 360, the first arm assembly 330, the instrument assembly 237, the end effector or instrument 239, 342, 344, the shoulder sway joint portion 380 (or joint portion along axis E), the shoulder pitch joint portion 370 (or joint portion along axis D), the elbow pitch joint portion 350' (or joint portion along axis C), the elbow sway joint portion 350 (or joint portion along axis C'), the third joint portion 236 (or joint portion along axis B), and/or the instrument joint 238 (or joint portion along axis A), may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. It is to be understood in the present disclosure that other materials may also be used without departing from the teachings of the present disclosure.

The Assistant Arm Assemblies (e.g., Assistant Arm Assembly 250, 260)

In an example embodiment, the surgical device 200 may comprise one or more assistant arm assemblies (e.g., assistant arm assembly 250 or 260) configurable to be inserted into and attach to the port assembly 210. As illustrated in FIGS. 2A, 2B, 3A, and 3B, one or more of the assistant arm assemblies may be a suction/irrigation assembly 250 or an assistant instrument arm assembly such as a retractor arm assembly 260, and each of them may include a multi-curvable body 252 or 262, respectively, and an anchoring portion, respectively (e.g., similar to the multi-curvable body 222 and anchoring portion 220a of the image capturing assembly 220).

As illustrated in FIGS. 2A, 2B, 3A, and 3B, the suction/irrigation assembly 250 may include an end having a suction port 259 for applying a suction or negative pressure, which may be for use in removing liquids (e.g., blood, etc.) from the cavity of the patient. In respect to the assistant instrument arm assembly 260, the assistant instrument arm assembly 260 may include an end having an instrument 269, such as a gripper, retractor, cutter, needle, or the like, which may be for use in assisting the one or more instrument arm assemblies 230 and/or 240 in performing the surgical action.

As illustrated in the example embodiment of FIGS. 2A, 2B, 3A, and 3B, the assistant arm assemblies 250 and/or 260 may comprise a multi-curvable body 252 and/or 262, respectively, attached to their ends (suction port or instrument, respectively). The multi-curvable body 252 or 262 may be any elongated multi-curvable body similar to that of the image capturing assembly 220 described above and in the present disclosure that can be controlled/configured by the surgical team 904 (such as via the computing device/controller/manipulator/master input device) to, among other things, straighten and/or curve (and hold such a straightness and/or curvature) at one or more of a plurality of locations along the multi-curvable body 252 or 262, curve (and hold such a curvature) in one or more of a plurality of curvatures, and/or straighten and/or curve (and hold such a straightness and/or curvature) in one or more of a plurality of directions. It is to be understood that, when the multi-curvable body 252 or 262 is configured to curve at any location along the multi-curvable body 252 or 262, the curve may be held and/or released (or configured to uncurve, curve less, or straighten) by the surgical team 904 (such as via the computing device/controller/manipulator/master input device).

The multi-curvable body 252 or 262 may be formed in any one or more ways known in the art. For example, the multi-curvable body 252 or 262 may be a unitary or substantially unitary elongated body having a plurality of wires, cables, or the like, distributed/run throughout the multi-curvable body 252 or 262 in such a way that a manipulating, such as a pulling/releasing, shortening/lengthening, tightening/loosening, etc., of one or a combination of such wires, cables, or the like enables the above-mentioned curving of one or more locations of the multi-curvable body 252 or 262 in one or more curvatures and in one or more directions. As another example, the multi-curvable body 252 or 262 may include a plurality of segments, each segment linked to an adjacent segment in such a way that the segment may be controlled/configured to be pivotly positioned in a plurality of positions relative to the adjacent segment. As another example, the multi-curvable body 252 or 262 may include a plurality of springs, gears, motors, etc. for achieving the above-mentioned curving of one or more locations of the multi-curvable body 252 or 262 in one or more curvatures and in one or more directions. It is to be understood in the present disclosure that the multi-curvable body 252 or 262 may also include a combination of one or more of the above-mentioned approaches.

The assistant arm assembly 250 or 260 may be secured to the port assembly 210 in one or more of a plurality of ways, including those described above and in the present disclosure for the instrument arm assemblies 230, 240 and/or the image capturing assembly 220. For example, the assistant arm assembly 250 or 260 may also comprise an anchoring portion (e.g., similar to the anchoring portion 220a of the image capturing assembly 220 and/or the securing portion 231a of the instrument arm assembly 220), respectively, operable to attach (or secure) the assistant arm assembly 250 or 260 to one or more anchor ports 216 of the port assembly 210.

In an example embodiment, the multi-curvable body 252 or 262 may each be substantially cylindrical in shape. The multi-curvable body 252 or 262 may also be formed in any one of a plurality of other shapes, sizes, and/or dimensions without departing from the teachings of the present disclosure.

In an example embodiment, the length of the multi-curvable body 252 or 262 may be between about 170 to 270 mm. In example embodiments, a length of multi-curvable body 252 or 262 may also be adjustable by the surgical team 904 before, during, and/or after insertion of the camera arm assembly into the cavity of the patient. The outer diameter of the multi-curvable body 252 or 262 may be between about 5 to 7 mm. It is to be understood in the present disclosure that the above dimensions are merely an illustration of example embodiments, and as such the dimensions may be smaller or larger than those recited above without departing from the teachings of the present disclosure.

Controller

In example embodiments, the surgical system may include a controller (or computing device, manipulator, and/or master input device). The controller may be configurable to perform one or more of a plurality of operations in and on the surgical system 200. For example, the controller may be configurable to communicate with and/or control one or more elements of the surgical system 200, such as the external anchor 1 or 1000, the port assembly 210, the instrument arm assemblies 230 or 240, the image capturing assembly 220, and/or the assistant arm assemblies 250 or 260. The controller may be accessible and/or controllable by the surgical team 904, and the surgical team may be able to communicate with and/or control the configuring and/or operation of the one or more elements of the surgical system 200. For example, the controller may be configurable to control a movement and action of some or all parts of the instrument arm assemblies 230 or 240, the first gate assembly 212*b*, the second gate assembly 214*b*, the movement and action of some or all parts of the image capturing assembly 220 (including the image capturing, temperature control, etc.), the movement and action of some or all parts of the multi-curvable body 222 of the image capturing assembly 220, the movement and action of some or all parts of the multi-curvable body 252 or 262 of the assistant arm assemblies, the movement and action of some or all parts of the assistant arm assemblies 250 or 260, and the like.

Method of Setting Up the Surgical Device 200 in a Forward-Directed Position (e.g., Method 700)

As illustrated in FIG. 7 and FIGS. 8A-E, example embodiments of the surgical device 200 may be configurable to perform a forward-directed surgical action or procedure in one of a plurality of ways. In an example embodiment, the external anchor 1 may be provided and installed/anchored to the stationary object. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210*a*, secured to the anchor ports 216, and configured in the cavity of the patient. A surgical action or procedure may then be performed in any part, area, and/or quadrant of the cavity of the patient using the surgical device 200. These processes will now be described below with references to at least FIGS. 7, 8A-E, 9B, and 10B.

(1) Providing the External Anchor and Installing the Port Assembly.

In an example embodiment, the external anchor 1 may be provided and installed/anchored to one or more stationary objects, such as a side rail 300 of a surgical table/bed, as illustrated in FIGS. 1A and 1B. One or more segments 2, 6, 10, and 14 of the external anchor 1 may cooperate using one or more joints 4, 8, 12, and 16 of the external anchor 1 to fix the position (including orientation) of the port assembly 210 in or about the opening of the patient.

In an example embodiment, as illustrated in FIGS. 10A and 10B, the external anchor 1 may comprise a controllable swivel assembly 1000 operable to provide one or more additional in vitro degrees of freedom, such as via a first swivel portion 1002, second swivel portion 1004, and/or third swivel portion 1006. The controllable swivel assembly 1000 may further comprise a motor 1002*a* for the first swivel portion 1002, a motor 1004*a* for the second swivel portion 1004, a motor 1006*a* for the third swivel portion 1006, one or more supporting arms 1008, and one or more locks 1010.

The first swivel portion 1002 may be operable to provide, as one of the in vitro degrees of freedom, a translational movement of the port assembly 210 along an axis defined by the elongated length of the port assembly 210, as illustrated by the arrow A. In example embodiments, the translational movement, as illustrated by arrow A, provided by the first swivel portion 1002 may be between about 0 to 50 mm.

The controllable swivel assembly 1000 may further comprise a second swivel portion 1004 operable to provide, as another one of the in vitro degrees of freedom, a torsional or rotational movement of the port assembly 210 about an axis depicted by axis Y. In example embodiments, the torsional or rotational movement, as illustrated by the arrow B, provided by the second swivel portion 1004 may be between about +/−180 degrees.

The controllable swivel assembly 1000 may further comprise a third swivel portion 1006 operable to provide, as another one of the in vitro degrees of freedom, a pivotal or rotational movement of the port assembly 210 about an axis perpendicular to the Y-axis, such as the axis depicted by axis Z (which comes out of the page). In example embodiments, the Z-axis or the center of rotation may be located at about opening of the patient, such as at the mid-point of the abdominal wall. In example embodiments, the pivotal or rotational movement, as illustrated by the arrow C, provided by the third swivel portion 1006 may be between about +/−80 degrees.

It is recognized in the present disclosure that the controllable swivel assembly 1000 may comprise the first swivel portion 1002, second swivel portion 1004, and/or third swivel portion 1006 in example embodiments. The controllable swivel assembly 1000 may further comprise other swivel portions (not shown) when more than three in vitro degrees of freedom and/or movements/rotations other than those providable by the first swivel portion 1002, second swivel portion 1004, and third swivel portion 1006 are desired and/or required.

The controllable swivel assembly 1000, including the first swivel portion 1002, the second swivel portion 1004, and/or the third swivel portion 1006, may be controllable either locally or remotely by the surgical team.

In an example embodiment, the port assembly 210 may be installed and secured to the external anchor 1 or 1000. As illustrated in FIGS. 8A-E, the second end 214 of the port assembly 210 may be inserted into the opening of the patient and into the cavity of the patient and the first end 212 of the port assembly 210 may be secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212*b* and the second gate assembly 214*b* may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 2B:
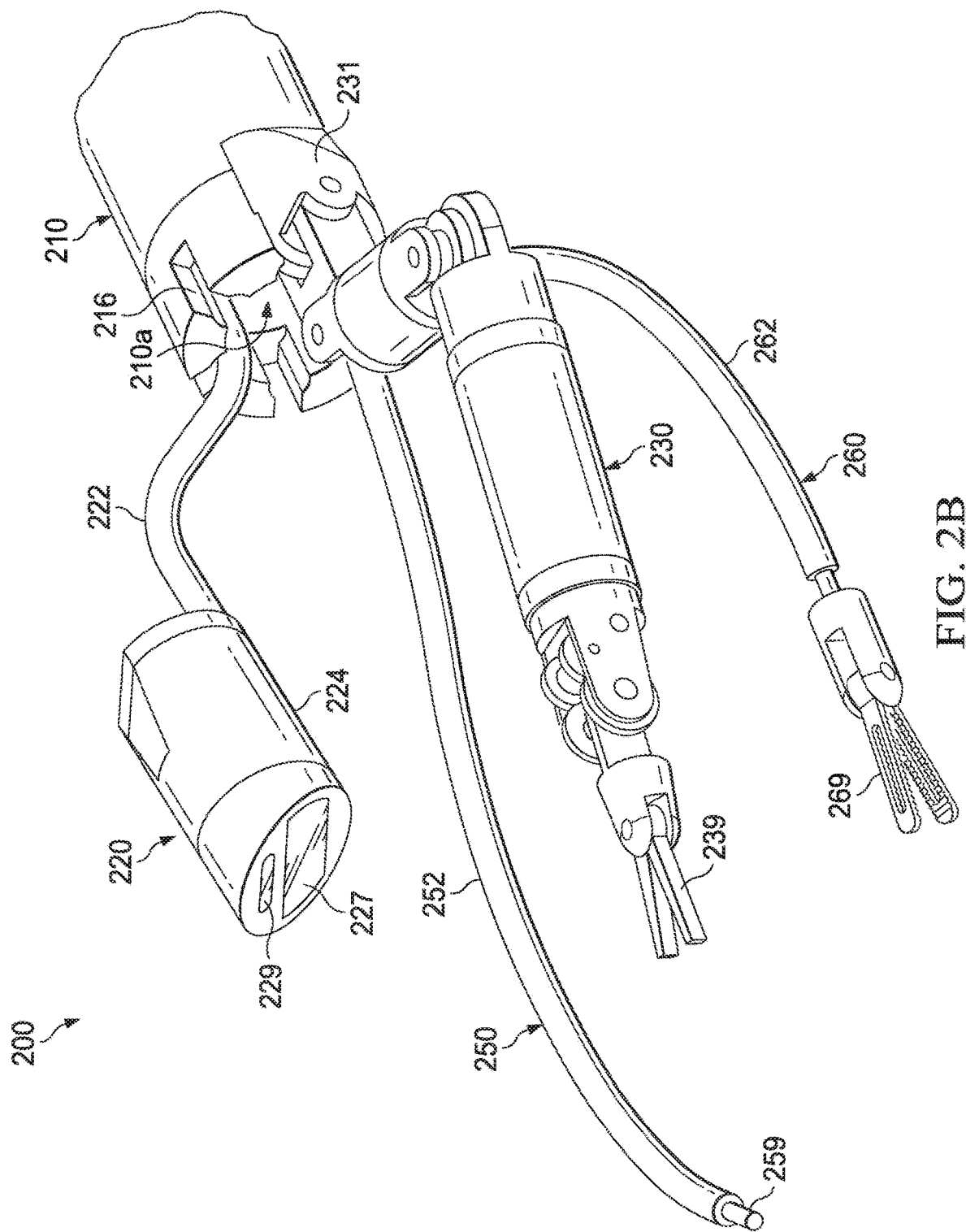
FIG. 2B is an illustration of a perspective view of an example embodiment of a surgical device configured in a forward-directed position.
Figure 2C:
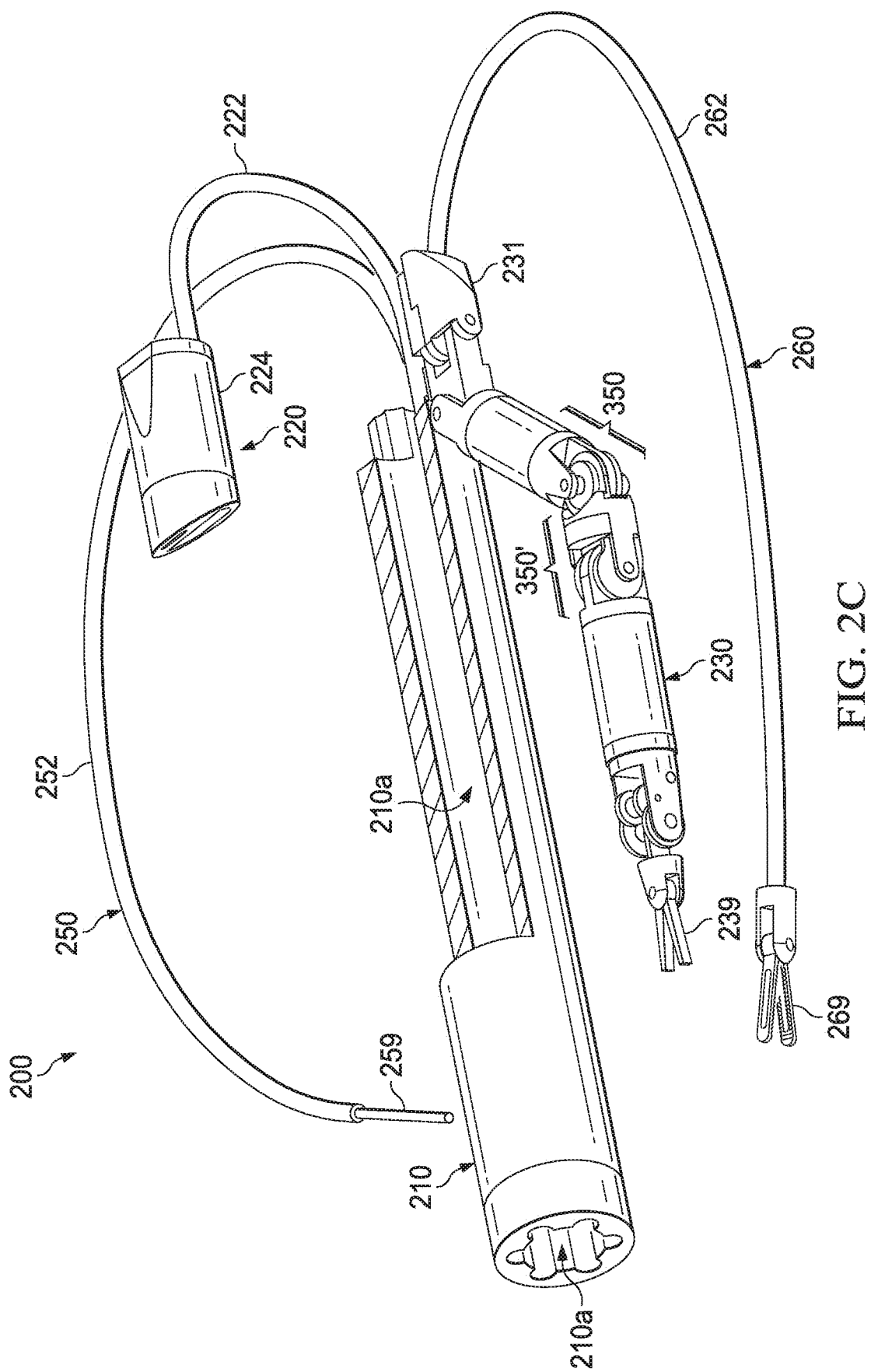
FIG. 2C is another illustration of a perspective view of an example embodiment of a surgical device configured in a reverse-directed position.
Figure 2D:
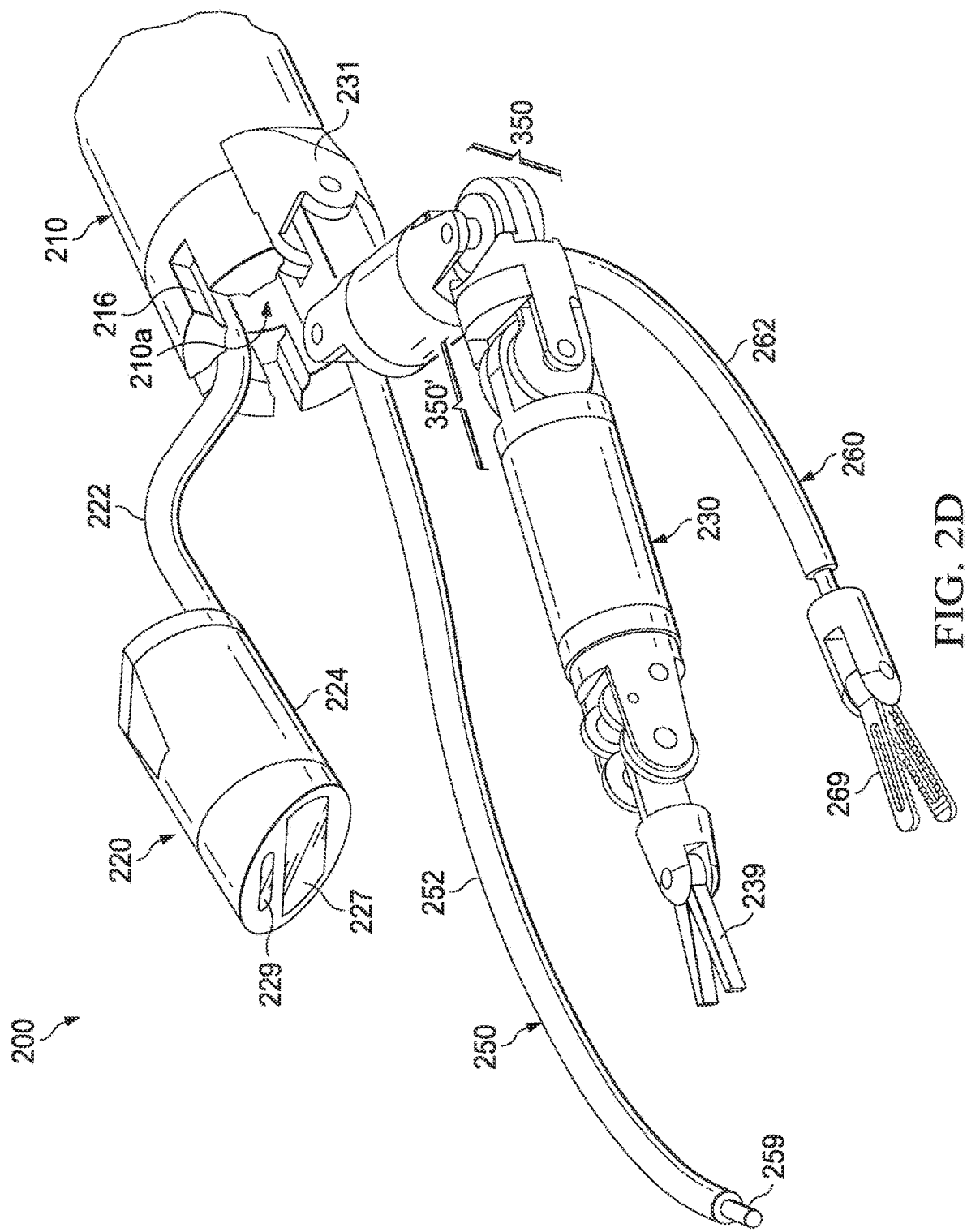
FIG. 2D is another illustration of a perspective view of an example embodiment of a surgical device configured in a forward-directed position.
Figure 8A:
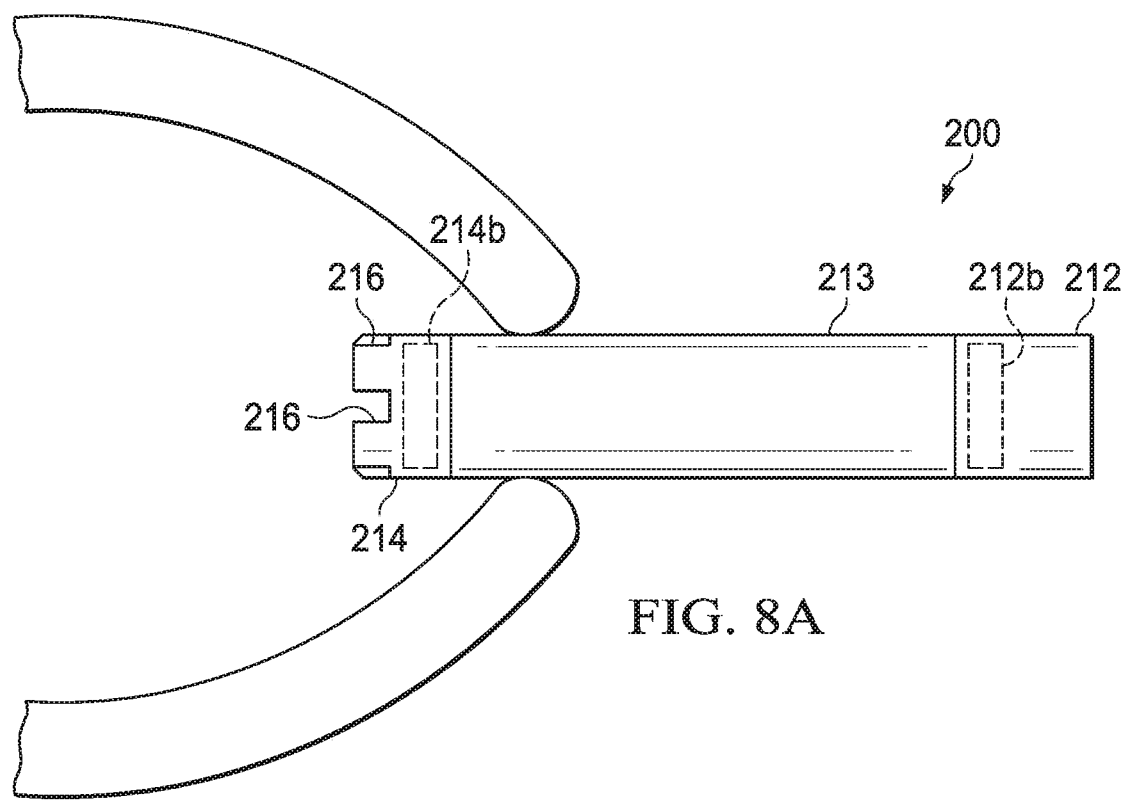
FIGS. 8A-E are illustrations of a side view of an example embodiment of a method of configuring a surgical device in a forward-directed position.

After the workable volume/space in the cavity has been formed and the port assembly 210 is secured in position, as illustrated in FIG. 8A, the image capturing assembly 220 may be inserted through the central access channel 210*a* and secured to the anchor port 216 of the port assembly 210. To do so while maintaining the workable volume/space, the first gate assembly 212*b* may be configured to the open position while the second gate assembly 214*b* is configured to the closed position. Once the first gate assembly 212*b* is in the open position, the image capturing assembly 220 may be inserted into the mid section 213. The first gate assembly 212*b* may then be configured to the closed position after the image capturing assembly 220 passes through the first gate assembly 212*b*. The second gate assembly 214*b* may then be configured to the open position. It is recognized in the present disclosure that the workable volume/space in the cavity is maintained via the insufflation since the first gate assembly 212*b* is configured to the closed position. Once the second gate assembly 214*b* is in the open position, the image capturing assembly 220 may be inserted into the cavity of the patient and the anchor portion 220*a* secured to an anchor port 216. The second gate assembly 214*b* may then be configured to the closed position after the image capturing assembly 220 passes through the second gate assembly 214*b*. The multi-curvable body 222 of the image capturing assembly 220 may then be configured/controlled to curve in one or more locations along the multi-curvable body 222 so that the image capturing assembly 220 can be directed in a forward-directed position (as illustrated in FIGS. 2B and 3B).

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8B:
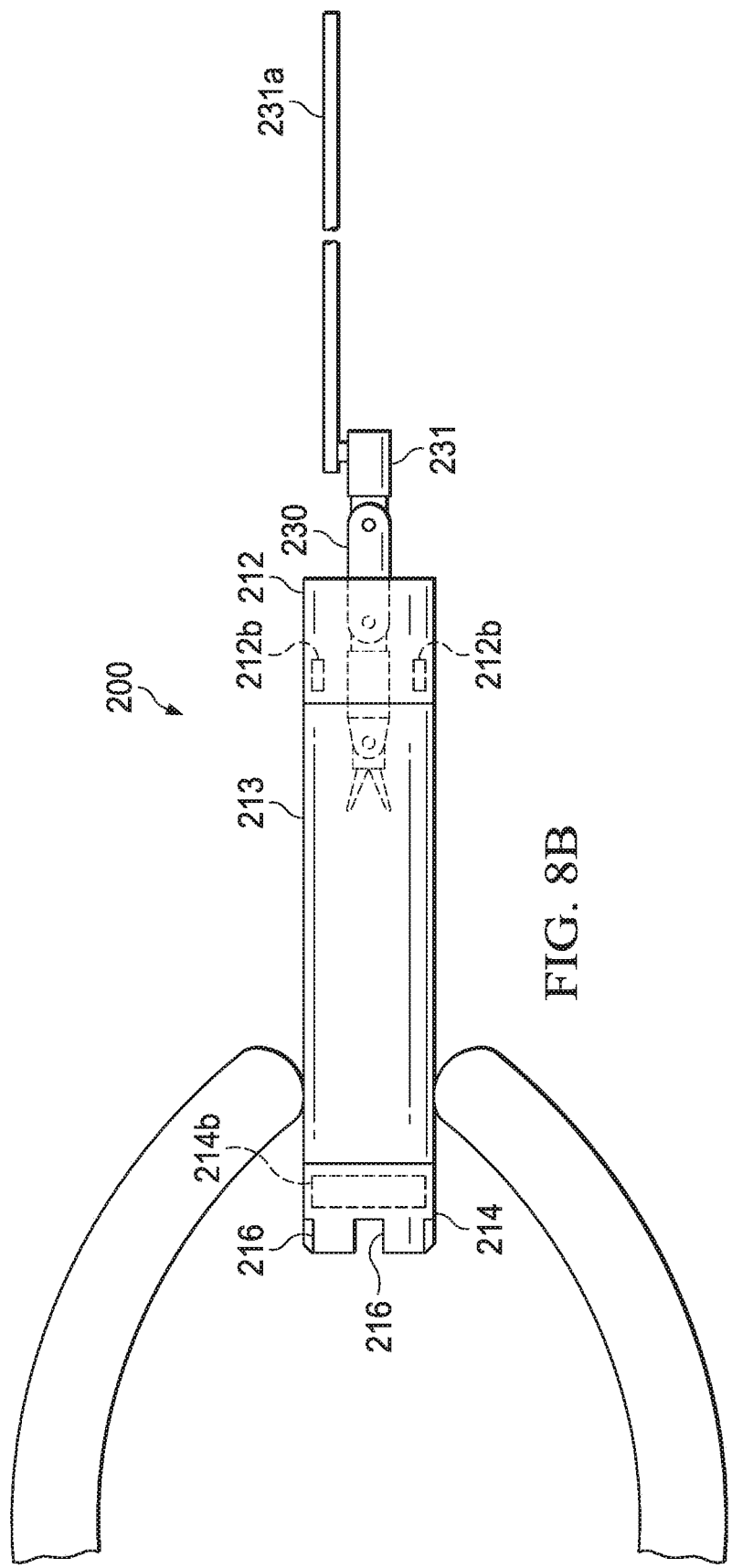
Figure 8C:
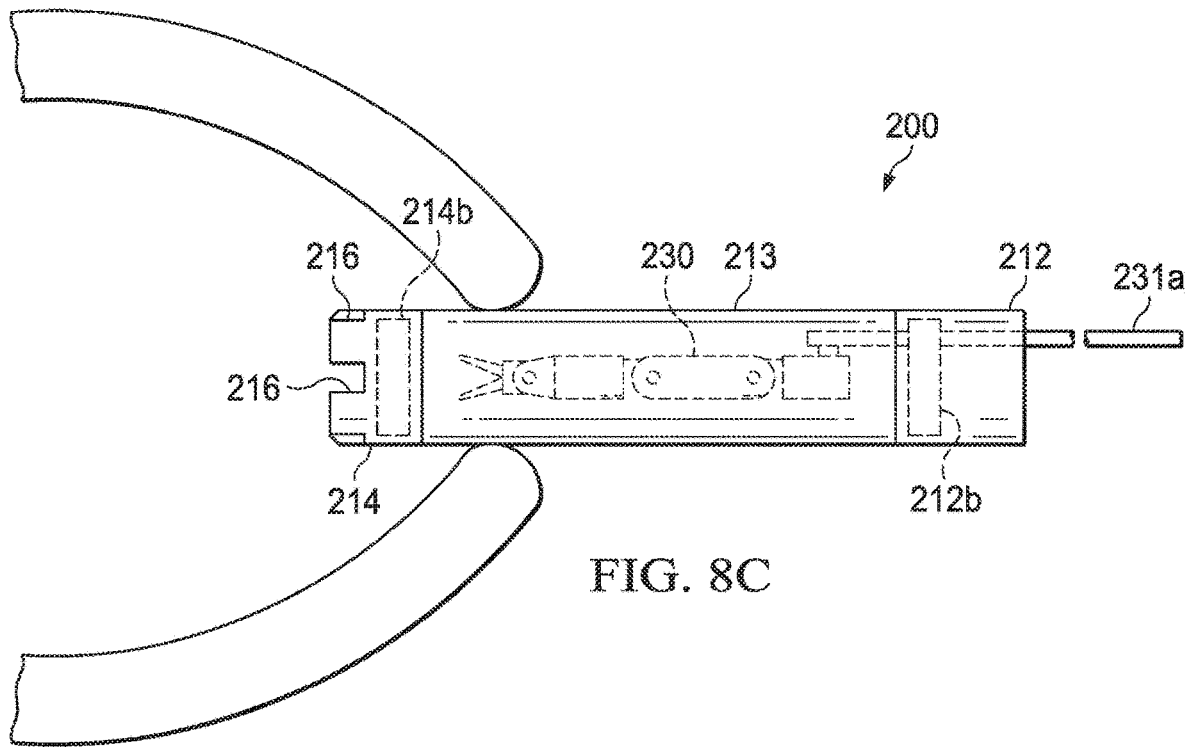
Figure 8D:
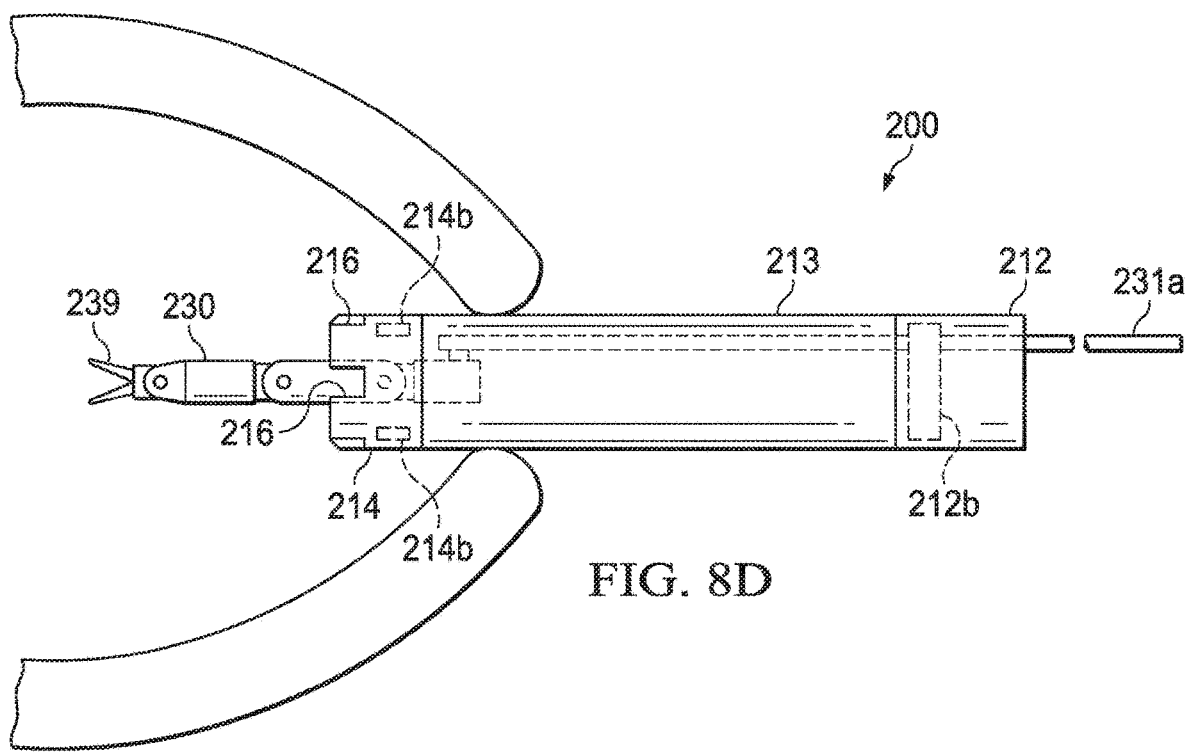
Figure 8E:
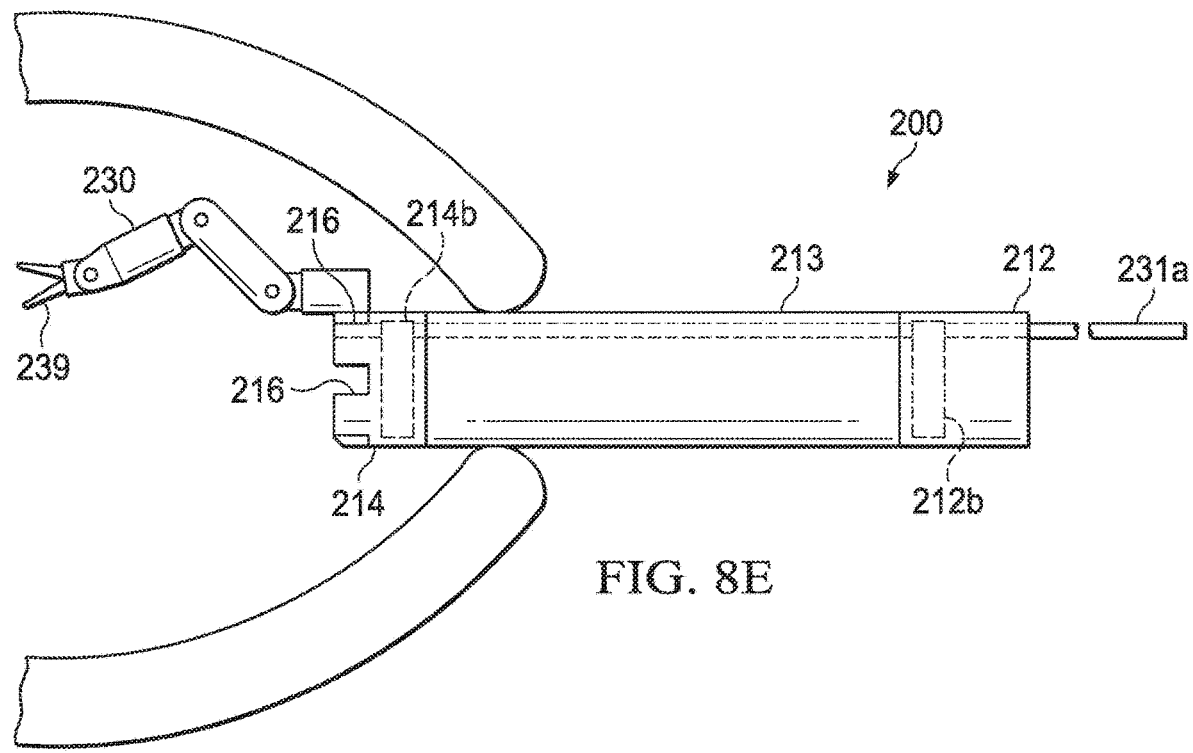

The instrument arm assembly 230 may be inserted through the central access channel 210*a* and secured to the anchor port 216 of the port assembly 210. To do so while maintaining the workable volume/space, the first gate assembly 212*b* may again be configured to the open position while the second gate assembly 214*b* is configured to the closed position. Once the first gate assembly 212*b* is in the open position, the instrument arm assembly 230 may be inserted into the mid section 213, as illustrated in FIG. 8B. The first gate assembly 212*b* may then be configured to the closed position after the instrument arm assembly 230 passes through the first gate assembly 212*b* and into the mid section 213, as illustrated in FIG. 8C. The second gate assembly 214*b* may then be configured to the open position, as illustrated in FIG. 8D. Once the second gate assembly 214*b* is in the open position, the instrument arm assembly 230 may be inserted into the cavity of the patient and the securing portion 231*a* secured to an anchor port 216, as illustrated in FIG. 8E. The second gate assembly 214*b* may then be configured to the closed position after the instrument arm assembly 230 passes through the second gate assembly 214*b*.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted into the port assembly 210 via the central access channel 210*a* in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210*a* of the port assembly 210 in a substantially reverse manner as described above for the inserting and attaching.

Method of Setting Up the Surgical Device 200 in a Reverse-Directed Position (e.g., Method 700)

As illustrated in FIGS. 7 and 8F-K, example embodiments of the surgical device 200 may be configurable to perform a reverse-directed surgical action or procedure in one of a plurality of ways. In an example embodiment, the external anchor 1 may be provided and installed/anchored to the stationary object in a similar manner as described above and in the present disclosure. The port assembly 210 may be provided (e.g., action 702), and the instrument arm assembly may be provided (e.g., action 704). A second instrument arm assembly may be provided, as well as the image capturing assembly 220 and/or 320 and any of the assistant arm assemblies 250 and/or 260 required. The port assembly 210 may be inserted (e.g., action 706) into the opening (and cavity) of the patient and anchored in position using the external anchor 1 (e.g., action 708), and a workable volume/space in the cavity may be formed, such as via insufflation using $CO_2$ and/or other gases, vacuum suction tools, and/or retractable hook tools. The controllable swivel assembly 1000 may also be used in example embodiments. For example, a workable abdominal cavity of about 10-12 cm in height may be provided for the patient. Thereafter, one or more image capturing assemblies 220, one or more assistant arm assemblies (e.g., action 710), and one or more assistant arm assemblies 250 or 260 (if needed) may be inserted into the port assembly 210 via the central access channel 210*a*, secured to the anchor ports 216, and configured in the cavity of the patient. For the inserting, each of the image capturing assemblies 220, instrument arm assemblies 230 and/or 240, and assistant arm assemblies 250 and/or 260 are inserted in reverse orientation as compared to the forward-directed position described above and in the present disclosure. A surgical action or procedure may then be performed in any part, area, and/or quadrant of the cavity of the patient using the surgical device 200. These processes will now be described below with references to at least FIGS. 7, 8F-K, 9B, and 10B.

(1) Providing the External Anchor and Installing the Port Assembly.

In an example embodiment, the port assembly 210 may be installed and secured to the external anchor 1 or 1000. As illustrated in FIGS. 8A-E, the second end 214 of the port assembly 210 is inserted into the opening of the patient and into the cavity of the patient and the first end 212 of the port assembly 210 is secured to the external anchor 1 or 1000. Thereafter, a workable volume/space in the cavity may be formed in the cavity of the patient, such as via insufflation using $CO_2$ and/or other gases, vacuum suction tools, and/or retractable hook tools. Before doing so, the first gate assembly 212b and the second gate assembly 214b may be expanded to the closed position. Insufflation of the cavity may be achieved in one or more of a plurality of ways. For example, the insufflation port of the port assembly 210 may be used to provide the required insufflation.

(2) Inserting and Attaching the Image Capturing Assembly.

Figure 8F:
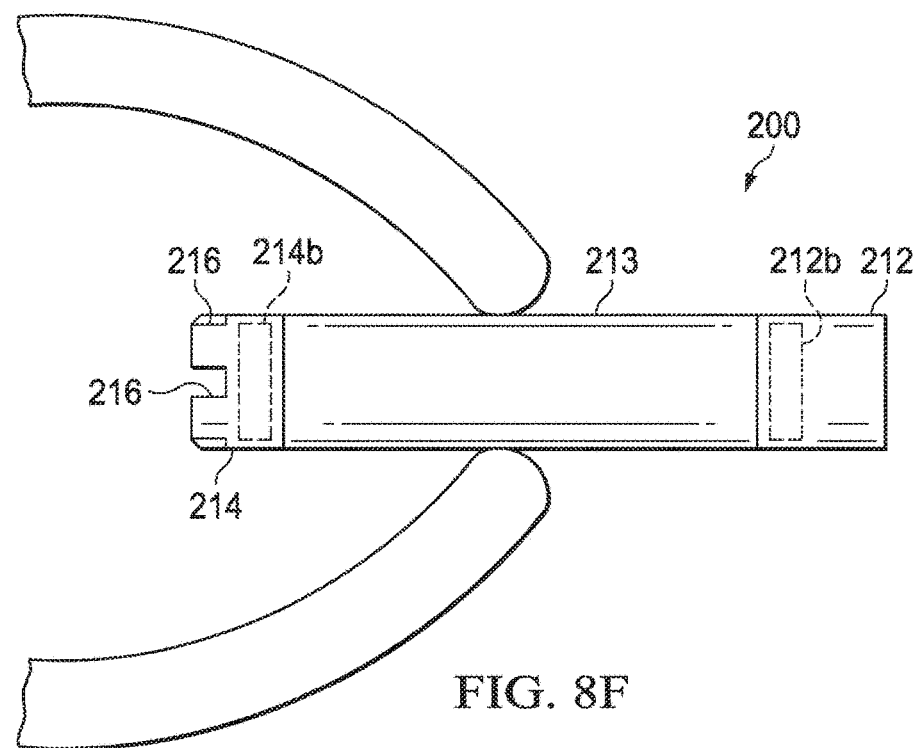
FIGS. 8F-K are illustrations of a side view of an example embodiment of a method of configuring a surgical device in a reverse-directed position.

After the workable volume/space in the cavity has been formed and the port assembly 210 is secured in position, as illustrated in FIG. 8F, the image capturing assembly 220 may be inserted with the image capturing body 224 inserted last through the central access channel 210a and secured to the anchor port 216 of the port assembly 210. To do so while maintaining the workable volume/space, the first gate assembly 212b may be configured to the open position while the second gate assembly 214b is configured to the closed position. Once the first gate assembly 212b is in the open position, the image capturing assembly 220 may be inserted into the mid section 213. The first gate assembly 212b may then be configured to the closed position after the image capturing assembly 220 passes through the first gate assembly 212b. The second gate assembly 214b may then be configured to the open position. It is recognized in the present disclosure that the workable volume/space in the cavity is maintained via the insufflation since the first gate assembly 212b is configured to the closed position. Once the second gate assembly 214b is in the open position, the image capturing assembly 220 may be inserted completely into the cavity of the patient with the image capturing body 224 being closest to the anchor port 216. The multi-curvable body 222 of the image capturing assembly 220 may then be configured/controlled to curve in one or more locations along the multi-curvable body 222 so that the image capturing assembly 220 can be directed in a reverse-directed position next to the outer surface of the port assembly 210 (as illustrated in FIGS. 2A and 3A). The image capturing assembly 220 may then be provided adjacent to the outer surface of the port assembly 210 so that the anchoring portion 220a of the image capturing assembly 220 is adjacent to the anchor port 216. The anchoring portion 220a of the image capturing assembly 220 may then be secured to the anchor port 216. The second gate assembly 214b may be configured to the closed position after the image capturing assembly 220 passes through the second gate assembly 214b.

The separate image capturing assembly 320 may also be inserted through the port assembly 210 in a similar manner as described above. Once inserted through the port assembly 210 and into the cavity of the patient, the separate image capturing assembly 320 may then be attached/secured to the interior wall of the cavity of the patient via the magnetic anchor 310.

(3) Inserting and Attaching a First Instrument Arm Assembly.

Figure 8G:
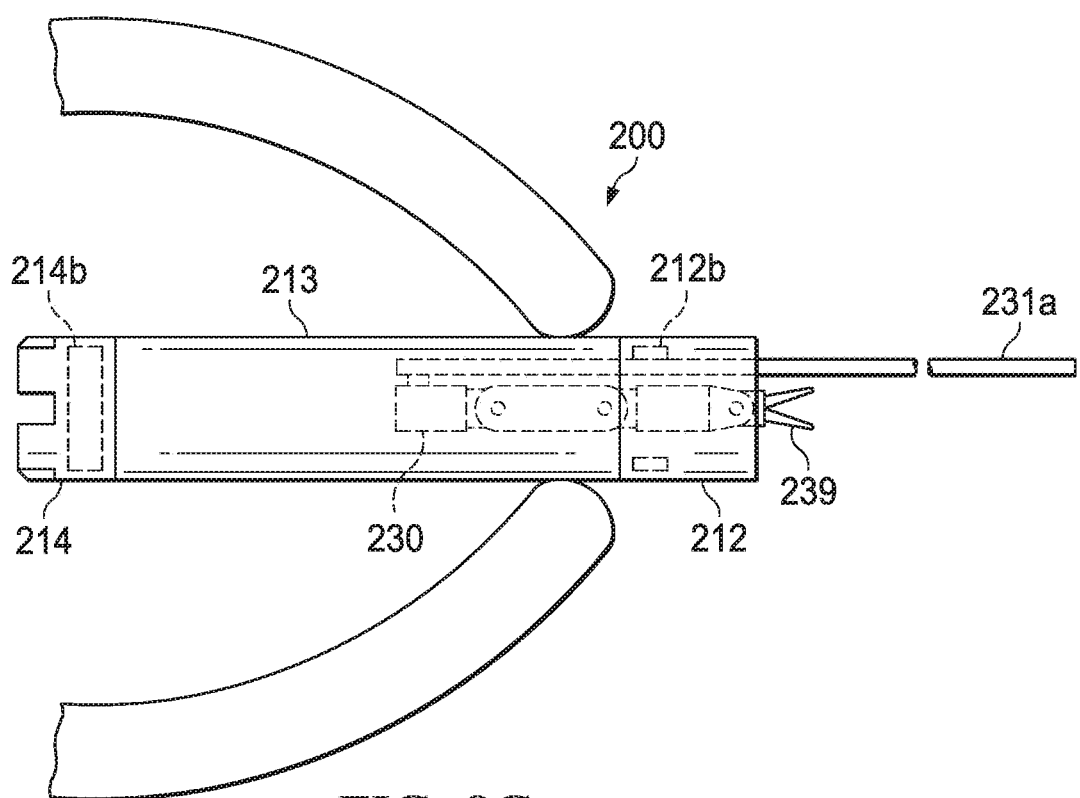
Figure 8H:
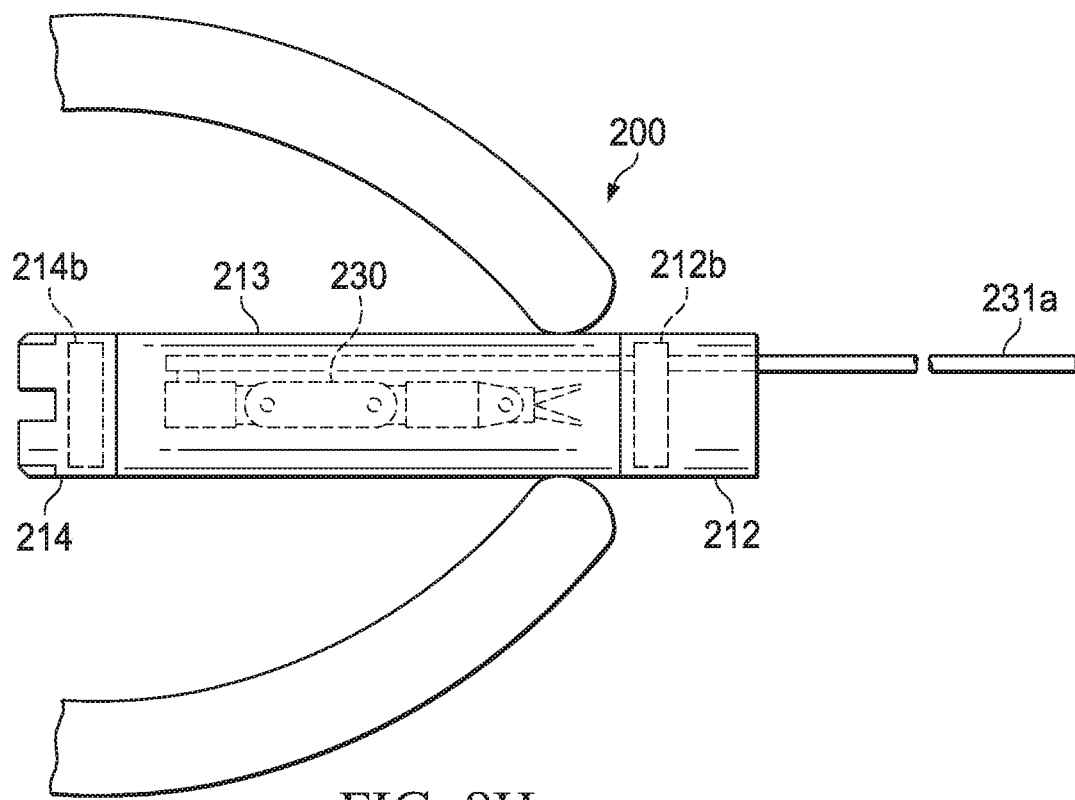
Figure 8I:
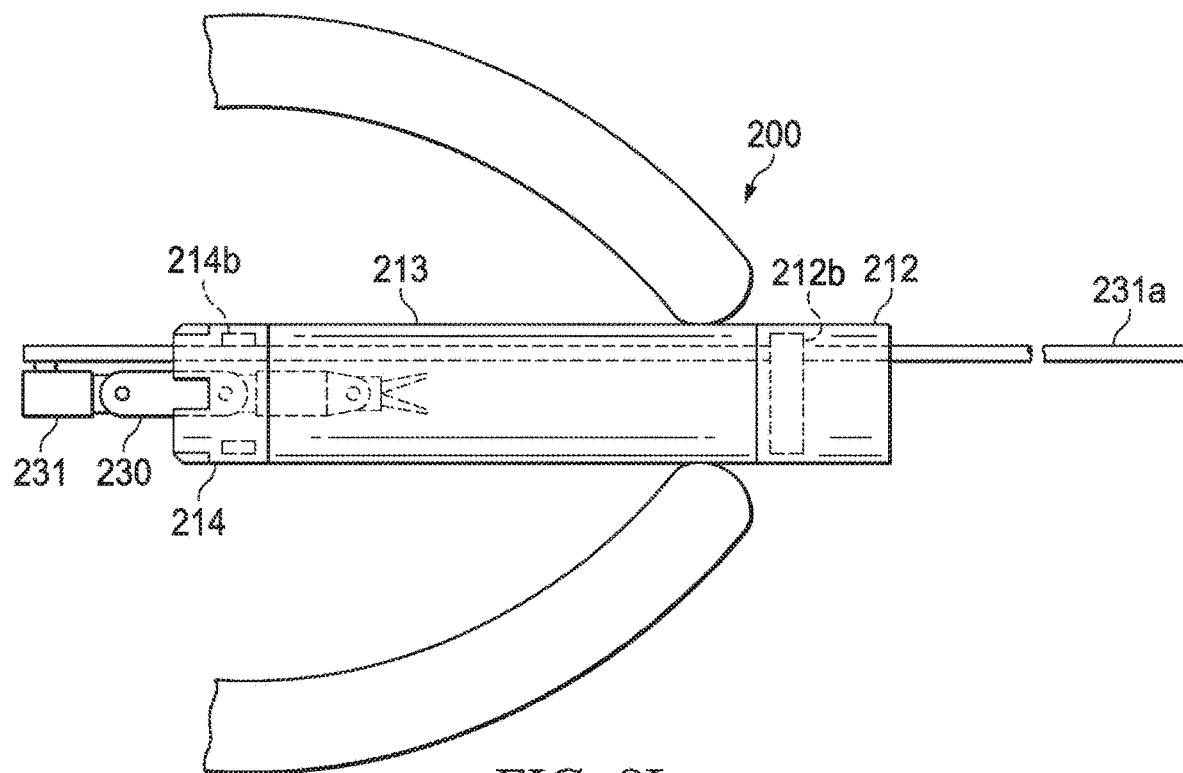
Figure 8J:
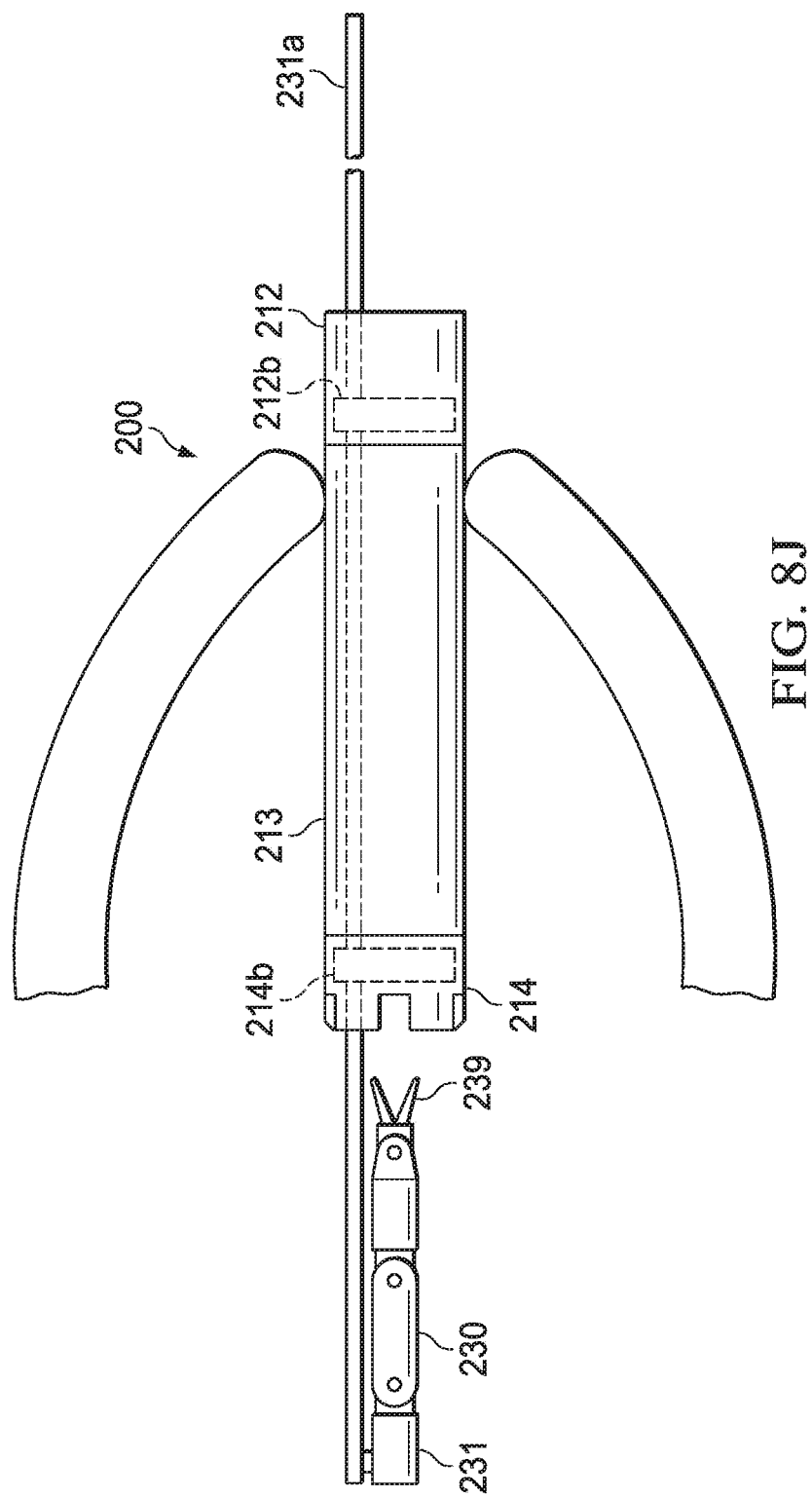
Figure 8K:
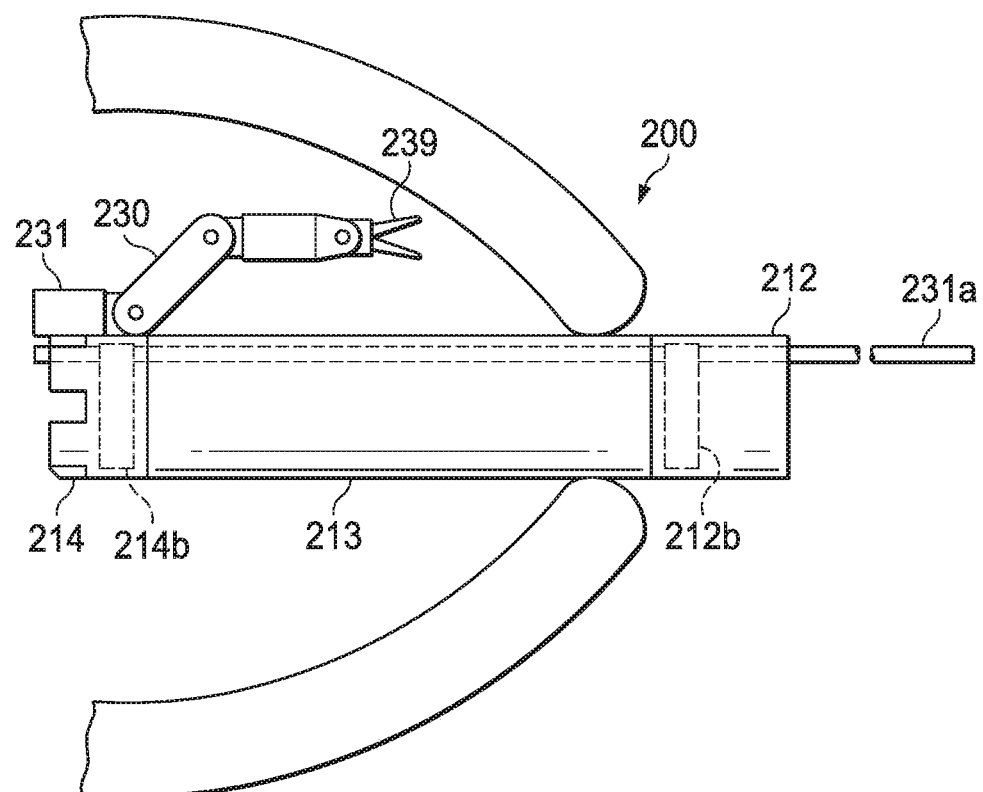

To insert the instrument arm assembly 230 through the central access channel 210a and secure it to the anchor port 216 of the port assembly 210 while maintaining the workable volume/space, the first gate assembly 212b may again be configured to the open position while the second gate assembly 214b is configured to the closed position. Once the first gate assembly 212b is in the open position, the instrument arm assembly 230 may be inserted with the end effector 239, 342, 344 inserted last into the mid section 213, as illustrated in FIG. 8G. The first gate assembly 212b may then be configured to the closed position after the instrument arm assembly 230 passes through the first gate assembly 212b and into the mid section 213, as illustrated in FIG. 8H. The second gate assembly 214b may then be configured to the open position, as illustrated in FIG. 8I. Once the second gate assembly 214b is in the open position, the instrument arm assembly 230 may be inserted completely into the cavity of the patient with the end effector 239, 342, 344 being closest to the anchor port 216, as illustrated in FIG. 8J. The instrument arm assembly 230 may then be turned 180 degrees (if needed) and/or moved so that the instrument arm assembly 230 can be brought next to the outer surface of the port assembly 210. The instrument arm assembly 230 may then be pulled adjacent to the outer surface of the port assembly 210 so that the securing portion 231a of the shoulder section 231 of the instrument arm assembly 230 is adjacent to the anchor port 216. The securing portion 231a of the instrument arm assembly 230 may then be secured to the anchor port 216, as illustrated in FIG. 8K. The second gate assembly 214b may be configured to the closed position at any time after at least the end effector 230 of the instrument arm assembly 230 passes through the second gate assembly 214b.

(5) Inserting and Attaching One or More Additional Instrument Arm Assemblies, One or More Assistant Arm Assemblies, and/or One or More Additional Camera Arm Assemblies.

One or more additional instrument arm assemblies 240, one or more assistant arm assemblies 250 or 260, and/or one or more additional image capturing assemblies (not shown) may also be inserted and installed in a reverse-directed manner via the central access channel 210a of the port assembly 210 in the same manner as described above for the image capturing assembly 220 and the instrument arm assembly 230.

(6) Unattaching and Removing the Instrument Arm Assembly, Image Capturing Assembly, and Assistant Arm Assemblies.

The instrument arm assembly 230, image capturing assembly 220, other instrument arm assembly 240 (if provided), other image capturing assembly (if provided), and the one or more other assistant arm assemblies 250 or 260 (if provided) may be unattached (or unsecured) from the anchor ports 216 and removed from the cavity of the patient via the central access channel 210a of the port assembly 210 in a substantially reverse manner as described above for the inserting and attaching in the reverse-directed manner.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A surgical arm assembly for performing a surgical action, the surgical arm assembly comprising:
   an end-effector assembly, the end-effector assembly including a first instrument for performing a surgical action;
   a first arm assembly having an elongated first arm assembly body, a proximal end, and distal end, the distal end of the first arm assembly securable to the end-effector assembly;
   an elbow joint assembly, the elbow joint assembly including:
      a distal end, the distal end of the elbow joint assembly secured to the proximal end of the first arm assembly; and
      a proximal end, the proximal end of the elbow joint assembly secured to a distal end of a second arm assembly;
   the second arm assembly, the second arm assembly including:
      an elongated second arm assembly body;
      a first elbow drive assembly, the first elbow drive assembly housed in the second arm assembly body, the first elbow drive assembly having an integrated motor, the integrated motor of the first elbow drive assembly configured to drive the elbow joint assembly to pivotally move the first arm assembly relative to a first axis; and
      a second elbow drive assembly, the second elbow drive assembly housed in the second arm assembly body, the second elbow drive assembly having an integrated motor, the integrated motor of the second elbow drive assembly configured to drive the elbow joint assembly to pivotally move the first arm assembly relative to a second axis.

2. The surgical arm assembly of claim 1,
   wherein the elbow joint assembly includes a first driven portion housed in the elbow joint assembly;
   wherein the first elbow drive assembly includes a first drive portion, the first drive portion configured to translate a first rotary force from the integrated motor of the first elbow drive assembly to the first driven portion; and
   wherein the first drive portion is configured in such a way that, when the integrated motor of the first elbow drive assembly applies the first rotary force to the first drive portion, the first drive portion drives the first driven portion to pivotally move the first arm assembly relative to the first axis.

3. The surgical arm assembly of claim 1,
   wherein the elbow joint assembly includes a second driven portion housed in the elbow joint assembly;
   wherein the second elbow drive assembly includes a second drive portion, the second drive portion configured to translate a second rotary force from the integrated motor of the second elbow drive assembly to the second driven portion; and
   wherein the second drive portion is configured in such a way that, when the integrated motor of the second elbow drive assembly applies the second rotary force to the second drive portion, the second drive portion drives the first driven portion to pivotally move the first arm assembly relative to the first axis.

4. The surgical arm assembly of claim 1, further comprising:
- a shoulder joint assembly, the shoulder joint assembly including:
  - a distal end, the distal end of the shoulder joint assembly secured to a proximal end of the second arm assembly; and
  - a proximal end, the proximal end of the shoulder joint assembly secured to a distal end of a shoulder section; and
- the shoulder section.

5. The surgical arm assembly of claim 4, wherein the second arm assembly further comprises:
- a first shoulder drive assembly, the first shoulder drive assembly housed in the second arm assembly body, the first shoulder drive assembly having an integrated motor, the integrated motor of the first shoulder drive assembly configured to drive the shoulder joint assembly to pivotally move the second arm assembly relative to a third axis; and
- a second shoulder drive assembly, the second shoulder drive assembly housed in the second arm assembly body, the second shoulder drive assembly having an integrated motor, the integrated motor of the second shoulder drive assembly configured to drive the shoulder joint assembly to pivotally move the second arm assembly relative to a fourth axis.

6. The surgical arm assembly of claim 5,
wherein the shoulder joint assembly includes a first driven portion housed in the shoulder joint assembly;
wherein the first shoulder drive assembly includes a first drive portion, the first drive portion of the first shoulder drive assembly configured to translate a first rotary force from the integrated motor of the first shoulder drive assembly to the first driven portion of the shoulder joint assembly; and
wherein the first drive portion of the first shoulder drive assembly is configured in such a way that, when the integrated motor of the first shoulder drive assembly applies the first rotary force to the first drive portion of the first shoulder drive assembly, the first drive portion of the first shoulder drive assembly drives the first driven portion of the shoulder joint assembly to pivotally move the second arm assembly relative to the third axis.

7. The surgical arm assembly of claim 5,
wherein the shoulder joint assembly includes a second driven portion housed in the shoulder joint assembly;
wherein the second shoulder drive assembly includes a second drive portion, the second drive portion of the second shoulder drive assembly configured to translate a second rotary force from the integrated motor of the second shoulder drive assembly to the second driven portion of the shoulder joint assembly; and
wherein the second drive portion of the second shoulder drive assembly is configured in such a way that, when the integrated motor of the second shoulder drive assembly applies the second rotary force to the second drive portion of the second shoulder drive assembly, the second drive portion of the second shoulder drive assembly drives the second driven portion of the shoulder joint assembly to pivotally move the second arm assembly relative to the fourth axis.

8. The surgical arm assembly of claim 5, wherein at least one of the following apply:
- the first axis is different from the second axis;
- the third axis is different from the fourth axis;
- the first axis does not intersect with the second axis; and
- the third axis does not intersect with the fourth axis.

9. The surgical arm assembly of claim 1, wherein the first arm assembly comprises:
- a first instrument drive assembly, the first instrument drive assembly housed in the first arm assembly body, the first instrument drive assembly having an integrated motor, the integrated motor of the first instrument drive assembly configured to pivotally move the first instrument relative to a fifth axis;
- a wrist drive assembly, the wrist drive assembly housed in the first arm assembly body, the wrist drive assembly having an integrated motor, the integrated motor of the wrist drive assembly configured to pivotally move the first instrument relative a sixth axis, the sixth axis different from the fifth axis; and
- a first arm assembly drive assembly, the first arm assembly drive assembly housed in the first arm assembly body, the first arm assembly drive assembly having an integrated motor, the integrated motor of the first arm assembly drive assembly configured to rotate at least the end-effector assembly relative to a seventh axis, the seventh axis formed by a center line drawn through the first arm assembly body.

10. The surgical arm assembly of claim 9,
wherein the end-effector assembly further comprises a second instrument; and
wherein the first arm assembly further comprises a second instrument drive assembly, the second instrument drive assembly housed in the first arm assembly body, the second instrument drive assembly having an integrated motor, the integrated motor of the second instrument drive assembly configured to pivotally move the second instrument relative to the fifth axis.

11. A surgical arm assembly for performing a surgical action, the surgical arm assembly comprising:
- an end-effector assembly, the end-effector assembly including a first instrument for performing a surgical action;
- a first arm assembly having an elongated first arm assembly body, a proximal end, and distal end, the distal end of the first arm assembly securable to the end-effector assembly;
- an elbow joint assembly, the elbow joint assembly including:
  - a distal end, the distal end of the elbow joint assembly secured to the proximal end of the first arm assembly; and
  - a proximal end, the proximal end of the elbow joint assembly secured to a distal end of a second arm assembly;
- the second arm assembly, the second arm assembly including:
  - an elongated second arm assembly body;
  - a first elbow drive assembly, the first elbow drive assembly housed in the second arm assembly body, the first elbow drive assembly having an integrated motor, the integrated motor of the first elbow drive assembly configured to drive the elbow joint assembly to pivotally move the first arm assembly relative to a first axis;
  - a second elbow drive assembly, the second elbow drive assembly housed in the second arm assembly body, the second elbow drive assembly having an integrated motor, the integrated motor of the second elbow drive assembly configured to drive the elbow joint assembly to pivotally move the first arm assembly relative to a second axis; and
a first shoulder drive assembly, the first shoulder drive assembly housed in the second arm assembly body, the first shoulder drive assembly having an integrated motor, the integrated motor of the first shoulder drive assembly configured to drive a shoulder joint assembly to pivotally move the second arm assembly relative to a third axis;
the shoulder joint assembly, the shoulder joint assembly including:
a distal end, the distal end of the shoulder joint assembly secured to a proximal end of the second arm assembly; and
a proximal end, the proximal end of the shoulder joint assembly secured to a distal end of a shoulder section; and
the shoulder section.

12. The surgical arm assembly of claim 11,
wherein the elbow joint assembly includes a first driven portion housed in the elbow joint assembly;
wherein the first elbow drive assembly includes a first drive portion, the first drive portion configured to translate a first rotary force from the integrated motor of the first elbow drive assembly to the first driven portion; and
wherein the first drive portion is configured in such a way that, when the integrated motor of the first elbow drive assembly applies the first rotary force to the first drive portion, the first drive portion drives the first driven portion to pivotally move the first arm assembly relative to the first axis.

13. The surgical arm assembly of claim 11,
wherein the elbow joint assembly includes a second driven portion housed in the elbow joint assembly;
wherein the second elbow drive assembly includes a second drive portion, the second drive portion configured to translate a second rotary force from the integrated motor of the second elbow drive assembly to the second driven portion; and
wherein the second drive portion is configured in such a way that, when the integrated motor of the second elbow drive assembly applies the second rotary force to the second drive portion, the second drive portion drives the first driven portion to pivotally move the first arm assembly relative to the first axis.

14. The surgical arm assembly of claim 11, wherein the second arm assembly further comprises:
a second shoulder drive assembly, the second shoulder drive assembly housed in the second arm assembly body, the second shoulder drive assembly having an integrated motor, the integrated motor of the second shoulder drive assembly configured to drive the shoulder joint assembly to pivotally move the second arm assembly relative to a fourth axis.

15. The surgical arm assembly of claim 14,
wherein the shoulder joint assembly includes a second driven portion housed in the shoulder joint assembly;
wherein the second shoulder drive assembly includes a second drive portion, the second drive portion of the second shoulder drive assembly configured to translate a second rotary force from the integrated motor of the second shoulder drive assembly to the second driven portion of the shoulder joint assembly; and
wherein the second drive portion of the second shoulder drive assembly is configured in such a way that, when the integrated motor of the second shoulder drive assembly applies the second rotary force to the second drive portion of the second shoulder drive assembly, the second drive portion of the second shoulder drive assembly drives the second driven portion of the shoulder joint assembly to pivotally move the second arm assembly relative to the fourth axis.

16. The surgical arm assembly of claim 14, wherein at least one of the following apply:
the first axis is different from the second axis;
the third axis is different from the fourth axis;
the first axis does not intersect with the second axis; and
the third axis does not intersect with the fourth axis.

17. The surgical arm assembly of claim 11,
wherein the shoulder joint assembly includes a first driven portion housed in the shoulder joint assembly;
wherein the first shoulder drive assembly includes a first drive portion, the first drive portion of the first shoulder drive assembly configured to translate a first rotary force from the integrated motor of the first shoulder drive assembly to the first driven portion of the shoulder joint assembly; and
wherein the first drive portion of the first shoulder drive assembly is configured in such a way that, when the integrated motor of the first shoulder drive assembly applies the first rotary force to the first drive portion of the first shoulder drive assembly, the first drive portion of the first shoulder drive assembly drives the first driven portion of the shoulder joint assembly to pivotally move the second arm assembly relative to the third axis.

18. The surgical arm assembly of claim 11, wherein the first arm assembly comprises:
a first instrument drive assembly, the first instrument drive assembly housed in the first arm assembly body, the first instrument drive assembly having an integrated motor, the integrated motor of the first instrument drive assembly configured to pivotally move the first instrument relative to a fifth axis;
a wrist drive assembly, the wrist drive assembly housed in the first arm assembly body, the wrist drive assembly having an integrated motor, the integrated motor of the wrist drive assembly configured to pivotally move the first instrument relative a sixth axis, the sixth axis different from the fifth axis; and
a first arm assembly drive assembly, the first arm assembly drive assembly housed in the first arm assembly body, the first arm assembly drive assembly having an integrated motor, the integrated motor of the first arm assembly drive assembly configured to rotate at least the end-effector assembly relative to a seventh axis, the seventh axis formed by a center line drawn through the first arm assembly body.

19. The surgical arm assembly of claim 18,
wherein the end-effector assembly further comprises a second instrument; and
wherein the first arm assembly further comprises a second instrument drive assembly, the second instrument drive assembly housed in the first arm assembly body, the second instrument drive assembly having an integrated motor, the integrated motor of the second instrument drive assembly configured to pivotally move the second instrument relative to the fifth axis.

20. A surgical arm assembly for performing a surgical action, the surgical arm assembly comprising:
an end-effector assembly, the end-effector assembly including a first instrument for performing a surgical action;

a first arm assembly having an elongated first arm assembly body, a proximal end, and distal end, the distal end of the first arm assembly securable to the end-effector assembly;

an elbow joint assembly, the elbow joint assembly including:
- a distal end, the distal end of the elbow joint assembly secured to the proximal end of the first arm assembly; and
- a proximal end, the proximal end of the elbow joint assembly secured to a distal end of a second arm assembly;

the second arm assembly, the second arm assembly including:
- an elongated second arm assembly body;
- a first elbow drive assembly, the first elbow drive assembly housed in the second arm assembly body, the first elbow drive assembly having an integrated motor, the integrated motor of the first elbow drive assembly configured to drive the elbow joint assembly to pivotally move the first arm assembly relative to a first axis;
- a second elbow drive assembly, the second elbow drive assembly housed in the second arm assembly body, the second elbow drive assembly having an integrated motor, the integrated motor of the second elbow drive assembly configured to drive the elbow joint assembly to pivotally move the first arm assembly relative to a second axis;
- a first shoulder drive assembly, the first shoulder drive assembly housed in the second arm assembly body, the first shoulder drive assembly having an integrated motor, the integrated motor of the first shoulder drive assembly configured to drive a shoulder joint assembly to pivotally move the second arm assembly relative to a third axis; and
- a second shoulder drive assembly, the second shoulder drive assembly housed in the second arm assembly body, the second shoulder drive assembly having an integrated motor, the integrated motor of the second shoulder drive assembly configured to drive the shoulder joint assembly to pivotally move the second arm assembly relative to a fourth axis;

the shoulder joint assembly, the shoulder joint assembly including:
- a distal end, the distal end of the shoulder joint assembly secured to a proximal end of the second arm assembly; and
- a proximal end, the proximal end of the shoulder joint assembly secured to a distal end of a shoulder section; and the shoulder section.

21. The surgical arm assembly of claim 20,
wherein the elbow joint assembly includes a first driven portion housed in the elbow joint assembly;
wherein the first elbow drive assembly includes a first drive portion, the first drive portion configured to translate a first rotary force from the integrated motor of the first elbow drive assembly to the first driven portion; and
wherein the first drive portion is configured in such a way that, when the integrated motor of the first elbow drive assembly applies the first rotary force to the first drive portion, the first drive portion drives the first driven portion to pivotally move the first arm assembly relative to the first axis.

22. The surgical arm assembly of claim 20,
wherein the elbow joint assembly includes a second driven portion housed in the elbow joint assembly;
wherein the second elbow drive assembly includes a second drive portion, the second drive portion configured to translate a second rotary force from the integrated motor of the second elbow drive assembly to the second driven portion; and
wherein the second drive portion is configured in such a way that, when the integrated motor of the second elbow drive assembly applies the second rotary force to the second drive portion, the second drive portion drives the first driven portion to pivotally move the first arm assembly relative to the first axis.

23. The surgical arm assembly of claim 20,
wherein the shoulder joint assembly includes a first driven portion housed in the shoulder joint assembly;
wherein the first shoulder drive assembly includes a first drive portion, the first drive portion of the first shoulder drive assembly configured to translate a first rotary force from the integrated motor of the first shoulder drive assembly to the first driven portion of the shoulder joint assembly; and
wherein the first drive portion of the first shoulder drive assembly is configured in such a way that, when the integrated motor of the first shoulder drive assembly applies the first rotary force to the first drive portion of the first shoulder drive assembly, the first drive portion of the first shoulder drive assembly drives the first driven portion of the shoulder joint assembly to pivotally move the second arm assembly relative to the third axis.

24. The surgical arm assembly of claim 20,
wherein the shoulder joint assembly includes a second driven portion housed in the shoulder joint assembly;
wherein the second shoulder drive assembly includes a second drive portion, the second drive portion of the second shoulder drive assembly configured to translate a second rotary force from the integrated motor of the second shoulder drive assembly to the second driven portion of the shoulder joint assembly; and
wherein the second drive portion of the second shoulder drive assembly is configured in such a way that, when the integrated motor of the second shoulder drive assembly applies the second rotary force to the second drive portion of the second shoulder drive assembly, the second drive portion of the second shoulder drive assembly drives the second driven portion of the shoulder joint assembly to pivotally move the second arm assembly relative to the fourth axis.

25. The surgical arm assembly of claim 20, wherein at least one of the following apply:
the first axis is different from the second axis;
the third axis is different from the fourth axis;
the first axis does not intersect with the second axis; and
the third axis does not intersect with the fourth axis.

26. The surgical arm assembly of claim 20, wherein the first arm assembly comprises:
a first instrument drive assembly, the first instrument drive assembly housed in the first arm assembly body, the first instrument drive assembly having an integrated motor, the integrated motor of the first instrument drive assembly configured to pivotally move the first instrument relative to a fifth axis;
a wrist drive assembly, the wrist drive assembly housed in the first arm assembly body, the wrist drive assembly having an integrated motor, the integrated motor of the wrist drive assembly configured to pivotally move the first instrument relative a sixth axis, the sixth axis different from the fifth axis; and a first arm assembly drive assembly, the first arm assembly drive assembly housed in the first arm assembly body, the first arm assembly drive assembly having an integrated motor, the integrated motor of the first arm assembly drive assembly configured to rotate at least the end-effector assembly relative to a seventh axis, the seventh axis formed by a center line drawn through the first arm assembly body.

27. The surgical arm assembly of claim 26, wherein the end-effector assembly further comprises a second instrument; and wherein the first arm assembly further comprises a second instrument drive assembly, the second instrument drive assembly housed in the first arm assembly body, the second instrument drive assembly having an integrated motor, the integrated motor of the second instrument drive assembly configured to pivotally move the second instrument relative to the fifth axis.

\* \* \* \* \*